US012559691B2

(12) United States Patent
Goloubkov

(10) Patent No.: US 12,559,691 B2
(45) Date of Patent: Feb. 24, 2026

(54) METHOD FOR PRODUCING MOTOR FUEL FROM ETHANOL

(71) Applicant: Swedish Biofuels AB, Stockholm (SE)

(72) Inventor: Igor Goloubkov, Lidingo (SE)

(73) Assignee: Swedish Biofuels AB, Stockholm (SE)

( * ) Notice: Subject to any disclaimer, the term of this patent is extended or adjusted under 35 U.S.C. 154(b) by 120 days.

(21) Appl. No.: 18/574,254

(22) PCT Filed: Jul. 4, 2022

(86) PCT No.: PCT/SE2022/050676
§ 371 (c)(1),
(2) Date: Dec. 26, 2023

(87) PCT Pub. No.: WO2023/033692
PCT Pub. Date: Mar. 9, 2023

(65) Prior Publication Data
US 2025/0290001 A1     Sep. 18, 2025

(30) Foreign Application Priority Data

Aug. 31, 2021   (EP) ..................................... 21194166
Aug. 31, 2021   (SE) .................................... 2151091-2

(51) Int. Cl.
*C10L 1/02*      (2006.01)
*C07C 29/136*    (2006.01)
(Continued)

(52) U.S. Cl.
CPC .............. *C10L 1/02* (2013.01); *C07C 29/136* (2013.01); *C07C 29/32* (2013.01); *C10G 3/49* (2013.01);
(Continued)

(58) Field of Classification Search
CPC ..... B01J 23/10; B01J 29/405; C07C 2521/04; C07C 2521/10; C07C 2523/06;
(Continued)

(56) References Cited

U.S. PATENT DOCUMENTS 8,049,048 B2    11/2011  Rusek
8,153,850 B2     4/2012  Hall
(Continued)

FOREIGN PATENT DOCUMENTS

AU      2013203230 B2    5/2013
CA         2677826 C     9/2008
(Continued)

OTHER PUBLICATIONS

Wei-Cheng Wang and Ling Tao, "Bio-Jet Fuel Conversion Technologies", Jan. 2016, pp. 801-822, vol. 53, Elsevier, Renewable and Sustainable Energy Reviews, https://www.sciencedirect.com/science/article/pii/S1364032115009867.
(Continued)

*Primary Examiner* — Ellen M Mcavoy
*Assistant Examiner* — Chantel Graham
(74) *Attorney, Agent, or Firm* — Jeffrey L. Streets

(57) ABSTRACT

A method for making a motor fuel includes converting a mixture comprising one or more $C_2$-$C_4$ alkenes, synthesis gas, and acetaldehyde to a mixture comprising $C_3$-$C_4$ aldehydes and $C_5$-$C_8$ aldols; hydrogenating the mixture comprising $C_3$-$C_4$ aldehydes and $C_5$-$C_8$ aldols to obtain a mixture comprising $C_3$-$C_8$ alcohols; converting the $C_3$-$C_8$ alcohols into $C_6$-$C_{24}$ paraffins; and isolating a fraction of the $C_6$-$C_{24}$ paraffins. The isolated fraction may be used to formulate a motor fuel.

20 Claims, 1 Drawing Sheet

(51) Int. Cl.
| | | |
|---|---|---|
| *C07C 29/32* | (2006.01) | |
| *C10G 3/00* | (2006.01) | |
| *C10L 1/04* | (2006.01) | |

(52) U.S. Cl.
CPC ............ *C10L 1/04* (2013.01); *C07C 2521/04* (2013.01); *C07C 2521/10* (2013.01); *C07C 2523/06* (2013.01); *C07C 2523/10* (2013.01); *C10G 2300/1014* (2013.01); *C10G 2400/02* (2013.01); *C10G 2400/04* (2013.01); *C10L 2200/0423* (2013.01); *C10L 2200/043* (2013.01); *C10L 2200/0446* (2013.01); *C10L 2290/141* (2013.01)

(58) Field of Classification Search
CPC ............... C07C 2523/10; C07C 29/32; C10G 2300/1014; C10G 2300/1022; C10G 2400/02; C10G 2400/04; C10G 2400/08; C10G 3/00; C10G 3/49; C10G 5/00; C10G 69/00; C10G 69/12; C10L 1/02; C10L 2200/0423; C10L 2200/043; C10L 2200/0446; Y02E 50/10; Y02P 30/20
See application file for complete search history.

(56) References Cited

U.S. PATENT DOCUMENTS

| | | | |
|---|---|---|---|
| 8,193,402 B2 | 6/2012 | Gruber | |
| 8,313,934 B2 | 11/2012 | Bhatia | |
| 8,373,012 B2 | 2/2013 | Peters | |
| 8,404,355 B2 | 3/2013 | Jansen | |
| 8,487,149 B2 | 7/2013 | Gruber | |
| 8,546,627 B2 | 10/2013 | Gruber | |
| 8,563,282 B2 | 10/2013 | Galvez | |
| 8,852,296 B2 | 10/2014 | Rusek | |
| 8,933,281 B2 | 1/2015 | Cortright | |
| 8,969,050 B2 | 3/2015 | Austin | |
| 9,017,984 B2 | 4/2015 | Hu | |
| 9,074,173 B2 | 7/2015 | Walther | |
| 9,156,755 B2 | 10/2015 | Yao | |
| 9,228,134 B1 | 1/2016 | Cortright | |
| 9,476,106 B2 | 10/2016 | Eyal | |
| 9,688,590 B2 | 6/2017 | Cross | |
| 9,738,909 B1 | 8/2017 | Liang | |
| 9,764,997 B1 | 9/2017 | Harvey | |
| 9,771,533 B2 | 9/2017 | Lilga | |
| 9,790,444 B2 | 10/2017 | Baer | |
| 9,840,676 B1 | 12/2017 | Harvey | |
| 9,862,655 B2 | 1/2018 | Fichtl | |
| 9,890,401 B2 | 2/2018 | Hu | |
| 9,914,672 B2 | 3/2018 | Greene | |
| 9,932,531 B2 | 4/2018 | Lilga | |
| 2005/0112739 A1* | 5/2005 | Golubkov | C12P 7/54 |
| | | | 435/161 |
| 2007/0287873 A1* | 12/2007 | Coupard | C10G 3/62 |
| | | | 585/639 |
| 2009/0124839 A1 | 5/2009 | Dumesic et al. | |
| 2009/0139134 A1 | 6/2009 | Yoshikuni et al. | |
| 2010/0146843 A1 | 6/2010 | Dumenil | |
| 2011/0126448 A1 | 6/2011 | Dumenil | |
| 2011/0250663 A1 | 10/2011 | Schirmer et al. | |
| 2011/0296744 A1 | 12/2011 | Jones | |
| 2012/0058526 A1 | 3/2012 | Jansen et al. | |
| 2012/0156742 A1 | 6/2012 | Powell et al. | |
| 2012/0156743 A1 | 6/2012 | Powell et al. | |
| 2012/0178154 A1 | 7/2012 | Genta et al. | |
| 2012/0198760 A1 | 8/2012 | Blommel et al. | |
| 2012/0259146 A1 | 10/2012 | Gruber et al. | |
| 2012/0271081 A1 | 10/2012 | Nesterenko et al. | |
| 2012/0271085 A1 | 10/2012 | Nesterenko et al. | |
| 2013/0144094 A1 | 6/2013 | Pansare et al. | |
| 2013/0232852 A1 | 9/2013 | Peterson et al. | |
| 2013/0237728 A1 | 9/2013 | Lotero et al. | |
| 2014/0114231 A1 | 4/2014 | Rostro | |

| | | | |
|---|---|---|---|
| 2015/0045599 A1 | 2/2015 | Frey et al. | |
| 2015/0210927 A1 | 7/2015 | Hall et al. | |
| 2015/0376511 A1 | 12/2015 | Lotero et al. | |
| 2015/0376833 A1 | 12/2015 | Paripati et al. | |
| 2016/0108323 A1 | 4/2016 | Marshall et al. | |
| 2016/0312131 A1 | 10/2016 | Luebke et al. | |
| 2016/0312134 A1 | 10/2016 | Fichtl et al. | |
| 2016/0362612 A1 | 12/2016 | Wyman et al. | |
| 2019/0233751 A1 | 8/2019 | Medoff | |
| 2020/0010767 A1 | 1/2020 | Smith et al. | |
| 2020/0165176 A1 | 5/2020 | Dagle et al. | |

FOREIGN PATENT DOCUMENTS

| | | | |
|---|---|---|---|
| CA | 2705853 A1 | 5/2009 | |
| CA | 2745220 A1 | 6/2010 | |
| CA | 2669361 A1 | 11/2010 | |
| CA | 2800057 A1 | 9/2011 | |
| CA | 2846289 A1 | 4/2013 | |
| CA | 2972841 A1 | 10/2017 | |
| CA | 3076104 A1 | 4/2019 | |
| CN | 1168129 A | 12/1997 | |
| CN | 105063116 A | 11/2015 | |
| CN | 103201395 B | 3/2016 | |
| CN | 104650947 B | 1/2017 | |
| CN | 105132003 B | 4/2017 | |
| CN | 106866345 A | 6/2017 | |
| CN | 107142122 A | 9/2017 | |
| CN | 107200722 A | 9/2017 | |
| CN | 107794074 A | 3/2018 | |
| CN | 107841332 A | 3/2018 | |
| CN | 110066679 A | 7/2019 | |
| EP | 2021486 B1 | 2/2009 | |
| EP | 2123736 A1 | 11/2009 | |
| EP | 2285972 B1 | 2/2011 | |
| IN | 201717016875 A | 1/2017 | |
| IN | 201817001161 A | 1/2018 | |
| TW | 201712105 A | 4/2017 | |
| WO | WO2005037752 A1 | 4/2005 | |
| WO | WO2011008504 A2 | 1/2011 | |
| WO | WO2011128742 A1 | 10/2011 | |
| WO | WO2012106727 A1 | 8/2012 | |
| WO | WO2014154799 A1 | 10/2014 | |
| WO | WO2016007196 A1 | 1/2016 | |
| WO | WO2016061262 A1 | 4/2016 | |
| WO | WO2016201297 A1 | 12/2016 | |
| WO | WO2018071905 A1 | 4/2018 | |
| WO | WO2019084518 A1 | 5/2019 | |
| WO | WO2019215725 A1 | 11/2019 | |
| WO | WO2020093127 A1 | 5/2020 | |
| WO | WO2021087020 A1 | 5/2021 | |

OTHER PUBLICATIONS

Thushara Kandaramath Hari, Zahira Yaakob, Narayanan N. Binitha, "Aviation biofuel from renewable resources: Routes, opportunities and challenges", Nov. 18, 2014, Renewable and Sustainable Energy Reviews, https://www.sciencedirect.com/science/article/pii/S1364032114009204.
Scott Geleynseab, Zhihua Jiang, Kristin Brandt, Manuel Garcia-Perez, Michael Wolcott, Xiao Zhang, "Pulp mill integration with alcohol-to-jet conversion technology", May 2020 vol. 201, Fuel Processing Technology, https://www.sciencedirect.com/science/article/pii/S0378382019311403.
LanzaTech, "The LanzaTech process", 2017, LanzaTech Presentation (energy.gov), https://www.energy.gov/sites/prod/files/2017/07/f35/BETO_2017WTE-Workshop_SeanSimpson-LanzaTech.pdf.
Parthsarathi Trivedi, Hakan Olcay, Mark D. Staples, Mitch R. Withers, Robert Malina, Steven R.H. Barrett, "Energy return on investment for alternative jet fuels", Mar. 2015, vol. 141, Elsevier, Applied Energy, pp. 167-174, https://www.sciencedirect.com/science/article/pii/S0306261914012653.
Neil Savage, "The ideal biofuel", Jun. 23, 2011, vol. 474, Nature, pp. S9-S11, https://www.nature.com/articles/474S09a.
Gi Bo Han, Jung Hee Jang, Min Hwei Ahn and Byung Hun Jung, Aug. 26, 2019, IntechOpen, "Recent Application of Bio-Alcohol:

(56) References Cited

OTHER PUBLICATIONS

Bio-Jet Fuel", https://www.intechopen.com/books/alcohol-fuels-current-technologies-and-future-prospect/recent-application-of-bio-alcohol-bio-jet-fuel.

Danilo Silva Braz, Adriano Pinto Mariano, "Jet fuel production in eucalyptus pulp mills: Economics and carbon footprint of ethanol vs. butanol pathway", Jul. 22, 2018, Bioresource Technology, vol. 268 (2018), pp. 9-19 https://www.sciencedirect.com/science/article/abs/pii/S0960852418310319.

Manuel Antonio Diaz-Perez and Juan Carlos Serrano-Ruiz, "Catalytic Production of Jet Fuels from Biomass", Feb. 12, 2020, Molecules, 18 pages, https://www.mdpi.com/1420-3049/25/4/802/htm.

Robert A. Dagle et al., "Oligomerization of ethanol-derived propene and isobutene mixtures to transportation fuels: catalyst and process considerations", Catalysis Science & Technology, 2019, vol. 9, pp. 1117-1131, https://pubs.rsc.org/en/content/articlelanding/2019/cy/c8cy02297f/unauth#!divAbstract.

Clarissa P. Rodrigues, Priscila C. Zonetti, Camila G. Silva, Alexandre B. Gaspar, Lucia G. Appel, "Chemicals from ethanol—The acetone one-pot synthesis", Mar. 29, 2013, Elsevier, Applied Catalysis A: General 458 (2013) pp. 111-118.

Swedish Patent and Registration Office, Swedish Search Report dated Mar. 23, 2022 for Application 2151091-2, filed on Aug. 31, 2021, Applicant Swedish Biofuels AB, 3 pages (The present U.S. Appl. No. 18/574,254 claims priority to Swedish application 2151091-2).

European Patent Office, European Search Report dated Jan. 26, 2022 for Application 21194166.1, filed on Aug. 31, 2021, Applicant Swedish Biofuels AB, 8 pages (The present U.S. Appl. No. 18/574,254 claims priority to European application 21194166.1).

Swapnil Sarjerao Jagtap, "Assessment of feedstocks for blended alcohol-to-jet fuel manufacturing from standalone and distributed scheme for sustainable aviation", Aug. 19, 2019, American Institute of Aeronautics, AIAA Propulsion and Energy 2019 Forum.

Rongchun Shen, Ling Tao, and Bin Yang, "Techno-economic analysis of jet-fuel production from biorefinery waste lignin", Dec. 7, 2018, Wiley Online Library, www.wileyonlinelibrary.com, Biofules, Bioproducts & Biorefining, vol. 13, pp. 486-501 (2019).

Kristin L. Brandt, Robert J. Wooley, Scott C. Geleynse, Johnway Gao, Junyong Zhu, Ralph P. Cavalieri, and Michael P. Wolcott, "Impact of co-product selection on techno-economic analyses of alternative jet fuel produced with forest harvest residuals", May 18, 2029, Wiley Online Library, www.wileyonlinelibrary.com, Biofules, Bioproducts & Biorefining, vol. 14, pp. 764-775 (2020).

Sebastian Taco Vasquez, John Dunkleman, Swades K. Chaudhuri, Austin Bond, and Mark T. Holtzapple, "Biomass conversion to hydrocarbon fuels using the MixAlcoTM process at a pilot-plant scale", Jan. 31, 2014, Biomass and Bioenergy, vol. 62, pp. 138-148 (2014).

Nathaniel M. Eagan, Mrunmayi D. Kumbhalkar, J. Scott Buchanan, James A. Dumesic, and George W. Huber, "Chemistries and processes for the conversion of ethanol into middle-distillate fuels", Nature Reviews, vol. 3, Apr. 2019, pp. 223-249.

Mingli He, Meng Wang, Guanglu Tang, Yunming Fang, and Tianwei Tan, "From medium chain fatty alcohol to jet fuel: Rational integration of selective dehydration and hydro-processing", Applied Catalysis A, General 550 (2018), pp. 160-167.

Eric R. Sacia, Madhesan Balakrishnan, Matthew H. Deaner, Konstantinos A. Goulas, F. Dean Toste, and Alexis T. Bell, "Highly Selective Condensation of Biomass-Derived Methyl Ketones as a Source of Aviation Fuel", ChemSusChem, vol. 8 (2015), pp. 1726-1736.

Pazhamalai Anbarasan, Zachary C. Baer, Sanil Sreekumar, Elad Gross, Joseph B. Binder, Harvey W. Blanch, Douglas S. Clark, and F. Dean Toste, "Integration of chemical catalysis with extractive fermentation to produce fuels", Nature, vol. 491, Nov. 8, 2012, pp. 235-239.

K. P. Brooks, L.J. Snowden-Swan, S.B. Jones, M.G. Butcher, G.-S.J. Lee, D.M. Anderson, J.G. Frye, J.E. Holladay, J. Owen, L. Harmon, F. Burton, I. Palou-Rivera, J. Plaza, R. Handler and D. Shonnard, "Low-Carbon Aviation Fuel Through the Alcohol to Jet Pathway", The Science and Technology of Developing Biofuels for Aviation, Chapter 6, (2016), pp. 109-150.

Genkuo Nie, Xiangwen Zhang, Lun Pan, Ming Wang, and Ji-Jun Zou, "One-pot production of branched decalins as high-density jet fuel from monocyclic alkanes and alcohols", Chemical Engineering Science, vol. 180 (2018), pp. 64-69.

Feng Cheng, Catherine E. Brewer, "Producing jet fuel from biomass lignin: Potential pathways to alkylbenzenes and cycloalkanes", Renewable and Sustainble Energy Reviews, vol. 72 (2017), pp. 673-722.

Viet Pham, Mark Holtzapple, and Mahmoud El-Halwagi, "Techno-economic analysis of biomass to fuel conversion via the MixAlco process", J Ind Microbiol Biotechnol (2010) 37:1157-1168.

Scott Geleynse, Kristin Brandt, Manuel Garcia-Perez, Michael Wolcott, and Xiao Zhang, "The Alcohol-to-Jet Conversion Pathway for Drop-In Biofuels: Techno-Economic Evaluation", ChemSusChem, vol. 11 (2018), pp. 3728-3741.

Yu-Kai Chen, Cheng-Han Lin, and Wei-Cheng Wang, "The conversion of biomass into renewable jet fuel", Energy 201 (2020) 117655, 9 pages.

Benjamin G. Harvey and Heather A.Meylemans, "The role of butanol in the development of sustainable fuel technologies", JChem Technol Biotechnol 2011; vol. 86, pp. 2-9.

* cited by examiner

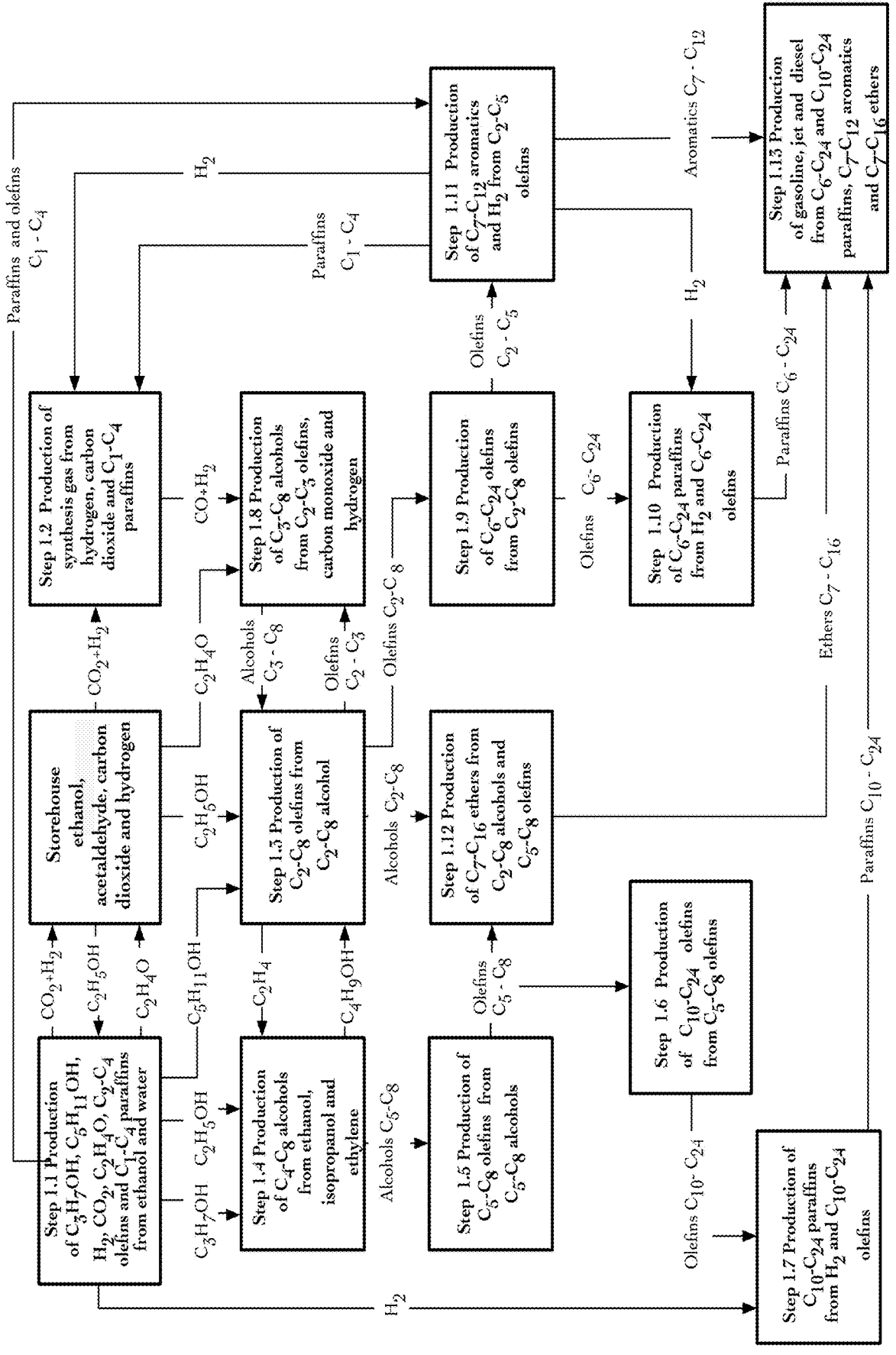

METHOD FOR PRODUCING MOTOR FUEL FROM ETHANOL

BACKGROUND

The present invention relates to a method for producing motor fuel, and more particularly gasoline, kerosene, and diesel, from ethanol obtained from a feedstock of mainly plant origin. In addition, intermediate products and by-products from the inventive motor fuel synthesis, that is; alcohols, aldehydes, ketones, ethers, olefins, paraffins and aromatic compounds obtained from feedstock of mainly plant origin, can be used not only in the chemical industry to produce paints or polymers, but also in the pharmaceutical industry, or for the manufacture of cosmetic products.

BACKGROUND OF THE RELATED ART

The rapid growth in the consumption of motor fuel, on the one hand resulting in a significant reduction of oil and gas reserves of our planet, and on the other hand, raising concerns of society regarding deterioration of the environment, stimulates the search for alternative motor fuels. The challenges facing modern industry concerning reducing carbon dioxide emissions to the atmosphere, stimulate research to improve existing methods and create new ones for the manufacture of motor fuel from renewable feedstocks. Currently, the most attractive raw material for the manufacture of alternative motor fuels is biomass, which is produced directly from the carbon dioxide constantly coming to the atmosphere. Recently, a significant number of works have appeared on the methods of processing biomass into motor fuel and, first of all, on the methods of producing kerosene from raw materials of biological origin.

U.S. Pat. No. 8,193,402 B2, U.S. Pat. No. 8,373,012 B2, and U.S. Pat. No. 8,487,149 B2 disclose microorganisms that, by means of fermentation, provide for conversion of carbohydrates isolated from plant biomass both into individual $C_2$-$C_6$ alcohols, and into a mixture of $C_2$-$C_6$ alcohols. The alcohols obtained, in turn, are dehydrated into the corresponding olefins. The $C_2$-$C_6$ olefins obtained both as individual olefins and as mixtures, are oligomerized, yielding $C_6$-$C_{21}$ olefins. Then, the $C_6$-$C_{21}$ olefins obtained are hydrogenated resulting in a product containing one or a few saturated $C_6$-$C_{21}$ alkanes.

WO 2018071905 and US2020010767 A1 disclose methods and materials for oligomerization of lower olefins, for example $C_2$-$C_8$ olefins, into transport fuels, including diesel and/or jet fuel. In some embodiments, tungsten zirconium catalysts are used to perform the oligomerization.

U.S. Pat. No. 10,633,320 B2 proposes a process for converting crude and/or refined fusel oil mixtures into renewable chemicals of a higher value by means of mixed oxide metal or zeolite catalysts. The patent discloses methods of directing a vaporized stream of crude and/or refined fusel oils through various mixed metal oxide catalysts, metal doped zeolites or non-metal doped zeolites, and/or metal oxides, obtaining products of higher value. The renewable chemicals produced using these catalysts include methyl isobutyl ketone (MIBK), diisobutyl ketone (DIBK), isoamylene, and isoprene.

US2011245542 A1 discloses synthesis of liquid fuels from oxygenated hydrocarbons. Processes and reactor systems for converting oxygen-containing hydrocarbons into hydrocarbons, ketones and alcohols used as liquid fuels such as gasoline, jet fuel or diesel fuel, and industrial chemicals are provided. The process comprises conversion of monooxygenated hydrocarbons such as alcohols, ketones, aldehydes, furans, carboxylic acids, diols, triols and/or other polyols to $C_{4+}$ hydrocarbons, alcohols and/or ketones by condensation. Oxidized hydrocarbons can originate from any source, but the preferred ones are those derived from biomass. The teaching of the patent differs in the way that there is a catalytic interaction of the oxygenate in the vapor phase with hydrogen in the presence of a basic condensation catalyst containing a component selected from the group consisting of Li, Na, K, Cs, B, Rb, Mg, Ca, Sr, Si, Ba, Al, Zn, Ce, La, Y, Sc, Y, Zr, Ti, hydrotalcite, phosphate, base treated aluminosilicate zeolite, zinc aluminate, base resin, base nitride, alloys or combinations thereof, at condensation temperatures ranging from about 80° C. to 500° C. and a condensation pressure of at least 0.1 atm, to obtain a $C_{4+}$ compound, where the $C_{4+}$ compound includes a member selected from the group consisting of $C_{4+}$ alcohol, $C_{4+}$ ketone, $C_{4+}$ alkane, $C_{4+}$ alkene, $C_{5+}$ cycloalkane, $C_{5+}$ cycloalkene, aryl, condensed aryl, and mixtures thereof.

Furthermore, US2012198760 A1 and U.S. Pat. No. 9,228, 134 B1 disclose a method and systems for producing distillate fuel from biomass. The invention disclosed therein provides methods, reactor systems and catalysts for converting biomass derived feedstock to $C_{8+}$ hydrocarbons using heterogeneous catalysts. The product stream can be separated and further processed for use in the chemical industry, or as a clean fuel, or as a mixing component for aviation and diesel fuels, or as heavy oils for lubricants and/or liquid fuels.

U.S. Pat. No. 9,771,533 B2 and U.S. Pat. No. 9,932,531 B2 disclose systems and processes for the conversion of ethylene feedstocks into hydrocarbon fuels. Systems, processes, and catalysts for producing fuels and fuel mixtures containing selected ratios of open and closed chain fuel range hydrocarbons suitable for the production of alternative fuels, including gasolines, jet fuels, and diesel fuels are disclosed. Fuel range hydrocarbons can be produced from feedstocks containing ethylene and ethanol.

US2020165176 A1 discloses a method for converting ethanol into 1-butene and 2-butene in a single reactor. The document describes simplified processes for producing chemicals in demand, such as butenes, from feedstocks containing ethanol. In one set of embodiments, this is accomplished in one step where the gas phase ethanol feed is passed over an acidic metal oxide catalyst having a transition metal dispersion of at least 5% on a metal oxide support. The ethanol content in the feed mix can range from 10% to 100% of the feed, and where it is not related to food, the feed ethanol can contain water. The method for the production of butene from a feedstock containing ethanol in one stage is disclosed. The method includes the stage of passing the feedstock containing ethanol in the gas phase over a catalyst 4 wt. % Ag/4 wt. % $ZrO_2/SiO_2$-SBA-16 having a dispersion of the transition metal Ag of not less than 30%, at a temperature of 325° C., a pressure of 7 bar and a flow rate of 0.23 $h^{-1}$ in the presence of a hydrogen carrier for the direct formation of butenes, with a selectivity equal to or larger than 13% of ethanol, wherein a relatively weak hydrogenation ability of Ag and weakly acidic materials of the carrier provides for maintaining it unchanged.

US2013144094 A1, US2013219778 A1, and US2013237728 A1 disclose methods for direct conversion of oxygenates derived from biomass into hydrocarbons with a longer chain. The longer chain hydrocarbons are characterized by a higher content of naphthenes, which is very useful in distillate range fuels, or more specifically jet and diesel range fuels. Naphthenes help the biomass-derived hydrocarbons meet jet and diesel product specifications while really helping cold flow properties. One of the embodiments describes the hydrotreating processes providing for selective conversion of glycols into monoalcohols that can be blended as biofuels. The NiMo and CoMo catalysts are active in the reaction and the reaction conditions can also affect the selectivity of the monoalcohols. Oxygenate feedstocks derived from biomass are converted into a variety of fuels, including the hydrocarbons of gasoline, jet and diesel fuels. General methods are proposed including hydrolysis, dehydration, condensation, oligomerization, and hydrogenation.

US2015376511 A1 and US2016108323 A1 provide a method for producing jet fuel hydrocarbons from alcohols derived from cellulose and hemicellulose, such as pentanediol and hydroxymethyl tetrahydrofuran, which is also known as tetrahydrofurfuryl alcohol. Alcohols are spliced or dimerized using the Guerbet synthesis, in which longer chain organic molecules are formed using a heterogeneous alcohol condensation catalyst. Also disclosed is a method for converting molecules containing one or more functional groups of alcohol into larger molecules. Alcohols such as methanol, ethanol, propanol and hexanol, and diols/glycols such as propylene glycol and butanediol are fed to a supported metal catalyst, such as a noble metal or solid acid catalyst in the presence of hydrogen at elevated temperatures and pressures, yielding a mixture of hydrocarbon and oxygenate products.

U.S. Pat. No. 8,049,048 B2 discloses renewable engine fuels. The disclosure provides a renewable engine fuel derived completely from biomass sources. One of the embodiments discloses fully renewable motor fuel comprised of one or more low carbon ethers, one or more furans, pentosan derivatives, one or more aromatic hydrocarbons, one or more $C_4$-$C_{10}$ straight chain alkanes derivable from polysaccharides and one or more bio-oils. In addition, the fuel may contain triethanolamine. Such a lower octane renewable fuel may be utilized in, for example, automobile fuel, 100 LL aviation fuel, and turbine engines. These fully renewable ethanol fuels can have a wide range of octane numbers and energies and can be effectively used to replace 100 LL aviation fuel (known as AvGas), as well as high octane, rocket, diesel and gas turbine fuel. In another embodiment, there is provided a synthetic, high octane aviation fuel containing isopentane and mesitylene and a process of producing the same from a biomass.

CA 2800057 A1 and U.S. Pat. No. 8,852,296 B2 disclose renewable engine fuel and a method of producing the same. A non-petroleum, high octane fuel obtained from biomass sources and a method for its production are disclosed. The production method includes the reduction of the biomass feedstock to sugars, the fermentation of sugars using microorganisms or their mutagens to produce ethanol or acetic acid, the conversion of acetic acid or ethanol to acetone and the conversion of acetone to mesitylene and isopentane, the main components of the engine fuel. Trimerization of acetone can be carried out in the presence of a catalyst containing at least one metal selected from a group consisting of niobium, iron and manganese. The ethanol can be converted to mesitylene in a dehydration reaction in the presence of a catalyst of zinc oxide or calcium oxide, and unreacted ethanol and water separated from mesitylene by distillation. These fuels based on ethanol are renewable and may be formulated to have a wide range of octane values and energy and may effectively be used to replace 100LL aviation fuel (known as AvGas), as well as high octane, rocket, diesel, turbine engine fuels, as well as two-cycle, spark ignition engine fuels. Ethanol can be converted to mesitylene in a dehydration reaction in the presence of a zinc oxide or calcium oxide catalyst, and unreacted ethanol and water are separated from mesitylene by distillation. These ethanol fuels based on biomass are fully renewable, can have a wide range of octane numbers and energies, and can be effectively used to replace 100 LL aviation fuel (known as AvGas), as well as high octane, rocket, diesel, gas turbine fuel, and also fuel for two stroke, spark ignition engines.

U.S. Pat. No. 9,447,347 B2 teaches production of biofuels via hydrogenolysis condensation. The method disclosed comprises a providing a carbohydrate; reacting the carbohydrate directly with hydrogen in the presence of a hydrogenolysis catalyst to produce a reaction product comprising a polyol; and then processing at least a portion of the reaction product to form a fuel blend.

US2012156742 A1 teaches a process to produce biofuels from biomass. The document teaches a method to produce biofuels from biomass by contacting the biomass with an aqueous media to form an extracted biomass, separating at least a portion of an aqueous liquor from the extracted biomass thereby providing the aqueous liquor stream comprising soluble carbohydrates; contacting the aqueous liquor stream with a purification substrate effective for removing sulfur compounds and nitrogen compounds thereby producing a treated carbohydrate stream having less than 35% of the sulfur content and less than 35% of the nitrogen content of the untreated aqueous liquor feed, based on the untreated aqueous liquor stream, then contacting the treated carbohydrate stream with an aqueous phase reforming catalyst to form a plurality of oxygenated intermediates; and processing at least a portion of the oxygenated intermediates to form a liquid fuel.

U.S. Pat. No. 9,862,655 B2 discloses a method and systems for producing jet range hydrocarbons. Methods and systems for producing jet range hydrocarbons are disclosed. In an illustrative embodiment, a process for producing jet range hydrocarbons comprises the steps of combining a first stream of $C_4$ olefinic hydrocarbons and a second stream of $C_5$-$C_8$ olefinic hydrocarbons to produce a third stream of $C_4$-$C_8$ hydrocarbons, oligomerizing the third stream of $C_4$-$C_8$ olefinic hydrocarbons to produce a fourth stream of $C_4$-$C_{20}$ olefinic hydrocarbons and separating $C_5$-$C_8$ hydrocarbons from the fourth stream of $C_4$-$C_{20}$ olefinic hydrocarbons to produce a second stream of $C_5$-$C_8$ olefinic hydrocarbons and a fifth stream of olefinic hydrocarbons $C_9$-$C_{20}$. The method further includes the step of hydrogenating a fifth stream of $C_9$-$C_{20}$ olefinic hydrocarbons to produce a sixth stream of $C_9$-$C_{20}$ paraffinic hydrocarbons of the jet fuel range.

US2016312131 A1 and US2016312134 A1 provide a process for producing jet-range hydrocarbons. The disclosed therein for producing hydrocarbons suitable for jet fuel, includes passing a renewable olefin feedstock comprising $C_3$ to $C_8$ olefins to an oligomerization reactor containing a zeolite catalyst to produce an oligomerized effluent, separating the oligomerized effluent into at least a light stream, and a heavy olefin stream. At least a first portion of the heavy olefin stream is recycled to the oligomerization reactor to dilute the renewable olefin feedstock. A portion of the heavy olefin stream may be hydrogenated and separated to provide a hydrocarbon product suitable for jet fuel. Also disclosed are methods and systems for producing jet-range hydrocarbons. In an illustrative embodiment, a process for producing jet-range hydrocarbons includes the steps of combining a first stream containing $C_4$ olefinic hydrocarbons and a second stream containing $C_5$-$C_8$ olefinic hydrocarbons to produce a third stream containing $C_4$-$C_8$ hydrocarbons. A step for oligomerizing a third stream containing $C_4$-$C_8$ olefinic hydrocarbons to produce a fourth stream containing $C_4$-$C_{20}$ olefinic hydrocarbons. $C_5$-$C_8$ hydrocarbons separated from the fourth stream containing $C_4$-$C_{20}$ olefinic hydrocarbons, are sent to the second stream, obtaining a fifth stream containing olefinic hydrocarbons $C_9$-$C_{20}$. The method further includes the step of hydrogenating a fifth stream containing $C_9$-$C_{20}$ olefinic hydrocarbons to obtain a sixth stream containing $C_9$-$C_{20}$ paraffinic hydrocarbons in the jet fuel range.

US2010146843 A1 and US2011126448 A1 disclose a process, plant, and biofuel for integrated biofuel production. This invention relates to a process, a plant, and a biofuel for integrated biofuel production, such as with butanol, biodiesel, and sugar products. The integrated process includes the step of removing hexose from a feedstock to form a lignocellulosic material. The process also includes the step of converting the hexose to butanol and/or a biodiesel fuel, and the step of depolymerizing lignocellulosic material to form pentose and a residue. The process also includes the step of converting the pentose to butanol and/or a biodiesel material. The process also includes the step of converting pentose to biogasoline and/or biodiesel fuel.

WO 2014154799 discloses production of middle distillate hydrocarbon composition. A process for the preparation of a middle distillate hydrocarbon composition from ethylene is claimed, wherein said process comprises the following steps: (a) feeding an ethylene composition in to an oligomerization reaction zone containing a supported nickel oligomerization catalyst to form an oligomerization product A, wherein the oligomerization reaction is operated at a temperature in the range of 30 to 300° C. and a pressure of at least 10 bar; (b) separating a light products stream B, a middle distillate product stream C and a heavy products stream D from oligomerization product A, wherein the light product stream B comprises the fraction of oligomerization product A, which boils in the $C_2$-$C_8$ mono-olefin boiling range and a middle distillate product stream C comprising a fraction of oligomerization product A, which boils above the boiling range of the light product stream B and below the boiling range of the heavy products stream D, and wherein the heavy product stream D comprises the fraction of oligomerization product A, which boils above the $C_{22}$ mono-olefin boiling range; (c) recycling a portion of the light products stream B to the oligomerization reaction zone of step (a) of the process; (d) feeding the heavy product stream D and a portion of the light products stream B in to an olefin metathesis reaction zone to produce a metathesis product stream E; (e) separating a middle distillate product F from the metathesis product stream E; and (f) hydrogenating the middle distillate product stream C, wherein the middle distillate hydrocarbon composition comprises at least a portion of the hydrogenated middle distillate product stream C and at least a portion of the middle distillate product F.

EP 2285972 A2 teaches a method for treating biomass by irradiation with an electron beam to obtain useful products, including fuel. Plant biomass, animal biomass and urban waste biomass exposed to electron beam irradiation are processed to produce useful products. Cellulosic and lignocellulosic materials, as well as materials containing starch or sugar, can be used as feedstock in the claimed method for processing biomass. The irradiated biomass is used to produce ethanol and butanol by fermentation.

WO 2019084518 A1 and US2019233751 A1 teach a method of preparing cellulosic ethanol having 100% biogenic carbon content as determined by ASTM 6866-18, which includes treating ground corn cobs with electron beam radiation and saccharifying the irradiated ground corn cob to produce sugars. The method also includes fermenting the sugars with a microorganism. The disclosures describe an unblended gasoline derived from cellulosic biomass with a research octane number higher than about 87 as determined by ASTM D2699. At the same time, it is indicated that the unblended gasoline is obtained as a result of catalytic treatment of ethanol obtained from cellulosic biomass. In addition, a jet fuel derived from cellulosic biomass comprising about 25% of aromatic hydrocarbons, about 2.5% of alkenes, about 41% of alkanes, and about 8.5% of oxygenated compounds (wt./wt.) is disclosed.

US2012271081 A1 discloses a method for the production of $C_{10+}$ hydrocarbons from heteroatomic organic compounds. The invention relates to a method for producing $C_{10+}$ hydrocarbons from heteroatomic organic compounds comprising at least one heteroatom chosen from oxygen, sulfur and halogen, alone or in combination. The method for producing a distillate from organic raw materials containing at least one heteroatom includes the first step of converting the starting organic compounds into olefins. At the second step of conversion, the olefins are oligomerized in the presence of at least 0.5% by weight of oxygen-containing compounds. By virtue of the presence of oxygenates during the oligomerization, this process makes it possible to improve the yield of distillate.

Furthermore, US2012271085 A1 teaches a method for producing a distillate from a hydrocarbon feed, comprising alcohol condensation. The invention relates to a method for oligomerizing $C_3$-$C_{10}$ olefins into a distillate containing $C_{10+}$ molecules. According to the disclosure, the oligomerization of $C_3$-$C_{10}$ olefins in the presence of at least one alcohol containing at least two carbon atoms provides for the production of $C_{10+}$ hydrocarbons.

U.S. Pat. No. 9,790,444 discloses methods to produce fuels. The disclosure generally relates to the production of fuels, and more specifically, to the catalytic conversion of alcohols into hydrocarbon ketones suitable for use as components in fuels. More specifically, the disclosure refers to the catalytic conversion of an isopropanol+butanol+ethanol (IBE) or acetone+butanol+ethanol (ABE) mixture to ketones suitable for use as a fuel. Blends of ABE or IBE can be obtained by fermentation of biomass or sugars. A method for producing a mixture of hydrocarbon ketones, comprising contacting acetone and at least two or more primary alcohols with a catalyst and, optionally, a base to obtain a mixture of hydrocarbon ketones, wherein the catalyst comprises:(i) one or more metals, and (ii) hydrotalcite (HT), lanthanum oxide ($La_2O_3$), titanium dioxide ($TiO_2$), or magnesium oxide (MgO), or any combination thereof.

U.S. Pat. No. 9,914,672 B2 teaches a method for converting alcohols to distillate fuels. A process for the production of jet and other heavy fuels from alcohols and mixture of alcohols is disclosed. The process may include contacting in a reaction zone at least one $C_2$ to $C_{11}$ alcohol with a solid catalyst having activity for the simultaneous dehydration of the alcohols to form olefins, isomerization of the olefins to form internal olefins, and oligomerization of the olefins produced in situ via dehydration to form an effluent comprising mono-olefinic hydrocarbons. Preferably, the alcohol feed is a mixture of alcohols, such as $C_2$ to $C_7$ alcohols or $C_4$ and $C_6$ alcohols, enabling the production of a mixture of branched hydrocarbons that may be used directly as a jet fuel without blending. The disclosed method for the production of jet and other heavy fuel comprises:(i) in the reaction zone, bringing a mixture of two or more alcohols from $C_2$ to $C_{11}$, including at least one secondary alcohol, into contact with a solid catalyst having activity for dehydrating alcohols to yield olefins and water; (ii) oligomerization of olefins obtained in situ from the dehydration reaction; and (iii) isomerization of the resulting olefin oligomers and olefins to yield internal olefins, to obtain monoolefin hydrocarbons. In addition, it is taught that $C_2$ to $C_{11}$ alcohols are obtained by biomass fermentation or biomass gasification to synthesis gas followed by a modified Fischer-Tropsch synthesis.

U.S. Pat. No. 9,688,590 B2 teaches production of jet and other heavy fuels from isobutanol.

U.S. Pat. No. 8,329,970 B2 teaches a method for the deoxygenation of materials of biological origin. The disclosure relates to a method for the deoxygenation of materials of biological origin and particularly to the removal of oxygen from organic compounds derived from biomass with carbon monoxide, to yield linear and branched hydrocarbons suitable as biofuels or as blending stocks or components for biofuels, such as gas, gasoline, diesel fuel and aviation fuel, as well as solvents. The method comprises contacting a feedstock with carbon monoxide in the presence of a catalyst comprising a metal selected from a group consisting of ruthenium, manganese, rhodium, rhenium, osmium, iridium, molybdenum, copper, zinc, palladium, platinum and cobalt, in the presence of water, under alkaline conditions at a temperature from 150 to 350° C. and under a pressure from 0.1 to 150 bar, to produce hydrocarbons.

WO 2020093127 A1 teaches a process for producing a renewable isoparaffin compound, and use of the renewable isoparaffin compound. The claimed invention relates to a process for producing a renewable isoparaffin compound with a high octane rating, comprising a step of Guerbet reaction between an initial $C_5$ alcohol load, obtained from renewable raw material, and methanol to produce a branched renewable $C_6$ alcohol; dehydration of the branched renewable $C_6$ alcohol into a $C_6$ olefin; and hydrogenation of the $C_6$ olefin into renewable isoparaffin. A renewable isoparaffin compound with a high octane rating, comprising at least 50% carbon of renewable natural origin in its composition, and use of said renewable paraffin in gasolines in general and in special high-performance gasolines, such as aviation gasoline, are also described.

Besides the above-mentioned disclosures, the following documents mentioned below have relevance to the claimed invention.

There is a number of patent disclosures dealing with hydroformylation of light olefins, including ethylene and propylene.

GB 1086100 teaches a method for producing aldehydes by olefin hydroformylation: ethylene or propylene is reacted with a mixture of carbon monoxide and hydrogen, as well as an inert gas, in the presence of catalysts containing cobalt at a pressure not exceeding 20 MPa and a temperature of 135° C. The hydrogen content in the total amount of gas in the reactor is 30 to 45 mol. %, and the inert gas is 5 to 15 mol. %. Methane, ethane or nitrogen can be used as the inert gas. In the disclosed hydroformylation process, standard cobalt-containing hydroformylation catalysts such as cobalt acetate, cobalt oxide, cobalt naphthenate, cobalt formate, cobalt carbonyl or hydrocarbonyl, cobalt oleate and cobalt carbonate can be used.

JP 2006160746 discloses a method of hydroformylation, characterized by the addition of an aldehyde to the synthesis stage. The implementation of hydroformylation using an unmodified cobalt complex for a catalyst, as well as the presence of aldehydes in the feedstock, increases the selectivity of the formation of the target product in the range from 0.5 to 20 mol %. The method relates to the hydroformylation of olefins having from 7 to 25 carbon atoms.

CN 1168129 discloses a method providing for hydroformylation of a hydrocarbon stream comprising a stream containing 27.5 to 75 wt. % ethylene and a total content of olefin up to 80 wt. % based on the total hydrocarbon content. Then, in the presence of a rhodium-containing catalyst, it is contacted with synthesis gas, and the hydroformylation product is recovered. The catalyst was prepared in a 500 ml autoclave equipped with a continuous gas supply system with back pressure control. 201 g of tetraglyme, 15.6 g of triphenylphosphine and 0.70 mg of rhodium were mixed under nitrogen. The catalyst solution was transferred to the autoclave under nitrogen, and the autoclave was purged with nitrogen, and then the gas stream was introduced into the boiler as indicated in Table 1. Then the pressure was set to 1000 kPa (absolute pressure) and the back pressure control was turned on, after which the autoclave and its contents were heated up to 100° C. At a catalyst content of 85 ppm, the conversion of olefins in the hydroformylation reaction reached 65%.

CN 101768062 A teaches a hydroformylation process using a water-soluble complex based on rhodium phosphine. The process is carried out in a static mixing reactor and involves the simultaneous formation of propanal and butanal. The invention is a continuous process, the aqueous catalyst solution is recirculated by a pump, the space velocity of the aqueous catalyst solution in the static mixing reactor is from 0.2 to 1.2 m/s. The residence time of the reaction liquid in the circulation tank is 10-20 seconds. The molar ratio of olefin to hydrogen gas and carbon monoxide in the feed mixture is from 1:(1.0-1.1):(1.0-1.1). The reaction pressure of the hydroformylation is from 1.4 MPa to 2.5 MPa, and the reaction temperature is 70 to 110° C. Since hydroformylation is a strongly exothermic reaction, heat removal from the reactor is expected. The degree of olefin conversion according to the claimed hydroformylation method is 96.2%, and the selectivity is 95%.

CN 102115433 discloses a method for the synthesis of propanal on a catalyst that is rhodium triphenylphosphine. In this catalyst, the rhodium concentration was 100 ppm and the triphenylphosphine concentration was 2.0%. The synthesis of propanal was carried out at a pressure of 1.5 MPa and a temperature of 80° C. The yield of propanal reached 99.6%.

RU 2354642 C2 teaches a method of hydroformylation of $C_2$-$C_{20}$ olefins, characterized by olefins being hydroformylated in the presence of a catalytic system containing rhodium, a polyphosphite ligand and a promoting ligand containing phosphorus. General formulas of polyphosphite ligand and the promoting ligand are given.

RU 2561171 C1 discloses a method of continuous, two-stage hydroformylation of $C_3$-$C_4$ olefins and a process unit for producing $C_4$-$C_5$ aldehydes. Hydroformylation of olefins is carried out using a recirculating catalyst solution containing a rhodium complex, organophosphorus ligands, product aldehydes, and heavy by-products.

Moreover, RU 2585285 C1 teaches a method for continuous hydroformylation of $C_2$-$C_8$ olefins using nanofiltration separation of heavy products from a recirculating catalyst solution containing a rhodium complex with a phosphite ligand. The disclosed method makes it possible to reduce the loss of the catalytically active rhodium complex and organophosphorus ligand when removing heavy condensation products of aldehydes.

Also, RU 2602239 C1 teaches a method of $C_6$-$C_9$ olefin hydroformylation into $C_7$-$C_{10}$ alcohols. Hydroformylation of $C_6$-$C_9$ olefins uses a catalytic system, consisting of a cobalt compound at a concentration of 0.15 to 0.40 wt. % and organophosphorus ligand, which is a triphenylphosphine in a molar ratio to cobalt in the range of 1 to 1.2. The alcohols are produced at a temperature of 170 to 190° C. and a synthesis gas pressure of 5 to 10 MPa. The conversion of $C_6$-$C_9$ olefins is up to 99%, and the yield of $C_7$-$C_{10}$ alcohols is at least 90%.

RU 2051734 C1 discloses a catalyst for the conversion of ethanol into acetone and carbon dioxide, using a catalyst containing zinc oxide (ZnO) 96.5-97.9% and cerium oxide ($CeO_2$) 2.1-3.42%.

RU 0002619951 teaches a two-stage method for propionic aldehyde production. The method includes the stage of carbon dioxide hydrogenation into synthesis gas in the presence of a catalyst containing metallic cobalt supported by organometallic framework structure. Metallic rhodium supported by a carrier was used as a catalyst for the hydroformylation. The process was carried out in a two-shelf flow-through reactor at a pressure of 20 to 40 atm by contacting a stationary layer of a catalyst containing cobalt, placed on the upper shelf of the reactor and heated to a temperature of 500° C., with a raw material mixture of $H_2$ and $CO_2$ at a volumetric flow rate of gas feed supply of 500-1000 $h^{-1}$. After that, the reaction gases obtained, heated to a temperature of 500-520° C., containing a mixture of $CO+H_2+CO_2$, were mixed with cold ethylene supplied to the inter-shelf space. The resulting gas mixture in a ratio of $CO:H_2:C_2H_4=1:(1\text{-}2):1$ was supplied to the lower shelf of the reactor at a temperature of 170 to 230° C. for interaction with the rhodium-containing catalyst placed there. The proposed method provides for increasing the selectivity of the target product formation up to 58.1%, and the yield up to 20.1%, ensuring the utilization of the greenhouse gas, $CO_2$.

It should be mentioned that the largest scale and most industrially developed method of processing biomass into alcohols is currently the process of ethanol production.

Ethanol is currently used in gasoline, both individually and in the form of ethers to increase the octane number. However, the wider use of ethanol in gasoline is limited by the oxygen content limit, which is regulated by the relevant standards.

At the same time, it is known that ethanol, as well as $C_3$-$C_5$ alcohols, can be obtained by biosynthesis and processed into a motor fuel free of oxygen, see e.g. "Conversions of mixtures of $C_2$-$C_8$ olefins to jet fuel and/or diesel fuel in high yield from bio-based alcohols" WO 2018071905 A1, US2020010767 A1. The method consists of the production of $C_8$-$C_{16}$ paraffins by processing $C_2$-$C_5$ alcohols obtained by fermentation of carbohydrates, extracted from biomass. The paraffins thus obtained can be used to produce motor fuel. The method demonstrates the possibility of obtaining hydrocarbons that can be used as components of motor fuel. Moreover, said method directly indicates the need to use $C_2$-$C_5$ alcohols obtained from biomass in the production of motor fuel. Also, the document proposes to use the oligomerization of $C_2$-$C_8$ olefins to obtain higher olefins $C_{12}$-$C_{16}$. Also, said document proposes to use the hydrogenation of $C_8$-$C_{16}$ olefins to obtain $C_8$-$C_{16}$ paraffins.

BRIEF SUMMARY

Some embodiments provide a method for producing from ethanol a motor fuel selected from gasoline, kerosene, and diesel, is provided, which method comprises the following interconnected steps:

step 1.1 converting a mixture of ethanol and water into: isopropanol and $C_5$ alcohols; acetaldehyde; a mixture of $C_1$-$C_4$ paraffins and $C_2$-$C_4$ olefins; a mixture of carbon dioxide and hydrogen;

step 1.2 converting the mixture of carbon dioxide and hydrogen, obtained in step 1.1, additional hydrogen, and a mixture of $C_1$-$C_4$ paraffins into synthesis gas;

step 1.3 converting ethanol, and $C_3$-$C_8$ alcohols, including $C_5$ alcohols obtained from step 1.1, into: $C_2$-$C_8$ olefins, including ethylene and propylene;

step 1.4 converting a mixture of unreacted ethanol from step 1.1, isopropanol obtained in step 1.1, ethylene obtained in step 1.3, using a telomerization reaction into secondary butanol and tertiary $C_5$-$C_8$ alcohols, the tertiary $C_8$ and $C_7$ alcohols being obtained from the isopropanol, and the tertiary $C_6$, and $C_8$ alcohols being obtained from the ethanol, wherein the resulting secondary butanol is directed to step 1.3;

step 1.5 converting the $C_5$-$C_8$ tertiary alcohols, obtained in step 1.4, by dehydration into $C_5$-$C_8$ olefins;

step 1.6 converting a first portion of the $C_5$-$C_8$ olefins, obtained in step 1.5, by oligomerization into $C_{10}$-$C_{24}$ olefins;

step 1.7 converting the $C_{10}$-$C_{24}$ olefins, obtained in step 1.6, by hydrogenation using hydrogen obtained from step 1.1, into $C_{10}$-$C_{24}$ paraffins;

step 1.8 converting the synthesis gas, obtained in step 1.2, ethylene obtained in step 1.3, propylene obtained in step 1.3, and the acetaldehyde, obtained in step 1.1, by hydroformylation and aldol condensation into a mixture of $C_3$-$C_4$ aldehydes and $C_5$-$C_8$ aldols, said mixture of $C_3$-$C_4$ aldehydes and $C_5$-$C_8$ aldols is thereafter hydrogenated to obtain $C_3$-$C_8$ alcohols, which alcohols are directed to step 1.3 to obtain $C_3$-$C_8$ olefins, wherein the acetaldehyde produces $C_5$ alcohol, the ethylene from step 1.3 produces $C_3$ and $C_6$ alcohols, and the propylene from step 1.3 produces $C_4$ and $C_8$ alcohols; and wherein the ethylene and the propylene from step 1.3 produce $C_7$ alcohol;

step 1.9 converting the $C_2$-$C_8$ olefins from step 1.3, by oligomerization into $C_6$-$C_{24}$ olefins;

step 1.10 converting the $C_6$-$C_{24}$ olefins, obtained in step 1.9, and hydrogen, by hydrogenation into $C_6$-$C_{24}$ paraffins;

step 1.11 converting unreacted $C_2$-$C_5$ olefins from step 1.9, and the mixture of $C_2$-$C_4$ olefins and $C_1$-$C_4$ paraffins, obtained in step 1.1, by aromatization into $C_7$-$C_{12}$ aromatic hydrocarbons, hydrogen, and a mixture of $C_1$-$C_4$ paraffins, wherein a first portion of the hydrogen produced is directed to step 1.10, and the remaining second portion of the hydrogen produced and the $C_1$-$C_4$ paraffins mixture are directed to step 1.2;

step 1.12 converting the remaining second portion of the mixture of $C_5$-$C_8$ olefins, obtained in step 1.5, and a portion of $C_2$-$C_8$ alcohols from step 1.3, into $C_7$-$C_{16}$ ethers; and, step 1.13 converting the $C_{10}$-$C_{24}$ paraffins, obtained in step 1.7, and the $C_6$-$C_{24}$ paraffins, obtained in step 1.10, into $C_6$-$C_{10}$ gasoline, $C_{11}$-$C_{18}$ kerosene, and $C_{19}$-$C_{24}$ diesel fractions of a motor fuel; converting the $C_7$-$C_{12}$ aromatic hydrocarbons, obtained in step 1.11, into $C_7$-$C_8$ gasoline and $C_9$-$C_{12}$ kerosene fractions of a motor fuel; and converting the $C_7$-$C_{16}$ ethers, obtained in step 1.12, into $C_7$-$C_{10}$ gasoline and $C_{11}$-$C_{16}$ diesel fractions of a motor fuel, and also mixing selected fractions thereof, into a motor fuel selected from gasoline, kerosene, and diesel.

A method for producing motor fuel from ethanol has been developed by the present inventor, wherein the technological process of ethanol conversion into motor fuel is carried out as follows:

Ethanol is converted into $C_3$-$C_8$ alcohols by two different routes.

In one of the routes, a mixture of ethanol and water at 500-515° C. is contacted with a heterogeneous catalyst consisting of the following metal oxides: ZnO 60 to 63% mass; $CeO_2$ 1 to 6% mass; MgO 12 to 18% mass; $Al_2O_3$ 13 to 23% mass, with the proportions calculated in terms of metal oxide, yielding a liquid reaction medium, comprised mainly by water and acetone, as well as acetaldehyde and diethylketone. Furthermore, a gaseous reaction medium is obtained, comprised mainly by carbon dioxide and hydrogen, as well as $C_2$-$C_4$ olefins and $C_1$-$C_4$ paraffins. The acetone and diethylketone are then hydrogenated to yield isopropanol and 3 pentanol alcohol. Acetaldehyde is then used in aldol condensation with propanal to obtain 2-methylbutenal, which is the hydrogenated into 2 methyl butyl alcohol. A mixture of $C_2$-$C_4$ olefins and $C_1$-$C_4$ paraffins is used in the process of aromatization to obtain aromatic compounds. Carbon dioxide and hydrogen are converted into synthesis gas in the presence of Cu or Ni catalysts.

After that, ethanol and isopropanol in the presence of ditretamyl peroxide interact with ethylene to form sec-butanol, as well as tertiary $C_5$-$C_8$ alcohols.

In another route, $C_3$-$C_8$ alcohols are obtained by hydroformylation of ethylene or propylene, obtained by dehydration of ethanol or propanol in the presence of a gamma $Al_2O_3$ catalyst, by synthesis gas produced from carbon dioxide and hydrogen. Hydroformylation of ethylene or propylene is carried out in a heterogeneous reaction medium using a water-soluble Rhodium catalyst. In this case, the concentration of Rhodium in the aqueous phase is from 30 to 50 ppm. Triphenylphosphine-sulfonic acid sodium salts are used as a ligand: from triphenylphosphine-3-sulfonic acid sodium salt to triphenylphosphine-3,3',3"-trisulfonic acid trisodium salt. The process of obtaining propionic or butyl aldehydes is carried out at a temperature of 45 to 90° C. and a pressure of 1.0 to 3.0 MPa. The obtained acetaldehyde, propionic and n-butyl aldehydes are treated by cross aldol condensation in the presence of a heterogeneous granular catalyst, containing at least 93% ZSM-5 modified by 3.5 to 7.0% Zn at a temperature of 100 to 150° C. and a pressure of 0.5 to 1.0 MPa. The resulting mixture of aldehydes and $C_3$-$C_8$ aldols is then hydrogenated to yield $C_3$-$C_8$ alcohols.

Moreover, it was found that the hydroformylation of ethylene or propylene obtained in the dehydration of ethanol or propanol by synthesis gas produced from carbon dioxide and hydrogen can be performed in a heterogeneous reaction medium using a water-soluble cobalt catalyst. When using a cobalt catalyst, the concentration of the metal in the aqueous phase is from 0.1% to 1.0%. In this case, triphenylphosphine-sulfonic acid sodium salts are used as a ligand: from triphenylphosphine-3-sulfonic acid sodium salt to triphenylphosphine-3,3',3"-trisulfonic acid trisodium salt. Hydroformylation of ethylene or propylene is carried out at a temperature of 120 to 145° C. and a pressure of 3.0 to 5.0 MPa. It was demonstrated, that besides formation of the propionic or butyl aldehydes, the condensation of said aldehydes occurs in the reaction medium to yield 2-methyl pentenal or 2-ethylhexenal. Hydrogenation of the resulting aldehyde and aldol mixtures provides for producing $C_3$-$C_8$ alcohol mixtures.

$C_2$-$C_8$ olefins obtained by dehydration of primary and secondary $C_2$-$C_8$ alcohols are oligomerized in the presence of a heterogeneous catalyst, containing at least 93% ZSM-5 modified by 3.5 to 7.0% Zn, or in the presence of a heterogeneous catalyst containing at least 95% ZSM-5 modified by 3.5 to 5.0% Zn and 0.1 to 1.5% Ce, at a temperature of 250-350° C. and a pressure of 2.0-5.0 MPa to obtain $C_6$-$C_{24}$ olefins. The unreacted $C_2$-$C_5$ olefins from the oligomerization reaction are used as a raw material for producing aromatic $C_7$-$C_{12}$ compounds in the presence of a heterogeneous catalyst, containing at least 93% ZSM-5 modified by 3.5 to 7.0% Zn at a temperature of 350 to 450° C. and a pressure of 0.5 to 5.0 MPa.

$C_5$-$C_8$ olefins, obtained by dehydration of tertiary $C_5$-$C_8$ alcohols, are oligomerized in the presence of a heterogeneous catalyst, which is an ion exchange resin in the form of a cation exchanger, for example Amberlite 15, at a temperature of 70-120° C. and a pressure of 1.0 to 2.0 MPa to yield $C_{10}$-$C_{24}$ olefins. The unreacted $C_5$-$C_8$ olefins from the oligomerization reaction and a proportional part of the primary and secondary $C_5$-$C_8$ alcohols are used as a source material for producing $C_7$-$C_{16}$ ethers in the presence of an ion-exchange resin in the form of, for example, a cation exchanger, Amberlite 15, at a temperature of 70 to 120° C. and a pressure of 1.0 to 2.0 MPa.

$C_6$-$C_{24}$ and $C_{10}$-$C_{24}$ olefins are hydrogenated in the presence of a heterogeneous catalyst, containing oxides NiO, CuO and $Cr_2O_3$ in a molar ratio of 1:1:1, at a temperature of 150 to 200° C. and a pressure of 4.5 to 5.0 MPa to obtain $C_6$-$C_{24}$ and $C_{10}$-$C_{24}$ paraffins. After that, $C_6$-$C_{24}$ and $C_{10}$-$C_{24}$ paraffins are directed to rectification to obtain $C_6$-$C_{10}$ gasoline, $C_{11}$-$C_{18}$ kerosene and $C_{19}$-$C_{24}$ diesel fractions. The isolated gasoline fraction of $C_6$-$C_{10}$ paraffins is blended with $C_7$-$C_{10}$ ethers and/or $C_7$-$C_8$ aromatic hydrocarbons to obtain gasoline complying with the current standard EN228, however, with a RON octane number of at least 100 and MON of at least 93. The separated kerosene fraction of $C_{11}$-$C_{18}$ paraffins is blended with $C_9$-$C_{12}$ aromatic hydrocarbons to obtain kerosene complying with the current standard for Jet A-1. The isolated diesel fraction of $C_{19}$-$C_{24}$ paraffins is blended with $C_1$-$C_{16}$ ethers to obtain diesel fuel complying with the current standards.

The method developed for producing motor fuel from ethanol, as well as the proposed schematic diagram of the technological process for converting ethanol, provide for establishing industrial production of environmentally friendly kerosene, as well as gasoline and diesel.

Tasks that may be solved by some embodiments are the following:

development of methods for converting ethyl alcohol into higher alcohols, including $C_3$-$C_8$ alcohols;

development of methods for producing $C_3$-$C_8$ alcohols, primarily branched alcohols;

improvement of the technology of $C_2$-$C_3$ olefin hydroformylation, including the goal of increasing the yield of $C_4$-$C_8$ branched aldehydes;

development of technology for lower olefin oligomerization into higher olefins, providing for producing fractions of higher branched olefins, with a linear molecule content of not higher than 5%, and free of aromatic and cyclic compounds;

development of methods for producing $C_6$-$C_{24}$ branched paraffins, in which the number of the various compounds is not less than 50 and preferably more than 100, and the content of linear molecules does not exceed 5%, and free of aromatic and cyclic compounds;

development of methods for producing $C_7$-$C_{16}$ ethers of branched structure;

development of production methods and compositions of gasoline with RON octane number of at least 95 and free of aromatic compounds;

development of production methods and compositions of kerosene hydrocarbon fractions of primarily branched structure, free from aromatic compounds;

development of production methods and compositions of kerosene, containing hydrocarbon fractions of mainly branched structure, and with aromatic compounds content in the range from 8% vol. to 25% vol.;

development of production methods of diesel and diesel compositions that do not contain aromatic compounds;

development of technology for the manufacture of gasoline, kerosene and diesel using raw materials of biological origin.

BRIEF DESCRIPTION OF THE SEVERAL VIEWS OF THE DRAWINGS

FIG. 1 is a diagram of an overall process.

DETAILED DESCRIPTION

FIG. 1 shows the inventive scheme developed for conversion of ethanol into motor fuels and, particularly, into kerosene.

The feedstock used for the inventive production of kerosene and other motor fuels is ethanol. Preferred ethanol of the inventive method for the motor fuel production is produced from wood or waste from humans and their activities. To increase the economic efficiency of our proposed method for converting ethanol into motor fuel, fusel oils can be used as an additional raw material along with carbon dioxide and methane obtained in the production of ethanol. Also, according to the invention, it is recommended to use electricity obtained from environmentally friendly sources and wastes of plant biomass as the energy resource for the method of the present invention of converting ethanol into motor fuel.

It is known in the prior art, that acetone can be obtained from ethyl alcohol with a high yield, that is, 95% of theoretical yield. The vapors of ethyl alcohol mixed with steam are directed at 400-425° C. through the catalyst containing 54% of iron and chromium oxides, 8% of copper oxide and 38% of calcium carbonate. The total reaction is described by the equation:

$$2C_2H_5OH + H_2O \text{ catalysis, } t° \rightarrow CH_3\text{---}CO\text{---}CH_3 + CO_2\uparrow + 4H_2\uparrow$$

As disclosed in one of the prior art references above, RU 2051734 $C_1$, acetone is nearly the only liquid product of the reaction in the presence of catalyst consisting of ZnO, 96.5 to 97.9%, and $CeO_2$, 2.1 to 3.42%.

At step 1.1 of the inventive method for producing motor fuel, an aqueous solution of ethanol is converted into a mixture of acetone, acetaldehyde, diethylketone and $C_3$-$C_5$ alcohols in the presence of a specially designed catalyst at a temperature of 500 to 515° C. and a pressure of 0.9 to 1.1 MPa. The composition of the catalyst is as follows: ZnO, 60 to 63% mass; $CeO_2$, 1 to 6% mass; MgO, 12 to 18% mass; $Al_2O_3$, 13 to 23% mass. Furthermore, part of the ethanol is converted, under these conditions, into carbon dioxide, hydrogen and a mixture of $C_2$-$C_4$ olefins and $C_1$-$C_4$ paraffins.

Conversion of ethanol into a mixture of the products above, in the presence of the catalyst used, is unexpected and opens up new possibilities for the production of hydrocarbons that can be used in kerosene.

In a preferred embodiment of the inventive method, a mixture of ethanol and water, the content of which is from 25% to 35% of the total volume of the mixture, contacts at a pressure of 0.5-1.5 MPa and a temperature of 500-515° C. with a heterogeneous catalyst consisting of the following metal oxides; ZnO 60-63% mass., $CeO_2$ 1-6% mass., MgO 12-18% mass., $Al_2O_3$ 13-23% mass., with the proportions calculated in terms of metal oxide, wherein a mixture of ethanol with water is supplied to the catalyst at a rate of 0.5-0.9 liters per 1 liter of catalyst per hour. Acetone and diethyl ketone, obtained in the process, are isolated from the reaction mixture, hydrogenated at a temperature of 100-150° C. and a pressure of 0.5-0.9 MPa in the presence of catalyst containing oxides CuO and $Cr_2O_3$ in a molar ratio of 1:1 by hydrogen, which is also obtained from a mixture of ethanol and water. This yields isopropanol and 3-pentanol. A mixture of $C_3$-$C_5$ alcohols is used for producing the corresponding olefins by dehydration in the presence of catalyst, gamma $Al_2O_3$. Isopropanol, isolated from the reaction medium, is used to obtain tertiary alcohols $C_5$-$C_7$ and $C_7$+. Moreover, contacting the catalyst consisting of the following metal oxides: ZnO 60-63% mass., $CeO_2$ 1-6% mass., MgO 12-18% mass., $Al_2O_3$ 13-23% mass., with the proportions calculated in terms of metal oxide, with a mixture of ethanol and water yields acetaldehyde, which is isolated from the reaction medium and used in the aldol condensation with propanal to obtain 2-methyl butenal. The 2-methyl butenal is then hydrogenated to yield 2-methyl butanol. Particularly important for the inventive method is the possibility of converting a mixture of ethanol and water into carbon dioxide and hydrogen upon contact with the catalyst consisting of the following metal oxides: ZnO 60-63% mass., $CeO_2$ 1-6% mass., MgO 12-18% mass., $Al_2O_3$ 13-23% mass., with the proportions calculated in terms of metal oxide. In step 1.2 of the inventive method said carbon dioxide and hydrogen are converted into water and carbon monoxide in the presence of a catalyst containing 5-10% Cu supported by $Al_2O_3$, at a temperature of 550-600° C. and a pressure of P=1.0-5.0 MPa, or, using a catalyst containing oxides NiO, CuO and $Cr_2O_3$ in a molar ratio 1:1:1, are converted at a temperature of 900-1000° C. and a pressure of P=0.1-0.5 MPa into a mixture of carbon monoxide and hydrogen. The carbon monoxide and hydrogen are used in step 1.2 of the inventive process to produce synthesis gas.

Dehydration of ethanol is carried out at the step 1.3 of the inventive method for olefin production in the presence of a gamma $Al_2O_3$ catalyst in a continuous flow reactor at 350 to 450° C. and a pressure of 0.5 to 3.5 MPa.

Ethylene and water are formed in the dehydration reactor. The reaction mixture from the dehydration reactor enters the rectification column, where ethylene is separated from the obtained water. Water is directed to the production of an aqueous solution of ethanol in the process of acetone production.

Ethylene obtained by dehydration of ethanol is directed to step 1.4 of the inventive process for performing the reaction of telomerization or to step 1.8 of the inventive process for performing the reaction of hydroformylation.

Propylene, obtained by dehydration of n-propanol or isopropanol, is directed to step 1.8 of the inventive method to perform the reaction of hydroformylation. $C_3$-$C_8$ alcohols obtained in the inventive method for producing motor fuel, are processed at step 1.3 of the inventive method into the corresponding olefins $C_3$-$C_8$ in a similar way by using gamma $Al_2O_3$ as a catalyst. The $C_2$-$C_8$ olefins obtained at step 1.3 of the inventive method are sent to step 1.9 of the inventive method to carry out the reaction of oligomerization into $C_6$-$C_{24}$ olefins.

Hydroformylation of ethylene, obtained from the dehydration of ethanol at step 1.3 of the inventive method, is carried out at step 1.8 of the inventive method in the presence of either a rhodium or cobalt catalyst. The process of ethylene hydroformylation is carried out in a heterogeneous reaction medium using a water-soluble catalyst. When using a rhodium catalyst, the concentration of the metal with respect to the liquid phase is between 30 and 50 ppm. In this case, triphenylphosphine-sulfonic acid sodium salts are used as a ligand: from triphenylphosphine-3-sulfonic acid sodium salt to triphenylphosphine-3,3',3"-trisulfonic acid trisodium salt in a ratio of 30:1 to metallic rhodium. The process is carried out in the reactor with a stirring device at a temperature of 45 to 90° C. and a pressure of 1.0 to 3.0 MPa. The molar ratio of the source gases $C_2H_4$:CO:$H_2$=(1 to 1.1): 1:1 is maintained by flow meters.

In a preferred embodiment of the inventive method, in order to reduce catalyst losses, the organic phase, obtained in the process of ethylene hydroformylation, is separated from the aqueous phase, containing dissolved Rh catalysis, using a highly efficient centrifugal separator.

The resulting reaction mass enters a highly efficient centrifugal separator, where it is separated into three phases: a gas phase containing unreacted ethylene, carbon monoxide and hydrogen, a liquid organic phase containing mainly propanal and a liquid aqueous phase containing a water-soluble rhodium catalyst. The gas phase and the liquid aqueous phase are returned to the hydroformylation reactor by the metering devices.

The liquid organic phase, consisting mainly of propanal, is directed to the reactor filled with a granular catalyst containing at least 93% of ZSM-5 zeolite modified by 3.5 to 7.0% Zn, or a granular catalyst containing at least 95% of ZSM-5 zeolite modified by 3.5 to 5.0% Zn and 0.1-1.5% Ce, where the propanal is converted into 2-methyl-pentenal at a temperature of 100 to 150° C. and a pressure of 0.5 to 1.0 MPa.

The liquid organic phase, containing mainly 2-methyl-pentenal as well as propanal, is sent to the reactor filled with a granular catalyst comprising NiO, CuO and $Cr_2O_3$ oxides in a molar ratio of 1:1:1, where 2-methyl-pentenal and propanal are at a temperature of 150 to 200° C. and a pressure of 4.5 to 5.0 MPa converted into 2-methyl-pentanol and propanol.

Further, the propanal, obtained by hydroformylation, is mixed with acetaldehyde, which is obtained by the inventive process for ethanol conversion into acetone, and is used to produce 2-methyl-butenal. For this, the mixture of acetaldehyde and propanal, in a molar ratio of 1:1, is directed to a reactor filled with a granular catalyst, containing at least 93% of ZSM-5 zeolite modified by 3.5 to 7.0% Zn, or a granular catalyst containing at least 95% of ZSM-5 zeolite modified by 3.5 to 5.0% Zn and 0.1 to 1.5% Ce, where the mixture of source aldehydes is at a temperature of 100 to 150° C. and a pressure of 0.5 to 1.0 MPa converted into 2-methyl-butenal. The reaction mass containing 2-methyl-butenal is directed to the reactor filled with a granular catalyst consisting of the oxides NiO, CuO and $Cr_2O_3$ in a molar ratio of 1:1:1, where 2-methyl-butenal is converted into 2-methyl-butanol at a temperature of 100 to 200° C. and a pressure of 5.0 to 9.0 MPa.

Hydroformylation of propylene, obtained in step 1.3 of the inventive method by dehydration of n-propanol or isopropanol in the presence of a rhodium catalyst is preferably performed as follows. Propanol, obtained by hydrogenation of propanal, or isopropanol, obtained by hydrogenation of acetone, are dehydrated. The dehydration of propyl alcohols is carried out using a heterogeneous gamma $Al_2O_3$ catalyst at a temperature of 350 to 450° C. and a pressure of 0.1 to 1.0 MPa. Propylene, obtained by dehydration of propyl or isopropyl alcohols, is separated from water and sent to hydroformylation.

Hydroformylation of propylene is carried out in a heterogeneous reaction medium using a water-soluble rhodium catalyst. When a rhodium catalyst is used for propylene hydroformylation the metal concentration with respect to the liquid phase is from 30 to 50 ppm. In this case, triphenylphosphine-sulfonic acid sodium salts are used as a ligand: from triphenylphosphine-3-sulfonic acid sodium salt to triphenylphosphine-3,3',3"-trisulfonic acid trisodium salt in a ratio of 30:1 with metallic rhodium. The process is performed in the reactor with a stirring device at a temperature of 70 to 90° C. and a pressure of 3.0 to 5.0 MPa. The ratio of the source gases in moles $C_3H_6$:CO:$H_2$=(1-1.1): 1:1 is maintained by flow meters.

To increase the rate of the propylene hydroformylation reaction and to increase the yield of isobutanal, $C_2$-$C_3$ alcohols are added to the water-soluble Rh catalyst in the volume ratio $H_2O$: ($C_2$-$C_3$)=(0.95-0.65):(0.05-0.35).

Additionally, in order to reduce catalyst losses, the organic phase obtained in the hydroformylation of propylene is separated from the aqueous phase, containing dissolved Rh catalyst, using a highly efficient centrifugal separator.

The resulting reaction mass is directed to a highly efficient centrifugal separator to separate the reaction mass into three phases:(i) a gas phase containing unreacted propylene, carbon monoxide and hydrogen, (ii) a liquid organic phase containing mainly butanals and (iii) a liquid aqueous phase containing a water-soluble rhodium catalyst. The gas phase and the liquid aqueous phase are returned to the hydroformylation reactor by metering devices.

The liquid organic phase containing n-butanal and isobutanal in the weight ratio (2-3): 1 is transferred to the reactor filled with a granular catalyst, containing at least 93% of ZSM-5 zeolite modified by 3.5 to 7.0% Zn, or a granular catalyst containing at least 95% of ZSM-5 zeolite modified by 3.5 to 5.0% Zn and 0.1 to 1.5% Ce, where at a temperature of 100-150° C. and a pressure of 0.5-1.0 MPa, butanal is converted into 2-ethyl-hexenal.

The liquid organic phase, containing mainly 2-ethyl-hexenal, as well as isobutanal, is sent to a reactor filled with a granular catalyst consisting of the oxides NiO, CuO and $Cr_2O_3$ in a molar ratio of 1:1:1, where, at a temperature of 100 to 200° C. and a pressure of 5 to 10 MPa, 2-ethyl-hexenal and isobutanal are converted into 2-ethyl hexanol and isobutanol.

Moreover, the inventive method, in a preferred embodiment, provides for obtaining $C_5$-$C_8$ alcohols by cross-aldol condensation of n-butanal, acetaldehyde and propanal in the presence of a heterogeneous catalyst containing at least 93% of ZSM-5 zeolite modified by 3.5-7.0% Zn, or a granular catalyst containing at least 93% of ZSM-5 zeolite modified by 3.5-5.0% Zn and 0.1-1.5% Ce. The obtained 2-methyl-butenal, 2-methyl-pentenal, 2-methyl-hexenal and 2-ethyl-hexenal are then hydrogenated in the presence of a heterogeneous catalyst consisting of the oxides NiO, CuO and $Cr_2O_3$ in a molar ratio of 1:1:1 at a temperature of 150-200° C. and a pressure P=4.5-5.0 MPa to yield 2-methyl-butanol, 2-methyl-pentanol, 2-methyl hexanol and 2-ethyl-hexanol.

The fact that a water-soluble cobalt catalyst can be used for hydroformylation of lower $C_2$-$C_3$ olefins was unexpected. When using a cobalt catalyst, the concentration of the metal with respect to the liquid phase is between 0.1% and 1.0%. Triphenylphosphine-sulfonic acid sodium salts are used as a ligand: triphenylphosphine-3-sulfonic acid sodium salt to triphenylphosphine-3,3',3"-trisulfonic acid trisodium salt in a ratio (1-30): 1 to metallic cobalt. The hydroformylation of ethylene is carried out in a reactor with a stirring device at a temperature of 120 to 140° C. and a pressure of 3.0 to 5.0 MPa. The ratio of the source gases in moles:$C_2H_4$:CO:$H_2$ is from 1:1:1 to 1:1.5:2.5 and is maintained by flow meters.

In order to reduce catalyst losses, the organic phase formed during ethylene hydroformylation is separated from the aqueous phase, in which the Co catalyst is dissolved, using a highly efficient centrifugal separator. The resulting reaction mass is transferred to a highly efficient centrifugal separator for separation into three phases: a gas phase containing unreacted ethylene, carbon monoxide and hydrogen, a liquid organic phase containing mainly propanal, 2-methylpentenal, and also 2-methylpentanal, and a liquid aqueous phase containing a water-soluble cobalt catalyst. The gas phase and the liquid aqueous phase are returned to the hydroformylation reactor by metering devices. The fact that 2-methylpentenal and 2-methylpentanal were obtained directly at the hydroformylation step was unexpected.

The liquid organic phase, containing mainly propanal, as well as 2-methylpentenal and 2-methylpentanal, is transferred to the reactor filled with a granular catalyst, containing oxides of NiO, CuO and $Cr_2O_3$ in a molar ratio of 1:1:1, where at a temperature of 150 to 200° C. and a pressure of 4.5 to 5.0 MPa, the mixture of aldehydes is converted into a mixture of the corresponding alcohols, that is n-propanol and 2-methylpentanol.

Hydroformylation of propylene is carried out in the reactor with a stirring device at a temperature of 135 to 140° C. and a pressure of 3.0 to 5.0 MPa. The molar ratio of the feed gases: $C_3H_6$:CO:$H_2$ is from 1:1:1 to 1:1.5:2.5 and is maintained by flow meters. $C_2$-$C_3$ alcohols are added to the water-soluble cobalt catalyst in the volume ratio $H_2O$:($C_2$-$C_3$)=(0.95-0.5):(0.05-0.5) in order to increase the rate of the reaction of propylene hydroformylation and to increase the yield of isobutanal. In order to reduce catalyst losses, the organic phase formed during hydroformylation of propylene is separated from the aqueous phase, in which the Co catalyst is dissolved, using a highly efficient centrifugal separator. The resulting reaction mass is transferred to a highly efficient centrifugal separator for separation into three phases: a gas phase containing unreacted propylene, carbon monoxide and hydrogen, a liquid organic phase, containing n-butanal, isobutanal, 2-ethylhexenal and 2-ethylhexanal, as well as some amounts of the corresponding alcohols, and a liquid aqueous phase containing a water-soluble cobalt catalyst. The gas phase and the liquid aqueous phase are returned to the hydroformylation reactor by metering devices. The fact that 2-ethylhexenal and 2-ethylhexanal and also butyl alcohols and 2-ethyl hexanol were obtained directly in the hydroformylation step was unexpected.

A mixture of n-butanal and isobutanal is separated by rectification from the liquid organic phase containing n-butanal and isobutanal in a mass ratio of (2-3):1, as well as 2-ethylhexenal and 2-ethylhexanal.

The mixture of n-butanal and isobutanal is directed to the reactor filled with a granular catalyst containing at least 93% of ZSM-5 zeolite modified by 3.5 to 7.0% Zn, or a granular catalyst containing at least 95% of ZSM-5 zeolite modified by 3.5 to 5.0% Zn and 0.1 to 1.5% Ce, where, at a temperature of 100 to 150° C. and a pressure of 0.5 to 1.0 MPa, n-butanal is converted into 2-ethylhexenal.

The aldehydes thus obtained are then combined into a general mixture containing isobutanal, 2-ethylhexenal and 2-ethylhexanal. This mixture of aldehydes is sent to the reactor filled with a granular catalyst consisting of the oxides NiO, CuO and $Cr_2O_3$ in a molar ratio of 1:1:1, where at a temperature of 150 to 200° C. and a pressure of 3.0 to 5.0 MPa, isobutanal, 2-ethylhexenal and 2-ethylhexanal are converted into a mixture of the corresponding alcohols, that is: isobutanol and 2-ethylhexanol.

Moreover, in a preferred embodiment, the inventive method provides for obtaining $C_3$-$C_6$ alcohols as follows. To obtain $C_8$ alcohol, namely: 2-methyl butanol, acetaldehyde along with gaseous feed is supplied at a temperature of 120-140° C. and a pressure of P=2.0-5.0 MPa in a molar ratio $(C_2H_4$:CO:$H_2)$:$(C_2H_4O)$=1:0.5 to a water-soluble Co catalyst during the reaction of ethylene hydroformylation by synthesis gas. This yields propanal, 2-methylpentenal and 2-methylpentanal, as well as 2-methylbutenal, which is formed due to the cross aldol condensation of acetaldehyde with propanal. Then the resulting mixture of propanal and aldols $C_5$-$C_6$ is hydrogenated in the presence of a heterogeneous catalyst consisting of the oxides NiO, CuO and $Cr_2O_3$ in a molar ratio of 1:1:1 at a temperature of 150-200° C. and a pressure of P=4.5-5.0 MPa to obtain a mixture of $C_3$-$C_6$ alcohols containing 2-methyl butanol.

In a similar way, in order to obtain $C_7$ alcohols, namely 2-methyl hexanol and 2-ethyl pentanol, propanal along with a gaseous feed is supplied, during reaction of propylene hydroformylation by synthesis gas, at a temperature of 135-140° C. and a pressure of P=2, 0-5.0 MPa in a molar ratio $(C_3H_6$:CO:$H_2)$:$(C_3H_6O)$=1:(0.5-1) to a water-soluble Co catalyst. This yields isobutanal, 2-methylpentenal, 2-methylpentanal, 2-ethyl hexenal, and 2-ethyl hexanal, as well as 2-methyl hexenal and 2-ethyl pentenal, which are formed due to the cross-aldol condensation of n-butanal with propanal. Then the resulting mixture of isobutanal and aldols $C_6$-$C_8$ is hydrogenated in the presence of a heterogeneous catalyst consisting of the oxides NiO, CuO and $Cr_2O_3$ in a molar ratio of 1:1:1, at a temperature of 150-200° C. and a pressure of P=4.5-5.0 MPa yielding a mixture of $C_4$-$C_8$ alcohols containing, inter alia, 2-methyl hexanol and 2-ethyl pentanol.

Hydroformylation of ethylene and propylene uses synthesis gas obtained by the inventive technology. For the production of synthesis gas, carbon dioxide and hydrogen obtained during conversion of ethanol into acetone at the step 1.1 of the inventive method are used. The synthesis gas production process is performed by two methods. In the first method, a mixture of carbon dioxide and hydrogen in a molar ratio of $CO_2$:$H_2$=1:1 is supplied into the reactor, filled with a granular catalyst 5 to 10% Cu supported by $Al_2O_3$, at a temperature of 550 to 600° C. and a pressure of 3.0 to 5.0 MPa. The carbon monoxide thus obtained is cooled, isolated from water and directed to step 1.8 of the inventive method, to the hydroformylation reactor. Simultaneously with carbon monoxide, hydrogen is fed into the hydroformylation reactor in a molar ratio of CO:$H_2$=1:1.

In the second method, a mixture of carbon dioxide and hydrogen, in a molar ratio of $CO_2$:$H_2$=1:(2-3), is supplied into a reactor filled with a granular catalyst consisting of the oxides NiO, CuO and $Cr_2O_3$ in a molar ratio of 1:1:1, at a temperature of 950 to 1000° C. and a pressure of 0.1 to 0.5 MPa. The mixture of carbon monoxide and hydrogen thus obtained is cooled, isolated from water, carbon dioxide and methane, and then transferred to the synthesis gas collecting tank for the adjustment of the composition. Simultaneously with a mixture of carbon monoxide and hydrogen, hydrogen is fed into the synthesis gas collecting tank to adjust the molar ratio to $CO:H_2=1:1$. From the synthesis gas collecting tank the mixture of carbon monoxide and hydrogen is directed to the hydroformylation reactor at step 1.8 of the inventive method by a compressor at a pressure of 3.0 to 5.0 MPa.

The $C_2$-$C_8$ alcohols synthesized by the inventive processes can be converted into motor fuel both individually and as mixtures. The main pathway for the conversion of $C_2$-$C_8$ alcohols into higher paraffins is based on the oligomerization of $C_2$-$C_8$ olefins, which, in turn, are obtained by dehydration of the corresponding alcohols.

According to the invention, it is recommended to use zeolites modified by Zn and Ce, that is a zeolite-containing catalyst, containing at least 93% ZSM-5 modified by 3.5 to 7.0% Zn, or a zeolite-containing catalyst, comprising at least 95% ZSM-5 modified by 3.5 to 5.5% Zn and 0.1 to 1.5% Ce as catalysts for $C_2$-$C_8$ olefin oligomerization. Also, it is recommended to use zeolites modified by Zn and Ce as catalysts for oligomerization of $C_2$-$C_8$ olefins.

The inventive method for producing motor fuel provides for using a mixture of primary and secondary $C_2$-$C_5$ alcohols, which include $C_3$-$C_5$ alcohols synthesized from ethanol, as a feedstock. For this, primary and secondary $C_2$-$C_5$ alcohols are dehydrated using a catalyst gamma $Al_2O_3$ in a continuous flow reactor at a temperature of 350-450° C. and a pressure of 0.5-3.5 MPa to yield $C_2$-$C_5$ olefins. $C_2$-$C_5$ olefins thus obtained are then oligomerized in the presence of a heterogeneous granular catalyst containing at least 93% of ZSM-5 zeolite modified by 3.5-7.0% Zn, or a granular catalyst containing no less than 95% of ZSM-5 zeolite modified by 3.5-5.0% Zn and 0.1-1.5% Ce at a temperature of 250-350° C. and a pressure of P=2.5-5.0 MPa.

The $C_6$-$C_{20}$ olefins formed in the process of oligomerization are hydrogenated in the presence of a heterogeneous catalyst consisting of the oxides NiO, CuO and $Cr_2O_3$ in a molar ratio of 1:1:1, at a temperature of 150-200° C. and a pressure of P=4.5-5.0 MPa to obtain a mixture of $C_6$-$C_{20}$ paraffins, which are suitable for isolation of, specifically, gasoline and kerosene fractions of motor fuel.

The oligomerization of the individual olefins in the presence of a zeolite-containing catalyst, comprising at least 93% ZSM-5 modified by 3.5 to 7.0% Zn, or a zeolite-containing catalyst, comprising at least 95% ZSM-5 modified by 3.5 to 5.5% Zn and 0.1 to 1.5% Ce, differs significantly from the process where the Amberlite 15 is used. For example, when the catalyst, comprising at least 93% ZSM-5 modified by 3.5 to 7.0% Zn catalyst is used in the oligomerization of propylene, obtained from propyl alcohol, olefins in the range $C_6H_{12}$, $C_7H_{14}$, $C_8H_{16}$, $C_9H_{18}$, $C_{10}H_{20}$, and so on up to $C_{24}H_{48}$ are obtained. Hydrogenation of the resulting oligomerization products leads to the production of the corresponding paraffins.

The mixture of primary and secondary $C_2$-$C_8$ alcohols, obtained at the step 1.3 of the inventive method, is sent for dehydration to obtain the corresponding mixture of unsaturated $C_2$-$C_8$ hydrocarbons. In turn, unsaturated $C_2$-$C_8$ hydrocarbons are used at the step 1.9 of the inventive method as a feedstock for the oligomerization process to obtain higher unsaturated $C_6$-$C_{24}$ hydrocarbons or for the aromatization process to obtain $C_7$-$C_{12}$ aromatic hydrocarbons. Moreover, a mixture of primary and secondary $C_2$-$C_8$ alcohols, from step 1.3 of the inventive method, is supplied to step 1.12 of the inventive method to obtain $C_7$-$C_{16}$ ethers.

Primary and secondary $C_2$-$C_8$ alcohols are dehydrated in the presence of a heterogeneous catalyst, gamma $Al_2O_3$, in a continuous-flow reactor at a temperature of 350 to 450° C. and a pressure of 0.5 to 3.5, MPa.

Unsaturated $C_2$-$C_8$ hydrocarbons and water are formed in the dehydration reactor. The reaction mixture from the reactor is fed to a separator to separate the unsaturated $C_2$-$C_8$ hydrocarbons from the water formed. The water is sent for utilization, and unsaturated $C_2$-$C_8$ hydrocarbons are collected in the collecting tank for further processing. Then the mixture of unsaturated $C_2$-$C_8$ hydrocarbons from the collecting tank is directed to the stage of oligomerization.

The unsaturated $C_2$-$C_8$ hydrocarbons obtained at step three of the inventive method by dehydration of the corresponding $C_2$-$C_8$ alcohols are directed to the oligomerization reactor at step nine of the inventive method. Oligomerization of the unsaturated hydrocarbons is performed at a temperature of 250 to 350° C. and a pressure of 2.0 to 5.0 MPa in the presence of a heterogeneous, zeolite-containing catalyst, comprising at least 93% ZSM-5 modified by 3.5 to 7.0% Zn, or a zeolite-containing catalyst comprising at least 95% ZSM-5 modified by 3.5 to 5.5% Zn and 0.1 to 1.5% Ce.

Following laboratory tests, it was found that the selected heterogeneous zeolite-containing catalyst, comprising at least 93% ZSM-5 modified by 3.5 to 7.0% Zn, or a zeolite-containing catalyst, comprising at least 95% ZSM-5 modified by 3.5 to 5.5% Zn and 0.1 to 1.5% Ce are most active in the oligomerization of $C_2$-$C_8$ olefins obtained from primary and secondary $C_2$-$C_8$ alcohols. In the course of oligomerization, the unsaturated $C_2$-$C_8$ hydrocarbons are converted into $C_6$-$C_{24}$ unsaturated hydrocarbons.

The unsaturated $C_6$-$C_{24}$ hydrocarbons are then hydrogenated in the presence of the catalyst consisting of the oxides NiO, CuO and $Cr_2O_3$ in a molar ratio of 1:1:1, at a temperature of 150 to 200° C. and a pressure of 3.0 to 5.0 MPa to yield a mixture of $C_6$-$C_{24}$ paraffins. $C_6$-$C_{24}$ paraffins obtained at step 1.9 of the inventive method are a feedstock for the production, at step 1.13 of the inventive method, of motor fuel, primarily kerosene, as well as gasoline and diesel.

It should be noted that the kerosene, obtained by the inventive method, has a number of unique properties. Studies performed by the inventor, which included mass spectroscopy, demonstrate that the composition of the kerosene, obtained solely from propylene, contains more than 150 different $C_8$-$C_{16}$ isomers and the linear hydrocarbons content is less than 5.0% mass. Such a kerosene, obtained solely from propylene, does not freeze at a temperature of minus 85° C., and also has a smoke point of more than 30 millimeters.

The unreacted at step 1.9 unsaturated $C_2$-$C_5$ hydrocarbons are used as a feedstock at step 1.11 of the inventive method in the process of aromatization to obtain $C_7$-$C_{12}$ aromatic compounds.

The unsaturated $C_2$-$C_5$ hydrocarbons obtained by rectification of the unsaturated $C_6$-$C_{24}$ hydrocarbons are supplied to step 1.11 of the inventive method to the aromatization reactor. Furthermore, a mixture of olefins and paraffins $C_1$-$C_4$, obtained at step 1.1 of the inventive method, is fed to the source reaction mixture at step 1.11. Aromatization of the unsaturated $C_2$-$C_5$ hydrocarbons is performed at a temperature of 350 to 450° C. and a pressure of 0.5 to 2.0 MPa in the presence of a heterogeneous zeolite-containing catalyst, comprising at least 93% ZSM-5 modified by 3.5 to 7.0% Zn in a continuous-flow reactor. The laboratory tests have established that the selected catalyst is most active in the aromatization of primary $C_4$-$C_5$ olefins. In the process of aromatization, the unsaturated $C_2$-$C_5$ hydrocarbons are converted into aromatic $C_7$-$C_{12}$ hydrocarbons.

$C_7$-$C_{12}$ aromatic hydrocarbons of step 1.11 are sent to step 1.13 of the inventive method for the production of motor fuel. Furthermore, a mixture of gaseous products is produced in the process of aromatization of the unsaturated hydrocarbons $C_2$-$C_5$. This mixture of gaseous products, comprised by hydrogen and $C_1$-$C_4$ paraffins, is separated from the liquid phase and sent to step 1.2 of the inventive method for producing synthesis gas.

Yet another way of ethanol conversion into motor fuel, developed by the inventor, is to use the reaction of telomerization for producing secondary and tertiary alcohols $C_3$-$C_8$. The main source material for this process is ethanol along with secondary alcohols such as iso-propanol or sec-butanol obtained from ethanol. Ethanol and isopropanol are supplied from step 1.1 of the inventive method to step 1.4 for telomerization. Furthermore, this process uses, as a raw material, ethylene obtained by dehydration of ethanol at step 1.3 of the inventive method.

The catalyst used in the reaction of telomerization is peroxides of tertiary alcohols, including tert-butyl or tert-amyl alcohols. The ratio of the catalyst: tert-butyl or tert-amyl alcohol peroxide to ethanol or secondary alcohols by mass is (1 to 2) % mass of tert-butyl or tert-amyl peroxide to (98 to 99) % of ethanol or secondary alcohol.

The process is carried out while stirring a liquid mixture of tert-butyl or tert-amyl alcohol peroxide and ethanol or isopropanol or a mixture of these alcohols under a pressure of gaseous ethylene P=1.0-5.0 MPa at a temperature of 100-130° C. Under these conditions, isopropanol is converted into tertiary $C_5$-$C_9$ alcohols, while ethanol is converted into sec-butanol and tertiary alcohols $C_6$-$C_{10}$. Conversion of ethanol into tertiary alcohols in this process was unexpected.

The obtained tertiary $C_5$-$C_8$ alcohols are isolated from the reaction mixture by rectification. In the process of rectification, individual tertiary alcohols or tertiary alcohol fractions are isolated. The yield of tertiary $C_5$-$C_8$ alcohols in terms of the reacted source alcohol reached more than 98% with a conversion rate of the initial alcohol higher than 60%. The yield of the obtained tertiary $C_{8+}$ alcohols did not exceed 2% mass. The unreacted source alcohols from telomerization were separated at the rectification stage and returned to the telomerization process or were used in the process of producing ethers. The resulting $C_{8+}$ tertiary alcohols can be used as oxygen-containing additives in the production of gasoline or diesel.

The mixture of tertiary $C_5$-$C_8$ alcohols obtained in the processes described above, is sent to step 1.5 of the inventive method for dehydration to obtain the corresponding mixture of unsaturated $C_5$-$C_8$ hydrocarbons. Dehydration of tertiary $C_5$-$C_8$ alcohols is carried out in the presence of a new or regenerated heterogeneous catalyst, gamma $Al_2O_3$ at a temperature of 100 to 150° C. and a pressure of 0.5 to 1.5 MPa until reaching the yield of $C_5$-$C_8$ olefins of at least 99% of the source $C_5$-$C_8$ alcohols. Then the temperature is increased to 350-450° C. and primary and/or secondary alcohols $C_2$-$C_8$ are dehydrated, wherein the process is continued in the presence of the same catalyst at a temperature not exceeding 450° C. until reaching the yield of $C_2$-$C_8$ olefins of not less than 99% of the source primary and/or secondary $C_2$-$C_8$ alcohols.

Upon completion of the dehydration of primary and/or secondary $C_2$-$C_8$ alcohols, the catalyst is regenerated.

$C_5$-$C_8$ unsaturated hydrocarbons and water are obtained in the dehydration reactor. The reaction mixture from the reactor is directed to the separator for separation of the mixture of unsaturated $C_5$-$C_8$ hydrocarbons from the water obtained. The water is sent for utilization and the unsaturated $C_5$-$C_8$ hydrocarbons are collected in the collecting tank for further processing. Further, the mixture of unsaturated $C_5$-$C_8$ hydrocarbons from the collecting tank is directed to step 1.6 of the inventive method for oligomerization.

The inventor recommends to use ion-exchange resins in the form of cation exchangers, for example, Amberlite15, as catalysts for oligomerization of $C_3$-$C_8$ olefins. Studies performed by the inventor have established that the use of Amberlite 15, as a catalyst in the process of oligomerization, obtains higher unsaturated compounds by way of condensation of the source olefin in the form of dimers, trimers, and so on. That is, higher olefins with a molecular weight as a multiple of the initial unsaturated compound appear. For example, oligomerization of propylene in the presence of a cation exchanger Amberlite 15 yields olefins $C_6H_{12}$, $C_9H_{18}$, $C_{12}H_{24}$, and so on up to $C_{24}H_{48}$. Hydrogenation of the resulting oligomerization products yields the corresponding paraffins.

At the same time the use of Amberlite 15 at the stage of oligomerization along with a mixture of at least two olefins: propylene and isobutylene, obtained from the corresponding alcohols, results in obtaining a mixture of higher olefins. Hydrogenation of said mixture of higher olefins yields a mixture of higher paraffins in the range $C_6H_{14}$, $C_7H_{16}$, $C_8H_{18}$, $C_9H_{20}$, $C_{10}H_{22}$ and so on up to $C_{24}H_{50}$.

Moreover, the unsaturated $C_5$-$C_8$ hydrocarbons obtained at step 1.5 by dehydration of tertiary alcohols $C_5$-$C_8$ are used at step 1.6 of the inventive method as a raw material in the reaction of oligomerization to obtain unsaturated hydrocarbons $C_{10}$-$C_{24}$.

Oligomerization of the unsaturated hydrocarbons $C_5$-$C_8$ is carried out in the presence of catalyst, ion-exchange resins in the form of cation exchangers, for example Amberlite15, in a continuous flow reactor at a temperature of 70-120° C. and a pressure of 1-2 MPa. Oligomerization of the unsaturated $C_5$-$C_8$ hydrocarbons yields a mixture of higher unsaturated hydrocarbons $C_{10}$-$C_{24}$.

The unsaturated $C_{10}$-$C_{24}$ hydrocarbons of step 1.6 of the inventive method are then hydrogenated at step 1.7 in the presence of a catalyst consisting of the oxides NiO, CuO and $Cr_2O_3$ in a molar ratio of 1:1:1, at a temperature of 150 to 200° C. and a pressure of 3.0 to 5.0 MPa, to obtain a mixture of $C_{10}$-$C_{24}$ paraffins.

$C_{10}$-$C_{24}$ paraffins obtained at step 1.7 are the source material for the production of motor fuel, first of all, kerosene, as well as gasoline and diesel at step 1.13 of the inventive method. The iso-structure of these hydrocarbons obtains kerosene and diesel with unique characteristics, as well as gasoline free of aromatic compounds with octane numbers of at least 95 RON and 91 MON. Studies carried out by the inventor, which included chromatomass spectroscopy, demonstrate that the composition of kerosene, obtained from tertamyl alcohol, contains more than 60 different $C_{10}$-$C_{15}$ isomers and there are no linear hydrocarbons. This kerosene, obtained from tertamyl alcohol, does not freeze at a temperature of minus 85° C., and also has a smoke point of more than 30 mm.

The inventive method for producing motor fuel provides for using tertiary $C_5$-$C_8$ alcohols, synthesized on the basis of ethanol, as a feedstock. For this purpose, $C_5$-$C_6$ olefins are isolated by rectification from the mixture of $C_5$-$C_8$ olefins of step 1.5, obtained by dehydration of tertiary alcohols $C_5$-$C_8$, and oligomerized at step 1.6 of the inventive method at a temperature of 70-120° C. and a pressure of P=1.5-2.0 MPa in the presence of catalyst, ion exchange resins in the form of cation exchangers, for example Amberlite15.

$C_{10}$-$C_{18}$ olefins obtained in the process of oligomerization are hydrogenated in a presence of a heterogeneous catalyst consisting of the oxides NiO, CuO and $Cr_2O_3$ in a molar ratio of 1:1:1, at a temperature of 150-200° C. and a pressure of P=4.5-5.0 MPa to obtain a mixture of $C_{10}$-$C_{18}$ paraffins, which almost entirely is a kerosene fraction of motor fuel.

Furthermore, $C_7$-$C_8$ olefins isolated from the mixture of $C_5$-$C_8$ olefins, obtained by dehydration of tertiary $C_5$-$C_8$ alcohols, are oligomerized at a temperature of 70-120° C. and a pressure P=1.5-2.0 MPa by using, as catalyst, ion-exchange resins in the form of cation exchangers, for example, Amberlite15.

$C_{14}$-$C_{24}$ olefins obtained as a result of oligomerization are hydrogenated in the presence of a heterogeneous catalyst consisting of the oxides NiO, CuO and $Cr_2O_3$ in a molar ratio of 1:1:1, at a temperature of 150-200° C. and a pressure of P=4.5-5.0 MPa to obtain $C_{14}$-$C_{24}$ paraffins. Subsequently, kerosene and diesel fractions of the motor fuel are isolated from said hydrocarbon mixture by rectification.

The inventive method for producing motor fuel from ethanol makes it possible to produce and use oxygen-containing additives, which, when used in gasoline and diesel compositions, improve significantly the quality of said compositions. The main oxygen-containing additives proposed herein to be used to improve properties of gasoline and diesel are ethers.

It is proposed to obtain these ethers by using primary or secondary $C_2$-$C_8$ alcohols, obtained by the inventive method of the motor fuel production. Furthermore, the unsaturated $C_5$-$C_8$ hydrocarbons, obtained by dehydration of tertiary alcohols $C_5$-$C_8$, can be used for producing said ethers.

The process for producing ethers is carried out at step 1.12 of the inventive method, in the presence of a catalyst, the ion-exchange resins in the form of cation exchangers, for example Amberlite15, in a continuous-flow reactor at a temperature of 50 to 100° C. and a pressure of 0.5 to 1.5 MPa. $C_2$-$C_8$ primary and secondary alcohols of step 1.3 of the inventive method, that are supplied to step 1.12, interact with $C_5$-$C_8$ olefins, of step 1.5 of the inventive method, that are supplied to step 1.12, to yield a mixture of $C_7$-$C_{16}$ ethers. The mixture of $C_7$-$C_{16}$ ethers is directed to step 1.13 of the inventive method for producing motor fuel.

As described above in the detailed description of the inventive method for ethanol conversion into motor fuel, the inventive technology provides for obtaining mixtures of paraffins in the $C_6$-$C_{24}$ range, consisting mainly of branched hydrocarbons. These paraffin mixtures are separated by rectification into fractions $C_6$-$C_{10}$, $C_{11}$-$C_{18}$, and $C_{19}$-$C_{24}$, suitable for producing gasoline, kerosene and diesel. In addition, the inventive technology for the production of aromatic compounds from ethanol provides for obtaining mixtures of aromatic hydrocarbons in the range $C_7$-$C_{12}$. These mixtures of aromatic hydrocarbons are separated by rectification into fractions $C_7$-$C_8$ and $C_9$-$C_{12}$, suitable for producing gasoline and kerosene. Mixing the gasoline fraction of $C_6$-$C_{10}$ paraffins with the gasoline fraction of $C_7$-$C_8$ aromatic hydrocarbons provides for obtaining gasoline meeting all the requirements of the EN 228 standard. Mixing the kerosene fraction of $C_{11}$-$C_{18}$ paraffins with the kerosene fraction of aromatic $C_9$-$C_{12}$ hydrocarbons provides for obtaining kerosene meeting all the requirements of the Jet A-1 standard.

At the same time, the inventive technology for the production of ethers from ethanol provides for obtaining mixtures of ethers in the range $C_7$-$C_{16}$. These mixtures of $C_7$-$C_{16}$ ethers are separated by rectification into fractions $C_7$-$C_{10}$ and $C_{11}$-$C_{16}$, suitable for producing gasoline and diesel. Mixing the gasoline fraction of $C_6$-$C_{10}$ paraffins with the gasoline fraction of $C_7$-$C_{10}$ ethers provides for obtaining gasoline meeting requirements of the EN 228 standard and free of aromatic compounds, and with octane ratings RON of at least 100 and MON of at least 93. Mixing the diesel fraction of $C_{19}$-$C_{24}$ paraffins with the diesel fraction of $C_{11}$-$C_{16}$ ethers provides for obtaining diesel meeting requirements of the EN 590 standard and completely free of aromatic hydrocarbons.

$C_6$-$C_{24}$ paraffins obtained from primary and secondary $C_2$-$C_8$ alcohols at steps 1.8, 1.9 and 1.10 of the inventive method for conversion of ethanol into motor fuel, and $C_{10}$-$C_{24}$ paraffins obtained from tertiary $C_5$-$C_8$ alcohols at steps 1.5, 1.6 and 1.7 of the inventive method, are supplied to step 1.13 for rectification to obtain $C_6$-$C_{10}$ gasoline, $C_{11}$-$C_{18}$ kerosene, and $C_{19}$-$C_{24}$ diesel fraction of the motor fuel. Moreover, aromatic $C_7$-$C_{12}$ hydrocarbons obtained from primary and secondary $C_2$-$C_5$ alcohols at steps 1.3, 1.9 and 1.11 of the inventive method are supplied to step 1.13 for rectification to yield $C_7$-$C_8$ gasoline and $C_9$-$C_{12}$ kerosene fractions of the motor fuel. $C_7$-$C_8$ aromatic hydrocarbons are used to produce gasoline meeting all requirements of the EN 228 standard. $C_9$-$C_{12}$ aromatic hydrocarbons are used to produce kerosene meeting all the requirements of the Jet A-1 standard.

Also, $C_7$-$C_{16}$ ethers, obtained at steps 1.3, 1.4, 1.5 and 1.12 from primary and secondary $C_2$-$C_8$ alcohols, and $C_5$-$C_8$ olefins, obtained from tertiary $C_5$-$C_8$ alcohols, are supplied to step 1.13 for rectification, and are separated into a mixture of $C_7$-$C_{10}$ ethers and a mixture of $C_{11}$-$C_{16}$ ethers. $C_7$-$C_{10}$ ethers are used to produce a high-quality gasoline, while $C_{11}$-$C_{16}$ ethers are used to produce a high-quality diesel.

The use of the ethers obtained in the inventive process in the compositions of gasoline provides for excluding aromatic compounds from compositions of gasoline and for reducing the harmful effects of the gasoline combustion products on the environment. Up to 22% of ethers by volume are allowed in gasoline according to the current standards. However, it is necessary to comply with the oxygen content limit, which for various standards can be not higher that 2.7% by weight or 3.2% by weight.

The compositions of gasoline obtained by the invention with an ether content of not more than 20% by volume provide for achieving RON ratings of at least 100 and MON of at least 93, without violating the above requirements for oxygen content.

A distinguishing feature of the inventive method for obtaining motor fuel from $C_6$-$C_{24}$ paraffins, synthesized from ethanol, is that in order to obtain gasoline fully meeting the requirements of the existing EN 228 standard, the $C_6$-$C_{10}$ paraffin fraction isolated from a mixture of $C_6$-$C_{24}$ paraffins is mixed with a fraction of $C_7$-$C_{10}$ ethers isolated from a mixture of $C_7$-$C_{16}$ ethers, synthesized from ethanol, and/or with a fraction of $C_7$-$C_8$ aromatic hydrocarbons, isolated from a mixture of $C_7$-$C_{16}$ aromatic hydrocarbons, which are also synthesized from ethanol. The $C_7$-$C_{16}$ ethers required for mixing are obtained by etherification of primary or secondary $C_2$-$C_8$ alcohols with $C_5$-$C_8$ olefins obtained from tertiary $C_5$-$C_8$ alcohols.

The esterification process is carried out in the presence of catalyst, which is an ion-exchange resin in the form of cation exchanger, for example Amberlite15, at a temperature of 70-120° C. and a pressure of P=1.5-2.0 MPa. For the production of $C_7$-$C_{16}$ ethers are used primary or secondary $C_2$-$C_8$ alcohols, obtained from tertiary $C_5$-$C_8$ alcohols, and $C_5$-$C_8$ olefins, wherein all raw material for the production of $C_7$-$C_{16}$ ethers is obtained from ethanol.

According to one preferred embodiment of the inventive method, in order for obtaining motor fuel from $C_6$-$C_{24}$ paraffins, synthesized from ethanol, in order to produce diesel fuel that meets all requirements of the existing EN 590 standard, the $C_{19}$-$C_{24}$ paraffin fraction isolated from a mixture of $C_6$-$C_{24}$ paraffins, is mixed with the fraction of $C_{11}$-$C_{16}$ ethers, isolated from a mixture of $C_7$-$C_{16}$ ethers, said $C_7$-$C_{16}$ ethers are also synthesized from ethanol. Wherein, the $C_7$-$C_{16}$ ethers required for the mixing are produced by etherification of primary or secondary $C_2$-$C_8$ alcohols by $C_5$-$C_8$ olefins, obtained from tertiary $C_5$-$C_8$ alcohols.

The esterification is performed in the presence of catalysts, the ion-exchange resin in the form of cation exchangers, for example Amberlite15, at a temperature of 70-120° C. and a pressure of P=1.5-2.0 MPa. For the production of $C_7$-$C_{16}$ ethers are used primary or secondary $C_2$-$C_8$ alcohols, obtained from tertiary $C_5$-$C_8$ alcohols, and $C_5$-$C_8$ olefins, wherein all raw material for the production of $C_7$-$C_{16}$ ethers is obtained from ethanol.

According to a preferred embodiment of the inventive method, in order to obtain kerosene meeting all the requirements of the existing standard Jet A-1 from $C_6$-$C_{24}$ paraffins (obtained at steps: 1.3, 1.8, 1.9 and 1.10 from primary and secondary alcohols $C_2$-$C_8$), from $C_{10}$-$C_{24}$ paraffins (obtained at steps: 1.4, 1.5, 1.6 and 1.7 from tertiary $C_5$-$C_8$ alcohols), and from aromatic $C_7$-$C_{12}$ hydrocarbons (obtained at steps: 1.3, 1.9 and 1.11 from the primary and secondary $C_2$-$C_5$ alcohols), the $C_{11}$-$C_{18}$ paraffins required in the kerosene composition, obtained at step 1.10 and isolated from the mixture of $C_6$-$C_{24}$ paraffins at step 1.13, the $C_{11}$-$C_{18}$ paraffins, obtained at step 1.7 and isolated from the mixture of $C_{10}$-$C_{24}$ paraffins at step 1.13, and the aromatic $C_9$-$C_{12}$ hydrocarbons, obtained at step 1.11 and isolated from the mixture of aromatic $C_7$-$C_{12}$ hydrocarbons, are mixed so that the concentration of aromatic $C_9$-$C_{12}$ compounds is in the range of 8-25% vol, while the resulting kerosene composition comprises at least 100 different hydrocarbons, and preferably 150 different hydrocarbons, and has a smoke point of min 30 mm and a freezing point of max minus 80° C.

It should be noted that the inventive method for the production of motor fuel provides for using not only ethanol containing a significant amount of water, but also ethanol containing a large amount of fusel oils. Also, the inventive method for ethanol conversion into motor fuel can use carbon dioxide and methane, obtained during the production of ethanol, as an additional raw material.

Moreover, the inventive method is not limited only to the motor fuel production industry. The inventive method for converting ethanol into $C_3$-$C_8$ containing aldehydes, ketones, alcohols: primary, secondary and tertiary, olefins, as well as $C_6$-$C_{24}$ containing olefins and branched paraffins may be in demand in the chemical and cosmetic industries.

The implementation of the inventive method for producing motor fuels is demonstrated by the following examples.

Example 1. Conversion of Ethanol into a Mixture
of Higher Alcohols and Hydrocarbons, as well as
into Synthesis Gas The process of converting ethanol into a mixture of higher alcohols and hydrocarbons, as well as into synthesis gas, was carried out in a cascade of reactors filled with appropriate heterogeneous catalysts. At the first step of the process, an aqueous solution of ethanol was supplied into a one liter volume continuous flow reactor, where the catalyst was loaded. The catalyst consists of the following metal oxides: ZnO 60 to 63% mass.; $CeO_2$ 1 to 6% mass.; MgO 12 to 18% mass.; $Al_2O_3$ 13-23% mass, with the proportions calculated in terms of metal oxide. The technological parameters of the process varied within the following ranges: temperature 500 to 515° C., pressure 0.9 to 1.1 MPa, ethanol concentration in water 59 to 63% wt, load 0.45 to 0.77 kg of ethanol solution in water per 1 liter of catalyst. The gaseous reaction mass obtained as a result of the interaction of ethanol with water was directed to step 1.2 of the process while the liquid reaction mass was directed to step 1.3 of the process.

The gaseous reaction mass, which is a mixture of hydrogen, carbon dioxide, saturated $C_1$-$C_4$ and unsaturated $C_2$-$C_4$ hydrocarbons, was supplied to step 1.2 of the process. This gaseous reaction mass was directed into a one liter volume continuous flow reactor filled with a heterogeneous zeolite-containing catalyst, comprising at least 93% ZSM-5 modified by 3.5 to 7.0% Zn catalyst. The technological parameters of the process varied within the following limits: temperature 350 to 450° C., pressure 0.5 to 1.0 MPa. Under these conditions, the $C_2$-$C_4$ olefins contained in the gaseous reaction mass were converted into aromatic compounds, and the obtained gas mixture was directed to the absorber to extract carbon dioxide. The gas mixture, free from carbon dioxide, with a hydrogen content exceeding 95%, was directed to step 1.3 of the process.

At step 1.3 of the process, acetaldehyde was isolated from the liquid reaction mass obtained at step 1.1 of the process. After that the remaining liquid reaction mass was separated into organic and aqueous phases. The aqueous phase, containing unreacted ethanol, is returned to the process to produce the aqueous ethanol solution. The organic phase, which is a mixture of $C_3$ and $C_5$ ketones and $C_3$ and $C_5$ alcohols, was directed to the step of hydrogenation. To do this, the mixture of oxygen-containing products of ethanol conversion was supplied into a 1-liter continuous flow reactor, equipped with the catalyst consisting of the oxides CuO and $Cr_2O_3$ in a molar ratio of 1:1. The technological parameters of the process varied within the following limits: temperature 100 to 150° C., pressure 0.5 to 0.9 MPa. The gas mixture obtained at the second step of this process was supplied into the reactor loaded with the catalyst, comprised by oxides CuO and $Cr_2O_3$ in a molar ratio of 1:1, along with the mixture of the liquid oxygen-containing products of the ethanol conversion. Under these conditions, the $C_3$ and $C_5$ ketones contained in the liquid organic mixture were converted into the corresponding $C_3$ and $C_5$ alcohols. The residual unsaturated compounds were removed from the gas mixture obtained in the presence of the catalyst, comprised by oxides CuO and $Cr_2O_3$ in a molar ratio of 1:1, by hydrogenation. This gas mixture is an excellent raw material for synthesis gas production. Table 1 shows the results of a few experiments carried out in accordance with the described technological process for converting a mixture of ethanol and water into a mixture of alcohols, aromatic hydrocarbons, and also into synthesis gas.

TABLE 1

Results of experiments on the conversion of a mixture of ethanol and water
in the presence of the catalyst consisting of the following metal oxides: ZnO 60 to 63% mass;
$CeO_2$ 1 to 6% mass; MgO 12 to 18% mass; $Al_2O_3$ 23 to 13% mass, with the proportions
calculated in terms of metal oxide.

| Experiment # | Experiment duration in hours | Alcohol concentration, % vol. | Reaction temperature, °C. (Pressure, MPa) | Rate of ethanol solution supply ml/min | Load per 1 liter of catalyst l/hour of ethanol solution |
|---|---|---|---|---|---|
| 20193005 | 24 | 71.0 | 515 (1 +/− 0.1) | 32.8 | 0.788 |
| Supply | Ethanol, kg | Carbon in ethanol, kg | Water, kg | | |
| | 26.480 | 13.816 | 15.286 | | |
| Conversion % | Ethanol, kg (%) | 91.125% | | | |
| | 24.130 (91.125) | 12.590 | | | |
| Consumption | Acetaldehyde and isopropanol, kg (Carbon in acetaldehyde and isopropanol, kg) | $C_1$-$C_4$ hydrocarbons, kg (including carbon, kg) | $C_5$ alcohols, kg (including carbon, kg) | Aromatic $C_7$-$C_{11}$ kg (including carbon, kg) | Synthesis gas kg (Carbon in carbon dioxide, kg) |
| | 10.759 (6.452) | 1.089 (0.891) | 2.346 (1.663) | 0.211 (0.190) | 8.920 (3.329) |
| Yield %, *) notes | 51.25 | 7.08 | 13.21 | 1.51 | 26.44 |
| 20190206 | 24 | 70.8 | 515 (1 +/− 0.1) | 37.4 | 0.898 |
| Supply | Ethanol, kg | Carbon in ethanol, kg | Water, kg | | |
| | 30.106 | 15.707 | 17.380 | | |
| Conversion % | Ethanol, kg (%) | 84.18% | | | |
| | 25.344 (84.18) | 13.223 | | | |
| Consumption | Acetaldehyde and isopropanol, kg (Carbon in acetaldehyde and isopropanol, kg) | $C_1$-$C_4$ hydrocarbons, kg (including carbon, kg) | $C_5$ alcohols, kg (including carbon, kg) | Aromatic $C_7$-$C_{11}$ kg (including carbon, kg) | Synthesis gas, kg (Carbon in carbon dioxide, kg) |
| | 11.056 (6.750) | 1.068 (0.878) | 2.114 (1.787) | 0.222 (0.200) | 9.568 (3.587) |
| Yield %, *) notes | 51.05 | 6.64 | 13.51 | 1.51 | 27.13 |
| 20192903 | 24 | 65.8 | 500 (1 +/− 0.1) | 22.1 | 0.518 |
| Supply | Ethanol, kg | Carbon in ethanol, kg | Water, kg | | |
| | 16.501 | 8.609 | 11.419 | | |
| Conversion % | Ethanol, kg (%) | 99.01% | | | |
| | 16.337 (99.01) | 8.523 | | | |
| Consumption | Acetaldehyde and isopropanol, kg (Carbon in acetaldehyde and isopropanol, kg) | $C_1$-$C_4$ hydrocarbons, kg (including carbon, kg) | $C_5$ alcohols, kg (including carbon, kg) | Aromatic $C_7$-$C_{11}$ kg (including carbon, kg) | Synthesis gas, kg (Carbon in carbon dioxide, kg) |
| | 6.633 (4.013) | 0.677 (0.549) | 1.480 (1.045) | 0.819 (0.737) | 5.592 (2.097) |
| Yield %, *) notes | 47.08 | 6.44 | 12.26 | 8.65 | 24.6 |

Note *):
the yield of final products is calculated in terms of the carbon contained in ethanol reacted with water according
to the conversion.

Example 2. Synthesis Gas Generation in the Presence of Copper and Nickel Catalysts Synthesis gas, obtained on the basis of the inventive technology, is used in the inventive process of hydroformylation of ethylene and propylene.

For the production of synthesis gas, carbon dioxide and hydrogen obtained in the conversion of ethanol to acetone are used. Carbon dioxide is distilled off from the liquid reaction mass in the process of acetaldehyde distillation. In addition, carbon dioxide is extracted from the absorbent solution obtained during the purification of hydrogen, which is supplied to the stage of hydrogenation of acetone and other oxygen-containing compounds. The gas mixture leaving the stage of hydrogenation contains more than 90% hydrogen and is an excellent raw material for the production of synthesis gas by the inventive technology. The synthesis gas thus obtained is used in the process of ethylene and propylene hydroformylation.

The synthesis gas production by the inventive technology is carried out by two methods.

In the first method, carbon dioxide and mixture of 90% hydrogen in a molar ratio of $CO_2:H_2=1:(1.1-1.5)$ are fed into a flow reactor filled with a granular catalyst of 5 to 10% Cu supported on $Al_2O_3$ at a temperature of 550 to 600° C. and a pressure of 3.0 to 5.0 MPa. The carbon monoxide obtained in this process is cooled and isolated from water and a mixture of $C_1$-$C_4$ paraffins. The carbon monoxide, free of water, and the mixture of $C_1$-$C_4$ paraffins is directed to the hydroformylation reactor. Simultaneously with carbon monoxide, hydrogen is fed into the hydroformylation reactor in a molar ratio of $CO:H_2=1:1$.

In the second method, carbon dioxide and hydrogen in a molar ratio of $CO_2:H_2=1:(2-3)$ are fed into a flow reactor filled with a granular catalyst consisting of the oxides NiO, CuO and $Cr_2O_3$ in a molar ratio of 1:1:1, at a temperature of 950 to 1000° C. and a pressure of 0.1 to 0.5 MPa. The mixture of carbon monoxide and hydrogen obtained in this process is cooled, isolated from water, carbon dioxide and methane, and then sent to the synthesis gas collecting vessel to adjust the composition. Simultaneously with the mixture of carbon monoxide and hydrogen, hydrogen is fed into the synthesis gas collecting vessel to adjust the molar ratio of $CO:H_2=1:1$. From the synthesis gas collecting vessel the mixture of carbon monoxide and hydrogen in a molar ratio of $CO:H_2=1:1$ is sent to the hydroformylation reactor by a compressor at a pressure of 3.0 to 5.0 MPa.

Example 3. Obtaining Di Tert-Amyl Peroxide

Under vigorous stirring, tert-amyl alcohol is added to an aqueous solution of 70% sulfuric acid, cooled to a temperature of 0 to 5° C., in a molar ratio of $H_2SO_4:(CH_3)_2C(OH)$ $CH_2CH_3=1:1$. After adding the entire amount of tert-amyl alcohol the resulting reaction mass is stirred at a temperature of 0 to 5° C. for 10 to 15 minutes.

Then, an aqueous solution of 27% hydrogen peroxide is added to the resulting tert-amyl sulfate at a temperature of 0 to 5° C., with vigorous stirring, in a molar ratio of tert-amyl sulfate to hydrogen peroxide:$(CH_3)_2C(HSO_4)$ $CH_2CH_3$: $H_2O_2=1:0.5$. After adding the entire amount of 27% hydrogen peroxide, the reaction mixture is further stirred at a temperature of 5 to 20° C. for 60 minutes.

After the stirring is finished the reaction mass is divided into two layers. The upper layer, containing the formed di-tert-amyl peroxide is separated from the aqueous acidic layer and washed under stirring by a 10% aqueous solution of potassium carbonate and then by water to pH of 7. The crude di-tert-amyl peroxide washed from acid and alkali to neutral reaction is distilled under vacuum, at a pressure of 10 to 15 mm Hg, to collect the fraction boiling at 40 to 45° C. The yield of di tert-amyl peroxide after distillation is not less than 65%.

Example 4. Radical Addition of Ethylene to Isopropanol

In a 2000 ml volume reactor, a steel autoclave of type "PARR", were placed 470 ml of isopropyl alcohol (369 g, 6.15 mol) and 4 g of di-tert-amyl peroxide. The reactor was purged 3 times by nitrogen at 5 atm and 2 times by ethylene at 5 atm. After purging, 12 to 15 liters of ethylene was fed into the reactor and the internal temperature was increased to 130 to 135° C. Absorption of ethylene begins at this temperature. While ethylene was being absorbed an additional amount of ethylene was fed in at a rate of 0.1 to 0.2 liters per minute to maintain the pressure in the system at 12 to 14 atm. About 30 to 32 liters of ethylene were absorbed during 4 hours of reaction. Then the reactor was cooled and an additional 4 g of di-tert-amyl peroxide was added. the autoclave was reheated to 130 to 135° C. while maintaining the pressure in the system at 12 to 14 atm by feeding in ethylene. During 4 hours of reaction, an additional 20 to 22 liters of ethylene were absorbed. After cooling the reactor, 4 g of di-tert-amyl peroxide were added again and the experiment was repeated. During the entire experiment 84 liters (105 g) of ethylene were consumed and 600 ml (480 g) of the product were obtained.

The mixture of alcohols in the amount of 600 ml thus obtained in the reaction of telomerization was subjected to distillation. After distillation at atmospheric pressure and a temperature of 80 to 90° C., 250 ml of isopropyl alcohol were obtained. The subsequent distillation yielded 340 ml of tertiary alcohols boiling at 100 to 250° C. and 10 ml of tertiary alcohols boiling at a higher temperature, which remained in the bottoms. The yield of tertiary alcohols obtained from the reacted isopropyl alcohol, ethylene and tert-amyl peroxide was more than 99%.

The yield of tertiary $C_5$-$C_7$ alcohols was about 80%, and the yield of tertiary $C_9$-$C_{11}$ alcohols was about 17.1%. According to GLC analysis, the following was obtained: tert-amyl alcohol 57.4%; tert-heptyl alcohol 22.6%; tert-nonyl alcohol 11.4%, tert-undecyl alcohol 5.7% and tert-$C_{11}$+alcohols 2.9%. The conversion of isopropyl alcohol reached about 50%. These experiments were carried out with a "deficiency" of ethylene in order to avoid formation of heavier telomeres.

Example 5. Radical Addition of Ethylene to Ethyl Alcohol 408 ml (322 g, 7.0 mol) of ethyl alcohol and 45 ml (37 g, 0.21 mol) of di tert-amyl peroxide were placed in a 2000 ml volume reactor, a steel autoclave of type "PARR". The reactor was purged 3 times by nitrogen at 5 atm and 2 times by ethylene at 5 atm. Then, 12 liter (0.5 mol) of ethylene was fed into the reactor and the internal temperature was increased to 130 to 135° C. At this temperature absorbtion of ethylene begins. While ethylene was being absorbed at 130 to 135° C., an additional amount of ethylene was fed in at a rate of 0.1 to 0.3 liters per minute to maintain the pressure in the system at 12 to 14 atm. During 8 hours of the reaction, about 95 liters, (119 g, 4.25 mol) of ethylene were absorbed. Then the reactor was cooled, the reaction mixture was unloaded and transferred to distillation. The above experiment was repeated twice. In total, 1224 ml, (966 g, 21 mol) of ethyl alcohol and 135 ml, (111 g, 0.64 mol,) of di tert-amyl peroxide were consumed to perform the reaction of telomerisation, while 285 liter (356 g, 12.71 mol) of ethylene were absorbed.

In total, 1793 ml (1433 g) of alcohol mixture was obtained.

The mixture of alcohols in the amount of 1793 ml obtained as a result of the telomerization reaction was distilled. Distillation at atmospheric pressure and a temperature of 80° C. yielded 776 ml (612 g, 13.3 mol) of ethyl alcohol. Further distillation at atmospheric pressure and a temperature of 98° C. yielded 450 ml (364 g, 4.95 mol) of sec-butyl alcohol. Further distillation at atmospheric pressure additionally yielded 528 ml (425 g) of tertiary $C_5$-$C_8$ alcohols boiling between 102 and 180° C., and 30 ml (25 g) of tertiary alcohols boiling at higher temperatures, which remained in the bottoms.

The yield of secondary butyl alcohol and tertiary alcohols obtained from the reacted ethyl alcohol, ethylene and di-tert-amyl peroxide was more than 99%. The yield of secondary butyl alcohol was 44.3%. The yield of tertiary $C_5$-$C_8$ alcohols was 51.8%, and the yield of tertiary $C_{10}$-$C_{12}$ alcohols was about 3.0%. The rate of ethyl alcohol conversion was about 37%.

Example 6. Hydroformylation of Ethylene in the Presence of a Rhodium Catalyst The process of ethylene hydroformylation is carried out in a heterogeneous reaction medium using a water-soluble rhodium catalyst.

During hydroformylation of ethylene in the presence of a rhodium catalyst, the concentration of metal with respect to the aqueous phase is from 30 to 50 ppm. Triphenylphosphine-3-sulfonic acid sodium salt is used as a ligand in a ratio of 30:1 to metallic rhodium.

The process of obtaining propionic aldehyde is carried out at a temperature of 45 to 90° C. and a pressure of 1.0 to 2.5 MPa. The ratio of the source gases:$C_2H_4$:$CO$:$H_2$=(0.9-1): 1:1 is maintained by flow meters. The resulting reaction mass is directed to a highly efficient separator where it is separated into three phases: a gas phase containing non-reacted ethylene, carbon monoxide and hydrogen, a liquid organic phase containing mainly propanal, and a liquid aqueous phase containing a water-soluble rhodium catalyst. The gas phase and the liquid aqueous phase are returned to the hydroformylation reactor by metering devices.

An aqueous solution of the catalyst was loaded into a 2000 ml volume reactor with a highly efficient stirring device. The catalyst was then activated as follows. Synthesis gas was supplied in the ratio $CO$:$H_2$=1:1 into the reactor whilst stirring the catalyst solution until a pressure of 1.0 MPa was reached, after which the heating was switched on and the temperature was increased to 60 to 70° C. The catalyst solution was stirred for one hour at this temperature. Upon completion of catalyst activation, an automatic mode of the reaction temperature and pressure limit control was switched on at the instrument panel, which terminates supply of the reaction gases to the reactor. To prevent heating of the reaction mixture to a temperature critical for catalyst operation, the reactor is equipped with a refrigerator providing for removal of the excess heat. Water is used as the refrigerant. The gas supply rates for ethylene, carbon monoxide, and hydrogen were set at the flow meters installed on the gas supply lines into the reactor, and after that the gas supply to the reactor was switched on. After reaching the required volume of liquid reaction mass in the reactor, the pump was turned on to provide continuous pumping of the excess reaction mass to the separator. The separator separated the vapor and liquid phases, as well as separated the liquid phase into an organic phase containing propionic aldehyde and an aqueous phase containing dissolved catalyst.

The optimum temperature for the process of hydroformylation is 45 to 90° C. at a pressure of 1.0 to 2.5 MPa. With a decrease in temperature below 45° C., a significant decrease in the yield of the target aldehyde was observed in all experiments. With an increase of temperature above 90° C., a decrease in conversion was also observed, however it was less significant. The experiments were carried out in the range of pressures of 1.0-2.5 MPa. It should be noted that all experiments were performed using one and the same sample of catalyst developed by the inventor. During the study, the catalyst was repeatedly separated from the reaction products and returned to the process. Its total service life exceeded 9000 hours. The catalyst demonstrated high selectivity in the experiments on ethylene hydroformylation. Conversion of the reaction gases at the optimal technological parameters exceeded 99.0%, the selectivity for aldehyde was higher than 99.5%.

Example 7. Aldol Condensation of Propanal and Obtaining Propyl and 2-Methylpentyl Alcohols Propanal obtained in the hydroformylation of ethylene by synthesis gas in the presence of a rhodium catalyst was supplied at a temperature of 100 to 150° C. and a pressure of 0.5 to 1.0 MPa into a one-liter flow reactor loaded with a granular catalyst containing at least 93% of ZSM-5 zeolite modified by 3.5 to 7.0% Zn. These conditions provide for aldol condensation of propanal and obtaining 2-methyl pentenal and $C_{6+}$ products of propanal condensation. The reaction mass obtained in the process of aldol condensation was supplied for hydrogenation into a flow reactor, where the catalyst containing oxides NiO, CuO and $Cr_2O_3$ in a molar ratio of 1:1:1 was loaded. Simultaneously with the reaction mass of the aldol condensation process, hydrogen is also supplied to the said reactor, equipped with catalyst consisting of the oxides NiO, CuO and $Cr_2O_3$ in a molar ratio of 1:1:1, at a temperature of 90 to 130° C. and a pressure of 4.0 to 5.0 MPa.

By way of hydrogenation, 2-methyl pentenal as well as the unreacted propanal and the resulting $C_{6+}$ products of condensation are converted into 2-methylpentanol, propyl alcohol, and $C_{6+}$ alcohols, respectively.

The rate of propanal conversion into 2-methyl pentenal in the process of aldol condensation was at least 50%. The total yield of the corresponding alcohols, propyl, 2-methyl pentyl, and $C_{6+}$ alcohols, in the hydrogenation of a mixture of propanal, 2-methyl pentenal, and $C_{6+}$ products of propanal condensation, exceeded 99%.

Example 8. Hydroformylation of Ethylene Using a Cobalt Catalyst

The hydroformylation of ethylene is performed in a heterogeneous reaction medium in the presence of a water-soluble cobalt catalyst.

During hydroformylation of ethylene in the presence of a cobalt catalyst, the concentration of metal in relation to the aqueous phase is from 0.1% to 0.15%. Triphenylphosphine- 3,3',3"-trisulfonic acid trisodium salt is used in the weight ratio 10:1 to metallic cobalt as a ligand.

The process of obtaining propionic aldehyde is performed at a temperature of 120 to 140° C. and a pressure of 3.0 to 5.0 MPa. The ratio of the source gases:$C_2H_4$:$CO$:$H_2$=(0.9-1): 1:1 is maintained by flow meters. The resulting reaction mass is directed to a highly efficient separator for separation into three phases: a gas phase containing unreacted ethylene, carbon monoxide and hydrogen, a liquid organic phase containing resulting products of chemical conversions; propanal, 2-methyl pentenal, 2-methyl pentanal and $C_{6+}$ products of propanal condensation, and a liquid aqueous phase containing a water-soluble cobalt catalyst. The liquid aqueous phase is returned to the hydroformylation reactor by metering pump. The gas phase is directed to the stage of synthesis gas production.

The liquid organic phase from the separator is directed to the rectification column for isolation of the reaction products: propanal, 2-methyl pentenal, 2-methyl pentanal and $C_{6+}$ products of propanal condensation, as well as water dissolved in this organic phase.

The organic products isolated at the rectification column were sent to hydrogenation to obtain the corresponding alcohols. Isolated at the rectification column water, dissolved in organic matter, accumulates at the bottom of the column and is periodically pumped into the hydroformylation reactor by a pump.

An aqueous solution of the catalyst was put in a 2000 ml reactor with a highly efficient stirring device. The catalyst was then activated. The activation was done as follows. Synthesis gas was supplied into the reactor in the ratio $CO$:$H_2$=1:1, while stirring the catalyst solution, until a pressure of 2.0 MPa was reached. Then the heating was switched on and the temperature was increased to 120 to 130° C. The catalyst solution was stirred at this temperature for two hours. Upon completion of catalyst activation, an automatic mode of reaction temperature and pressure limit control was switched on at the instrument panel, which terminates supply of the reaction gases to the reactor. To prevent heating of the reaction mixture to the critical temperature of catalyst operation, the reactor is equipped with a refrigerator for removal of the excess heat. Water is used as a refrigerant. The gas supply rates for ethylene, carbon monoxide, and hydrogen were set at the flow meters installed on the gas supply lines into the reactor, and then the gas supply to the reactor was switched on. After reaching the required volume of liquid reaction mass in the reactor, the pump was turned on to provide continuous pumping of the excess reaction mass to the separator. The separator separated the vapor and liquid phases, and also separated the liquid phase into an organic phase containing propanal; 2-methyl pentenal; 2-methyl pentanal and $C_{6+}$ products of propanal condensation, and into water, in which the catalyst is dissolved.

The optimum temperature for the hydroformylation process is 120 to 130° C. A decrease in temperature below 120° C. results in a significant decrease in the yield of the target products in all experiments. An increase of the temperature above 130° C. also results in a decrease of the conversion rate, though less significant. The experiments were carried out over the pressure range of 3.0 to 5.0 MPa. It should be noted that all experiments were carried out on one and the same sample of the inventive catalyst. During the study, the catalyst was repeatedly isolated from the reaction products and returned back to the process. Its total service life exceeded 1200 hours. The catalyst demonstrated high selectivity in the experiments on ethylene hydroformylation.

Conversion of the reaction gases at optimal technological parameters was higher than 98.0%, the selectivity for propanal reached 99.0%, and the selectivity for the totality of the products of propanal aldol condensation, that is 2-methyl pentenal, 2-methyl pentanal and the products of $C_{6+}$ propanal condensation reached 50%.

Example 9. Obtaining Propyl, 2-Methylpentyl and $C_{6+}$ Alcohols

Propanal, 2-methyl pentenal, 2-methyl pentanal and the products of $C_{6+}$ propanal condensation, obtained in the hydroformylation of ethylene by synthesis gas in the presence of a cobalt catalyst, were supplied at a temperature of 150 to 200° C. and a pressure of 4.0 to 5.0 MPa into a continuous flow, one liter reactor where a granular catalyst consisting of the oxides NiO, CuO and $Cr_2O_3$ in a molar ratio of 1:1:1, is loaded. Simultaneously with propanal, 2-methyl pentenal, 2-methyl pentanal and the $C_{6+}$ products of propanal condensation, hydrogen is also supplied into the reactor. By way of hydrogenation, propanal, 2-methyl pentenal, 2-methyl pentanal, and the $C_{6+}$ propanal condensation products are converted into propyl, 2-methylpentyl, and $C_{6+}$ alcohols, respectively. The total yield of the corresponding alcohols: propanol, 2-methyl-pentanol, and $C_{6+}$ alcohols in the process of hydrogenation of a mixture of propanal, 2-methyl pentenal, 2-methyl pentanal, and $C_{6+}$ propanal condensation products exceeded 99%.

Example 10. Hydroformylation of Propylene in the Presence of a Cobalt Catalyst The process of propylene hydroformylation is performed in a heterogeneous reaction medium using a water-soluble cobalt catalyst. During hydroformylation of propylene in the presence of a cobalt catalyst, the concentration of metal in relation to the aqueous phase is from 0.25% mass. to 0.5% mass. Triphenylphosphine-3-sulfonic acid sodium salt is used as a ligand in a weight ratio of 7:1 to metallic cobalt. To increase the rate of the propylene hydroformylation, as well as to increase the yield of isobutanal, ethanol is added to the water-soluble cobalt catalyst in the volume ratio of $H_2O$:$C_2H_5OH$=(0.75-0.65):(0.25-0.35).

The process of obtaining butyric aldehydes is carried out at a temperature of 135° C. to 140° C. and a pressure of 3.0 to 5.0 MPa. The ratio of the source gases: $C_3H_6$:$CO$:$H_2$=(0.9:1):1:1 is maintained by flow meters. The resulting reaction mass is directed to a highly efficient separator where it is separated into three phases: vapor, liquid organic and liquid water phase. The vapor phase containing the unreacted propylene, carbon monoxide and hydrogen is sent to the stage of synthesis gas production.

The liquid organic phase obtained in the chemical conversion, containing butanal, isobutanal, 2-ethyl hexenal, 2-ethyl hexanal, and the $C_{8+}$ products of butanal condensation, is transferred from the separator to the rectification column. The rectification column is used to separate the following reaction products: butanal, isobutanal, 2-ethyl hexenal, 2-ethyl hexanal, $C_{8+}$ products of butanal condensation, and water dissolved in this organic phase.

The liquid aqueous phase containing the water-soluble cobalt catalyst is returned back to the hydroformylation reactor by metering pump.

Organic products isolated by rectification were sent to hydrogenation to obtain the corresponding alcohols. Isolated by the distillation column water, dissolved in organic matter, accumulated in the bottom of the column and was periodically supplied by the pump to the hydroformylation reactor.

The experiments were carried out as follows. An aqueous solution of the catalyst was loaded into a 2000 ml reactor with an integrated highly efficient stirring device. The catalyst was then activated, it was done as follows. Synthesis gas was supplied in the ratio $CO:H_2=1:1$ into the reactor whilst stirring of the catalyst solution until a pressure of 2.0 MPa was reached, after which the heating was switched on and the temperature was increased to 140° C. The catalyst solution was stirred for two hours at this temperature. Upon completion of the catalyst activation, an automatic mode of control of reaction temperature and pressure limit was switched on at the instrument panel, which terminated supply of the reaction gases to the reactor. To prevent heating of the reaction mixture to the critical temperature of catalyst operation, the reactor is equipped with a refrigerator for removal of the excess heat. Water is used as a refrigerant. The gas supply rates for propylene, carbon monoxide, and hydrogen were set at the flow meters installed on the gas supply lines to the reactor and the gas supply was switched on. After reaching the required volume of liquid reaction mass in the reactor, the pump was turned on to provide continuous pumping of the excess reaction mass to the separator. The separator separated the vapor and liquid phases, as well as separated the liquid phase into an organic phase containing butanal, isobutanal, 2-ethyl hexenal, 2-ethyl hexanal, and the $C_{8+}$ products of 2-ethyl hexanal condensation, and into an aqueous phase containing dissolved catalyst. It should be noted that the ratio of butanal and isobutanal formed in the reaction mass during the entire experiment was within the ratio $(n-C_4H_8O):(iso-C_4H_8O)=$ (2-3):1.

The optimum temperature for the hydroformylation process is 138 to 140° C. The experiments were performed over the pressure range of 3.0 to 5.0 MPa. It should be noted that all experiments were performed by using one and the same sample of the developed catalyst. In the course of the studies performed by the inventor, the catalyst was repeatedly separated from the reaction products, and returned back to the process. Its total service life exceeded 240 hours. The catalyst demonstrated high selectivity in the experiments on the hydroformylation of propylene. Conversion of the reaction gases at the optimal technological parameters was above 98.0%, the selectivity for butyric aldehydes reached 99.0%. Moreover, the selectivity for the totality of the products of n-butanal aldol condensation: 2-ethyl hexenal, 2-ethyl hexanal, and the $C_{8+}$ products of the 2-ethyl hexanal condensation exceeded 60%.

Example 11. Obtaining Butyl, Isobutyl, and 2-Ethylhexyl Alcohols

Butanal, isobutanal, 2-ethyl hexenal, and 2-ethyl hexanal, obtained in the hydroformylation of propylene by synthesis gas in the presence of a cobalt catalyst, were isolated from the reaction mixture by rectification. The mixture of oxygen-containing products thus obtained was supplied at a temperature of 90 to 130° C. and a pressure of 4.0 to 5.0 MPa to a one-liter flow reactor where a granular catalyst, containing oxides NiO, CuO and $Cr_2O_3$ in a molar ratio of 1:1:1 was loaded. Hydrogen was also fed to the reactor simultaneously with butanal, isobutanal, 2-ethyl hexenal and 2-ethyl hexanal. In the course of hydrogenation, butanal, isobutanal, 2-ethyl hexenal, and 2-ethyl hexanal are converted to butyl, isobutyl, and 2-ethyl hexyl alcohols, respectively. The total yield of the corresponding alcohols, that is butyl, isobutyl, and 2-ethyl hexyl alcohol exceeded 99%.

Example 12. Obtaining Kerosene from Propyl Alcohol

Propyl alcohol is dehydrated in contact with the gamma $Al_2O_3$ catalyst at a temperature of 350 to 400° C. and a pressure of 1.0 to 2.0 MPa. The obtained propylene $(C_3H_6)$ is separated from water and directed at a temperature of 250-350° C. and a pressure of 3.0-5.0 MPa into a continuous flow reactor, equipped with the granular catalyst, containing at least 93% of ZSM-5 zeolite modified by 3.5 to 7.0% Zn, or a granular catalyst containing at least 95% of ZSM-5 zeolite modified by 3.5 to 5.0% Zn and 0.1 to 1.5% Ce. These conditions provide for oligomerization of propylene to yield $C_6$-$C_{24}$ olefins. Unreacted propylene is separated by distillation from the reaction mass of the oligomerization process and returned back to the process. The reaction mass, free of the source propylene, is directed for hydrogenation to a continuous flow reactor equipped with the granular catalyst consisting of the oxides NiO, CuO and $Cr_2O_3$ in a molar ratio of 1:1:1. Simultaneously with the products of oligomerization, hydrogen at 120-150° C. and a pressure of 4.0-5.0 MPa is supplied to the hydrogenation. The process of hydrogenation provides for the conversion of the unsaturated $C_6$-$C_{24}$ compounds obtained at the stage of oligomerization into $C_6$-$C_{24}$ paraffins. The reaction mass obtained at the stage of hydrogenation goes to rectification for separation into kerosene, as well as gasoline and diesel fractions.

Table 2 shows the main properties of the kerosene fraction free of aromatic compounds.

TABLE 2

| Jet fuel characteristics of Example 12. | | | | |
| --- | --- | --- | --- | --- |
| Property | Method | Unit | Limit | Result for Jet from Example 12 |
| Acid Number | ASTM D 3242 | mg KOH/g | Max 0.015 | 0.003 |
| Density at 15° C. | ASTM D 4052 | kg/m³ | 775-840 | 762.5 |
| Mono-Aromatics Content | ASTM D 6379 | % vol | Min 8 Max 25 | <0.1 |
| Olefines | ASTM D 1319 | % vol | | 0.3 |
| Distillation IBP | ASTM D 86 | ° C. | | 161.7 |
| Temperature @ 10% rec. | ASTM D 86 | ° C. | Max 205 | 177.0 |
| Temperature @ 50% rec. | ASTM D 86 | ° C. | | 183.8 |

TABLE 2-continued

Jet fuel characteristics of Example 12.

| Property | Method | Unit | Limit | Result for Jet from Example 12 |
|---|---|---|---|---|
| Temperature @ 90% rec. | ASTM D 86 | ° C. | | 234.2 |
| Distillation FBP | ASTM D 86 | ° C. | Max 300 | 250.9 |
| Residue | ASTM D 86 | % vol | Max 1.5 | 1.2 |
| Loss | ASTM D 86 | % vol | Max 1.5 | 0.2 |
| Sulphur Content | ASTM D 5453 | mg/kg | Max 0.3 | <0.1 |
| Flash Point Abel | IP 170 | ° C. | Min 38 | 50.0 |
| Freezing Point | ASTM D 2386 | ° C. | Max minus 47 | <minus 81 |
| Gum, Existent | ASTM D 381 | mg/100 ml | Max 7 | <1 |
| Smoke Point | ASTM D 1322 | mm | Min 25 | 33 |
| Water Reaction | ASTM D 1094 | | | 1b |
| Water Separation Index (MSEP) | ASTM D 3948 | | Min 85 | 98 |
| Particulate Contaminant Lab. Test | ASTM D 5452 | mg/l | Max 10 | 0.43 |
| Copper strip corrosion | ASTM D 130 | 2 h/100° C. | class 1 | 1A |
| Color (Saybolt) | ASTM D 156 | | Min 25 | 30 |
| Conductivity (no antistatic agent) | ASTM D 2624 | pS/m | Max 600 | <1 |
| JFTOT | ASTM D 3241 | 2.5 h 260° C., mmHg | Max 25 | <1 |
| JFTOT | ASTM D 3241 | Rating | Max 85 | 23 |
| JFTOT | ASTM D 3241 | ml | | 465 |
| JFTOT | ASTM D 3241 | ° C. | Min 325 | 325 |
| BOCLE | ASTM D 5001 | WSD mm | Max 0.85 | 0.84 |
| Specific Energy | ASTM D 3338 | MJ/kg | Min 42.8 | 44.06 |
| Viscosity @-20° C. | ASTM D 445 | $mm^2/s$ | Max 8.0 | 4.895 |

The study performed by the inventor using chromatography-mass spectroscopy demonstrates that the composition of kerosene, obtained solely from propylene, contains more than 160 different $C_8$-$C_{16}$ isomers, wherein 4.7 wt. % of those are linear hydrocarbons.

Example 13. Obtaining Kerosene from Isobutyl Alcohol

Isobutyl alcohol obtained by hydroformylation of propylene and subsequent hydrogenation of the resulting isobutyraldehyde is dehydrated in contact with the gamma $Al_2O_3$ catalyst at a temperature of 350 to 400° C. and a pressure of 1.0 to 2.0 MPa. The isobutylene ($C_4H_8$) obtained is separated from water and supplied at a temperature of 250 to 350° C. and a pressure of 3.0 to 5.0 MPa into a continuous flow reactor, equipped with granulated catalyst containing at least 95% zeolite ZSM-5 modified by 3.5-5.0% Zn and 0.1-1.5% Ce. These conditions provide for oligomerization of isobutylene to yield $C_8$-$C_{20}$ olefins. The unreacted isobutylene is distilled off the reaction mass obtained by oligomerization and returned back to the process. The reaction mass, free from the source isobutylene, is supplied for hydrogenation to the continuous flow reactor, equipped with catalyst consisting of the oxides NiO, CuO, and $Cr_2O_3$ in a molar ratio 1:1:1. Simultaneously with olefins obtained by oligomerization, hydrogen is supplied into the hydrogenation reactor at a temperature of 120 to 150° C. and a pressure of 4.0 to 5.0 MPa. By means of hydrogenation, the unsaturated $C_8$-$C_{20}$ compounds obtained at the stage of oligomerization are converted into $C_8$-$C_{20}$ paraffins. The reaction mass obtained at the stage of hydrogenation is directed to rectification for separation into kerosene, as well as gasoline and diesel fractions.

Example 14. Obtaining Kerosene from Tert-Amyl Alcohol

Tert-amyl alcohol (2-methyl-2-butanol) is dehydrated in contact with gamma $Al_2O_3$ catalyst at a temperature of 100-150° C. and a pressure of 1.0 to 2.0 MPa. The pentenes ($C_5H_{10}$) obtained are separated from water and supplied at a temperature of 100-150° C. and a pressure of 1.0 to 2.0 MPa into a continuous flow reactor, equipped with an ion-exchange resin in the form of a cation exchanger Amberlite 15, as catalyst. These conditions provide for oligomerization of pentenes to yield $C_{10}$-$C_{20}$ olefins. The unreacted pentenes are distilled off the reaction mass obtained by oligomerization and returned back to the process. The reaction mass, free of the source pentenes, is supplied for hydrogenation into a continuous flow reactor, equipped with the catalyst comprised by oxides NiO, CuO, and $Cr_2O_3$ in a molar ratio 1:1:1. Simultaneously with the oligomerization products, hydrogen at a temperature of 120 to 150° C. and a pressure of 4.0 to 5.0 MPa is supplied to the hydrogenation reactor. The unsaturated $C_{10}$-$C_{20}$ compounds obtained at the oligomerization stage are hydrogenated into $C_{10}$-$C_{20}$ paraffins. The yield of $C_{10}$-$C_{20}$ paraffins in terms of oligomerized pentenes is above 98%. The reaction mass obtained at the stage of hydrogenation is then separated by rectification into kerosene, as well as gasoline and diesel fractions, free of aromatic compounds. The iso-structure of the $C_{10}$-$C_{20}$ paraffins provides for producing kerosene and diesel demonstrating unique properties, as well as gasoline with octane number RON of at least 95 and an octane number MON of at least 91. Results of the studies by using chromatography-mass spectroscopy demonstrate that the kerosene obtained from tert-amyl alcohol contains 45 different $C_{10}$-$C_{15}$ isomers and is free of linear hydrocarbons. Kerosene, obtained from tert-amyl alcohol, does not freeze at minus 85° C., and has a Smoke point of 33 millimeters.

Example 15. Obtaining Kerosene from 2-Methyl-1-Pentanol 2-methyl pentyl alcohol is dehydrated in contact with the catalyst gamma $Al_2O_3$ at a temperature of 350 to 450° C. and a pressure of 1.0 to 2.0 MPa. The hexenes ($C_6H_{12}$) obtained by dehydration of alcohol are separated from water and supplied at a temperature of 250 to 350° C. and a pressure of 3.0 to 5.0 MPa into a continuous flow reactor, equipped with the catalyst containing at least 95% of ZSM-5 zeolite modified by 3.5-5.0% Zn and 0.1-1.5% Ce. Oligomerization of the source hexenes yielding $C_{12}$-$C_{24}$ olefins is performed in the presence of the said catalyst at the specified process parameters. The unreacted hexenes are distilled off the reaction mixture and returned back to the process. The reaction mass, free of the source hexenes, is directed for hydrogenation to a continuous flow reactor, equipped with the catalyst consisting of the oxides NiO, CuO, and $Cr_2O_3$ in a molar ratio of 1:1:1. Simultaneously with the $C_{12}$-$C_{24}$ olefins, hydrogen at a temperature of 120 to 150° C. and a pressure of 4.0 to 5.0 MPa is supplied to the hydrogenation reactor. The $C_{12}$-$C_{24}$ olefins obtained at the oligomerization stage are converted into $C_{12}$-$C_{24}$ paraffins. The yield of $C_{12}$-$C_{24}$ paraffins in terms of oligomerized hexenes is above 98%. The reaction mass obtained at the stage of hydrogenation is directed to rectification, where it is separated into kerosene and diesel fractions.

Example 16. Obtaining Kerosene from Terthexyl Alcohol

Terthexyl alcohol (3-methyl-3-pentanol) is dehydrated in contact with the catalyst gamma $Al_2O_3$ at a temperature of 100-150° C. and a pressure of 1.0 to 2.0 MPa. The hexenes ($C_6H_{12}$) formed are separated from water and supplied at a temperature of 100-150° C. and a pressure of 1.0 to 2.0 MPa into a continuous flow reactor, equipped with an ion-exchange resin in the form of a cation exchanger Amberlite 15, as the catalyst. Oligomerization of the source hexenes yielding $C_{12}$-$C_{18}$ olefins is carried out in the presence of the ion-exchange resin in the form of a cation exchanger Amberlite 15 as the catalyst at the specified process parameters. Unreacted hexenes are distilled off the reaction mass obtained by oligomerization and returned back to the process. The reaction mass, free of the source hexenes, is supplied for hydrogenation to a continuous flow reactor, equipped with the catalyst consisting of the oxides NiO, CuO, and $Cr_2O_3$ in a molar ratio of 1:1:1. Simultaneously with the $C_{12}$-$C_{18}$ olefins, hydrogen is supplied to the hydrogenation reactor at a temperature of 120 to 150° C. and a pressure of 4.0 to 5.0 MPa. The $C_{12}$-$C_{18}$ olefins obtained at the stage of oligomerization are hydrogenated into $C_{12}$-$C_{18}$ paraffins. The mixture of $C_{12}$-$C_{18}$ paraffins thus obtained is a kerosene fraction, free of aromatic compounds. The yield of $C_{12}$-$C_{18}$ paraffins, in terms of oligomerized hexenes, exceeds 98%. Results of the studies, performed by using chromatography-mass spectroscopy, demonstrate that kerosene, obtained from tert-hexyl alcohol, contains 48 different $C_{12}$-$C_{18}$ isomers and is free of linear hydrocarbons.

Example 17. Obtaining Kerosene from 3-Ethyl-3-Pentanol 3-ethyl-3-pentanol is dehydrated in contact with the catalyst gamma $Al_2O_3$ at a temperature of 100-150° C. and a pressure of 1.0 to 2.0 MPa. The heptenes ($C_7H_{14}$) obtained are separated from water and supplied at a temperature of 100-150° C. and a pressure of 1.0 to 2.0 MPa into a continuous flow reactor, equipped with an ion-exchange resin in the form of a cation exchanger Amberlite 15, as catalyst. Oligomerization of the source heptenes is carried out in the presence of the ion-exchange resin in the form of a cation exchanger Amberlite 15 catalyst with the specified process parameters, to yield $C_{14}$-$C_{21}$ olefins. Unreacted heptenes are distilled off the reaction mass obtained by oligomerization and returned back to the process. The reaction mass, free of the source heptenes, is supplied for hydrogenation in a continuous flow reactor, equipped with the catalyst consisting of the oxides NiO, CuO, and $Cr_2O_3$ in a molar ratio of 1:1:1. Simultaneously with the $C_{14}$-$C_{21}$ olefins, hydrogen is supplied to the hydrogenation reactor at a temperature of 120 to 150° C. and a pressure of 4.0 to 5.0 MPa. The $C_{14}$-$C_{21}$ olefins obtained at the oligomerization stage are hydrogenated into $C_{14}$-$C_{21}$ paraffins. The reaction mass obtained at the stage of hydrogenation is directed to rectification, and is separated into kerosene and diesel fractions, free from aromatic compounds. The yield of $C_{12}$-$C_{18}$ paraffins, in terms of oligomerized hexenes, exceeds 98%. Results of the studies, performed by using chromatography-mass spectroscopy, demonstrate that kerosene, obtained from tert-hexyl alcohol, contains 48 different $C_{12}$-$C_{18}$ isomers and is free of linear hydrocarbons.

Example 18. Obtaining Kerosene from Tert-Heptyl Alcohol

2-Methyl-hexanol-2 (dimethyl butyl carbinol) is dehydrated in contact with the catalyst gamma $Al_2O_3$ at a temperature of 100-150° C. and a pressure of 1.0 to 2.0 MPa. The obtained heptenes ($C_7H_{14}$) are separated from water and supplied at a temperature of 100-150° C. and a pressure of 1.0 to 2.0 MPa into a continuous flow reactor, equipped with the catalyst, an ion-exchange resin in the form of a cation exchanger Amberlite 15. These conditions provide for oligomerization of heptenes yielding $C_{14}$-$C_{21}$ olefins. The unreacted heptenes are distilled off the reaction mass obtained in the process of oligomerization and returned back to the process. The reaction mass, free from the source heptenes, is supplied for hydrogenation to a continuous flow reactor, equipped with the catalyst consisting of the oxides NiO, CuO, and $Cr_2O_3$ in a molar ratio of 1:1:1. Simultaneously with the oligomerization products, that is the $C_{14}$-$C_{21}$ olefins, hydrogen at a temperature of 120 to 150° C. and a pressure of 4.0 to 5.0 MPa is supplied into the hydrogenation reactor. The $C_{14}$-$C_{21}$ olefins obtained at the oligomerization stage are converted into $C_{14}$-$C_{21}$ paraffins. The reaction mass obtained at the stage of hydrogenation is directed to rectification, and is separated into kerosene and diesel fractions, free of aromatic compounds. The yield of $C_{14}$-$C_{21}$ paraffins, in terms of oligomerized heptenes, exceeds 95%. Results of the studies, performed by using chromatography-mass spectroscopy, demonstrate that kerosene, obtained from terthepptyl alcohol, contains 28 different $C_{14}$-$C_{18}$ isomers and is free of linear hydrocarbons.

Example 19. Obtaining Kerosene from 2-Ethyl-Hexyl Alcohol 2-ethyl-hexyl alcohol (2-ethyl-hexanol-1) is dehydrated in contact with the catalyst gamma $Al_2O_3$ at a temperature of 350 to 400° C. and a pressure of 0.5 to 2.0 MPa to yield octenes. The octenes ($C_8H_{16}$) are separated from water and supplied at a temperature of 150 to 200° C. and a pressure of 1.0 to 2.0 MPa into a continuous flow reactor, equipped with the granular catalyst containing at least 95% of ZSM-5 zeolite modified by 3.5-5.0% Zn and 0.1-1.5% Ce. These conditions provide for oligomerization of octenes to yield $C_{16}$-$C_{24}$ olefins. Unreacted octenes are distilled off from the reaction mass obtained by oligomerization and returned back to the process. The reaction mass, free of the source octenes, is supplied for hydrogenation to a continuous flow reactor, equipped with the catalyst consisting of the oxides NiO, CuO, and $Cr_2O_3$ in a molar ratio of 1:1:1. Simultaneously with the $C_{16}$-$C_{24}$ olefins, hydrogen is supplied into the hydrogenation reactor at a temperature of 250 to 350° C. and a pressure of 4.0 to 5.0 MPa. The $C_{16}$-$C_{24}$ olefins obtained at the oligomerization stage are hydrogenated into $C_{16}$-$C_{24}$ paraffins. The yield of $C_{16}$-$C_{24}$ paraffins, in terms of oligomerized octenes, exceeds 95%. Then the reaction mass obtained at the stage of hydrogenation is separated by rectification into kerosene and diesel fractions. Aromatic compounds content in these fractions does not exceed 5.0% mass.

Example 20. Obtaining Kerosene from a Mixture of Tert-Amyl and Tert-Hexyl Alcohols A mixture of tert-amyl and tert-hexyl alcohols in a molar ratio of 1:1 is dehydrated in contact with the catalyst gamma $Al_2O_3$ at a temperature of 100-150° C. and a pressure of 1.0 to 2.0 MPa. The resulting mixture of olefins ($C_5H_{10}$+$C_6H_{12}$) is separated from water and supplied at a temperature of 100 to 150° C. and a pressure of 1.0 to 2.0 MPa into a continuous flow reactor, equipped with the ion-exchange resin in the form of a cation exchanger Amberlite 15, as catalyst. These conditions provide for oligomerization of pentenes and hexenes to yield $C_{10}$-$C_{24}$ olefins.

The unreacted pentenes and hexenes are distilled off from the reaction mass obtained by oligomerization and returned back to the process. The reaction mass, free of the source pentenes and hexenes, is supplied for hydrogenation to a continuous flow reactor, equipped with the catalyst consisting of the oxides NiO, CuO, and $Cr_2O_3$ in a molar ratio of 1:1:1. Simultaneously with the products of oligomerization, hydrogen at a temperature of 120 to 150° C. and a pressure of 4.0 to 5.0 MPa is supplied to the hydrogenation reactor. The unsaturated $C_{10}$-$C_{24}$ compounds obtained at the oligomerization stage are hydrogenated into $C_{10}$-$C_{24}$ paraffins. After that the reaction mass obtained at the stage of hydrogenation is separated by rectification into kerosene, as well as gasoline and diesel fraction, free of aromatic compounds.

The yield of $C_{10}$-$C_{24}$ paraffins, in terms of oligomerized pentenes and hexenes, exceeds 99%. Results of the studies, performed by using chromatography-mass spectroscopy, demonstrate that kerosene, obtained from tert-amyl and tert-hexyl alcohols, contains 78 different $C_{10}$-$C_{20}$ isomers and is free of linear hydrocarbons.

Example 21. Obtaining Kerosene from a Mixture of Tert-Amyl, Tert-Hexyl and Tert-Heptyl Alcohols A mixture of tert-amyl, tert-hexyl and tert-heptyl alcohols in a molar ratio of 1:1:1 is dehydrated in contact with the catalyst gamma $Al_2O_3$ at a temperature of 100-150° C. and a pressure of 1.0 to 2.0 MPa. The resulting mixture of olefins ($C_5H_{10}$+$C_6H_{12}$+$C_7H_{14}$) is separated from water and supplied at a temperature of 100 to 150° C. and a pressure of 1.0 to 2.0 MPa into a continuous flow reactor, equipped with the ion-exchange resin in the form of a cation exchanger Amberlite 15, as catalyst. These conditions provide for oligomerization of pentenes, hexenes and heptenes to yield $C_{10}$-$C_{24}$ olefins. The unreacted pentenes, hexenes and heptenes are distilled off from the reaction mass obtained by oligomerization and returned back to the process. The reaction mass, free of the source pentenes, hexenes and heptenes, is directed for hydrogenation to a continuous flow reactor, equipped with the catalyst consisting of the NiO, CuO, and $Cr_2O_3$ in a molar ratio of 1:1:1. Simultaneously with the products of oligomerization, hydrogen at a temperature of 120 to 150° C. and a pressure of 4.0 to 5.0 MPa is supplied to the hydrogenation reactor. The unsaturated $C_{10}$-$C_{24}$ compounds obtained at the oligomerization stage are hydrogenated into $C_{10}$-$C_{24}$ paraffins. After that, the reaction mass obtained at the stage of hydrogenation is separated by rectification into $C_{11}$-$C_{18}$ kerosene, and $C_{19}$-$C_{24}$ diesel fractions, free of aromatic compounds. The yield of $C_{10}$-$C_{24}$ paraffins, in terms of oligomerized $C_5$-$C_7$ olefins, exceeds 99%. Results of the studies, performed by using chromatography-mass spectroscopy, demonstrate that kerosene, obtained from tert-amyl, tert-hexyl, and tert-heptyl alcohols, contains 101 different $C_{10}$-$C_{20}$ isomers and is free of linear hydrocarbons.

Example 22. Obtaining Kerosene from a Mixture of Propyl and 2-Methyl Pentyl Alcohols A mixture of propyl and 2-methyl pentyl alcohols in a molar ratio (1.0-1.5): 1 is dehydrated in contact with the catalyst gamma $Al_2O_3$ at a temperature of 350 to 450° C. and a pressure of 1.0 to 2.0 MPa. The resulting mixture of olefins ($C_3H_{6+}$ $C_6H_{12}$) is separated from water and supplied at a temperature of 250 to 350° C. and a pressure of 3.0 to 5.0 MPa into a continuous flow reactor, equipped with the granular catalyst containing at least 95% of ZSM-5 zeolite modified by 3.5-5.0% Zn and 0.1-1.5% Ce. These conditions provide for oligomerization of propylene and hexenes to yield $C_6$-$C_{24}$ olefins. The unreacted propylene and hexenes are distilled off from the reaction mass obtained by oligomerization and returned back to the process. The reaction mass, free from the source propylene and hexenes, is supplied for hydrogenation to a continuous flow reactor, equipped with the catalyst consisting of the NiO, CuO, and $Cr_2O_3$ in a molar ratio of 1:1:1. Simultaneously with the oligomerization products, hydrogen at a temperature of 120-150° C. and a pressure of 4.0-5.0 MPa is supplied to the hydrogenation reactor. The unsaturated $C_6$-$C_{24}$ compounds obtained at the oligomerization stage are hydrogenated into $C_6$-$C_{24}$ paraffins. The reaction mass obtained at the stage of hydrogenation is then separated by rectification into $C_{11}$-$C_{18}$ kerosene, as well as $C_6$-$C_{10}$ gasoline and $C_{19}$-$C_{24}$ diesel fractions, with aromatic compounds content of not more than 5.0% mass.

Example 23. Obtaining Kerosene from a Mixture of Propyl, Isobutyl, 2-Methyl Pentyl and 2-Ethyl Hexyl Alcohols A mixture of propyl, isobutyl, 2-methyl pentyl and 2-ethyl hexyl alcohols in a molar ratio of (1.0-1.5):1:1:(1.0-1.5) is dehydrated in contact with the catalyst gamma $Al_2O_3$ at a temperature of 350 to 450° C. and a pressure of 1.0 to 2.0 MPa. The resulting mixture of olefins ($C_3H_{6+}$ $C_4H_8$ +$C_6H_{12}$+$C_8H_{16}$) is separated from water and directed at a temperature of 250 to 350° C. and a pressure of 3.0 to 5.0 MPa into a continuous flow reactor, equipped with the granular catalyst containing at least 95% of ZSM-5 zeolite modified by 3.5-5.0% Zn and 0.1-1.5% Ce. These conditions provide for oligomerization of propylene, isobutylene, iso-hexenes and isooctenes to yield $C_6$-$C_{24}$ olefins. The unreacted propylene and isobutylene are distilled off from the reaction mass obtained by oligomerization and returned back to the process. The reaction mass, free from the source propylene and isobutylene, is supplied for hydrogenation to a continuous flow reactor, equipped with the catalyst consisting of the oxides NiO, CuO, and $Cr_2O_3$ in a molar ratio of 1:1:1. Simultaneously with the oligomerization products, hydrogen at a temperature of 120 to 200° C. and a pressure of 4.0 to 5.0 MPa is supplied to the hydrogenation reactor. The unsaturated $C_6$-$C_{24}$ compounds obtained at the oligomerization stage are hydrogenated into $C_6$-$C_{24}$ paraffins. Said $C_6$-$C_{24}$ paraffins are separated by rectification into $C_{11}$-$C_{18}$ kerosene, $C_6$-$C_{10}$ gasoline and $C_{19}$-$C_{24}$ diesel fractions. Tables 3, 4, and 5 demonstrate the properties of the hydrocarbon fractions obtained by the inventive process and having an aromatic compound content of not more than 5% mass. The yield of $C_6$-$C_{24}$ paraffins, in terms of oligomerized $C_3$-$C_8$ olefins, exceeds 99%.

Results of the studies, performed by using chromatography-mass spectroscopy, demonstrate that kerosene, obtained from propyl, isobutyl, 2-methyl pentyl and 2-ethyl hexyl alcohols, contains 134 different $C_8$-$C_{18}$ isomers, wherein 4.2% mass of those are linear hydrocarbons.

TABLE 3

| | | | | Result for gasoline of |
|---|---|---|---|---|
| Property | Method | Unit | Limit | Example 23 |
| Research octane number RON | EN ISO 5164 | | Min 95 | 96.5 |
| Motor octane number MON | EN ISO 5163 | | Min 85 | 92.3 |
| Distillation: | | | | |
| Initial Boiling Point IBP | EN ISO 3405 | ° C. | Min 30 | 30.6 |
| % vol recovered at 70 C. | EN ISO 3405 | % vol | 20-52 | 22.6 |
| % vol recovered at 100 C. | EN ISO 3405 | % vol | 46-72 | 46.8 |
| % vol recovered at 150 C. | EN ISO 3405 | % vol | Min 75 | 85.7 |
| Final Boiling Point FBP | EN ISO 3405 | ° C. | Max 210 | 180.8 |
| Residue | EN ISO 3405 | % vol | Max 2.0 | 1.2 |
| Saturated vapour pressure | EN 13016 | kPa | Min 45 Max 100 | 56.7 |
| Density at 15° C. | EN ISO 3675 | kg/m$^3$ | 720-775 | 731.6 |
| Olefins | EN ISO 22854 | % vol | Max 18.0 | <0.3 |
| Benzene | EN ISO 22854 | % vol | Max 1.0 | <0.1 |
| Aromatic hydrocarbon | EN ISO 22854 | % vol | Max 35 | <0.5 |
| Oxygen | EN ISO 22854 | % mass | Max 3.7 | <0.1 |
| Copper strip corrosion | EN ISO 2160 | rating | class 1 | 1A |
| Sulphur | EN ISO 20846 | mg/kg | Max 10.0 | <0.1 |
| Gum, Existent Unwashed | EN ISO 6246 | mg/100 ml | Max 5 | 1.5 |
| Gum, Existent Solvent Washed | EN ISO 6246 | mg/100 ml | Max 5 | <1.0 |

Properties of gasoline of Example 23.

TABLE 4

| | | | | Result for Jet of Example 23 |
|---|---|---|---|---|
| Property | Method | Unit | Limit | |
| Acid Number | ASTM D 3242 | mg KOH/g | Max 0.015 | 0.004 |
| Density at 15° C. | ASTM D 4052 | kg/m³ | 775-840 | 780.6 |
| Mono-Aromatics Content | ASTM D 6379 | % vol | Min 8 Max 25 | <1.0 |
| Poly Aromatic Content | EN 12916 | % W/W | | <0.1 |
| Olefines | ASTM D 1319 | % vol | | 1.0 |
| Distillation IBP | ASTM D 86 | ° C. | | 168.5 |
| Temperature @ 10% rec. | ASTM D 86 | ° C. | Max 205 | 179.6 |
| Temperature @ 20% rec. | ASTM D 86 | ° C. | | 192.4 |
| Temperature @ 50% rec. | ASTM D 86 | ° C. | | 203.9 |
| Temperature @ 90% rec. | ASTM D 86 | ° C. | | 234.4 |
| Distillation FBP | ASTM D 86 | ° C. | Max 300 | 241.4 |
| Residue | ASTM D 86 | % vol | Max 1.5 | 1.1 |
| Loss | ASTM D 86 | % vol | Max 1.5 | 0.6 |
| Sulphur Content | ASTM D 5453 | mg/kg | Max 0.3 | <0.1 |
| Flash Point Abel | IP 170 | ° C. | Min 38 | 53.5 |
| Freezing Point | ASTM D 2386 | ° C. | Max minus 47 | <minus 85 |
| Gum, Existent | ASTM D 381 | mg/100 ml | Max 7 | <0.1 |
| Smoke Point | ASTM D 1322 | mm | Min 25 | 32.0 |
| Water Reaction | ASTM D 1094 | | | 1b |
| Water Separation Index (MSEP) | ASTM D 3948 | | Min 85 | 92 |
| Particulate Contaminant Lab. Test | ASTM D 5452 | mg/l | Max 10 | 0.72 |
| Copper strip corrosion | ASTM D 130 | 2 h/100° C. | class 1 | 1A |
| Color (Saybolt) | ASTM D 156 | | Min 25 | 30 |
| Conductivity (no antistatic agent) | ASTM D 2624 | pS/m | Max 600 | <1 |
| JFTOT 260° C., 2.5 h | ASTM D 3241 | mmHg | Max 25 | <1 |
| JFTOT | ASTM D 3241 | Rating | Max 85 | 41 |
| JFTOT | ASTM D 3241 | ml | | 460 |
| JFTOT | ASTM D 3241 | ° C. | Min 325 | 325 |
| BOCLE | ASTM D 5001 | WSD mm | Max 0.85 | 0.67 |
| Specific Energy | ASTM D 3338 | MJ/kg | Min 42.8 | 43.86 |
| Viscosity@−20° C. | ASTM D 445 | mm²/s | Max 8.0 | 5.631 |

TABLE 5

| | | | | Result for diesel of Example 23 |
|---|---|---|---|---|
| Property | Method | Unit | Limit | |
| Cetane Number | EN ISO 4264 | | Min 51 | 59.2 |
| Cetane Index (Calculated) | ISO 6245 | | Min 46 | 64.6 |
| Density at 15° C. | ISO 12185 | kg/m³ | 800-845 | 814.1 |
| Mono-Aromatics Content | SS-EN 12916 | % vol | Max 8.0 | 4.7 |
| Poly Aromatic Content | SS-EN 12916 | % vol | Max 8.0 | <0.02 |
| Fractional composition: | ISO 3405 | | | |
| recovered at 180° C., | ISO 3405 | % vol | Max 10 | <0.1 |

TABLE 5-continued

| | | | | Result for diesel of Example 23 |
|---|---|---|---|---|
| Property | Method | Unit | Limit | |
| recovered at 250° C., | ISO 3405 | % vol | Max 65 | 19.7 |
| recovered at 340° C., | ISO 3405 | % vol | Min 95 | >98.0 |
| 95% vol. recovered at temperature | ISO 3405 | ° C. | Max 360 | 291.6 |
| Sulphur content | ISO 20846 | mg/kg | Max 10 | 3 |
| Flash point | EN ISO 2719 | ° C. | Min 55 | 88.0 |
| Ash content | ISO 6245 | % mass | Max 0.010 | 0.001 |
| Water content | EN ISO 12937 | % mass | Max 0.020 | 0.0028 |
| Particulate matter | EN 12662 | mg/kg | Max 24 | 6.5 |
| Copper strip corrosion | ASTM D | rating | class 1 | 1A |
| Cold Filtration Plugging Point | EN 116 | ° C. | Max minus 44 | minus 48 |
| Cloud point | EN 23015 | ° C. | Max minus 34 | <minus 52 |
| Viscosity@ 40° C., | ISO 3104 | MM2/c | 1.500-4.000 | 3.000 |
| Oxidation Stability 20 h | ISO 12205 | g/m³ | Max 25 | 2 |
| HERR Wear Scar (Lubricity) | ISO 12156 | μm | Max 460 | 443 |

Example 24. Obtaining Tertamyl Ethyl Ether from Tert-Amyl and Ethyl Alcohols

Tert-amyl alcohol (2-methyl-2-butanol) produced on the basis of the inventive technology is dehydrated in contact with the catalyst gamma $Al_2O_3$ at a temperature of 100-150° C. and a pressure of 1.0 to 2.0 MPa. The obtained pentenes ($C_5H_{10}$) are separated from water, mixed with ethyl alcohol ($C_2H_5OH$) in a molar ratio of 1:(1.1-1.5) and supplied at a temperature of 50 to 100° C. and a pressure of 0.5-1.0 MPa to a continuous flow reactor, equipped with the ion-exchange resin in the form of a cation exchanger Amberlite 15, as catalyst. The load on the catalyst is 0.5 to 1.0 liters of a solution of pentenes in ethyl alcohol per 1.0 liter of catalyst, the contact time of a solution of pentenes in ethyl alcohol with the ion-exchange resin in the form of a cation exchanger Amberlite 15, as catalyst is 30 to 60 minutes. The reaction mass obtained at the stage of etherification is directed to rectification, where ethyl alcohol is separated from ethyl tert-amyl ether. The rate of conversion of pentenes into ethyl tert-amyl ether exceeds 99%. The unreacted ethyl alcohol is returned back to the process to the stage of mixing with pentenes. Tert-amyl ethyl ether is used to obtain a standard gasoline free of aromatics.

Example 25. Obtaining a Standard Gasoline Containing Ethers

To obtain a standard gasoline free of aromatic compounds, the gasoline fraction of paraffins, produced on the basis of the inventive technology was used, and tertamyl ethyl ether, produced by the method of the previous example. The gasoline fraction of paraffins, containing $C_3$-$C_{10}$ hydrocarbons, is mixed with tertamyl ethyl ether in any volume ratio that does not violate the limits for oxygen content in gasoline prescribed by the relevant standards. Concentrations of 15%-22% by volume of tertamyl ethyl ether in the final mixture with $C_3$-$C_{10}$ paraffins are preferred for gasolines produced by the inventive technology. Table 6 shows the main properties of gasoline that is free of aromatic compounds. Gasoline prepared from the gasoline fraction of paraffins and tertamyl ethyl ether, produced on the basis of the inventive technology, is characterized by high octane numbers. A content of 20.0% by volume of tertamyl ethyl ether and 80.0% by volume of the gasoline fraction, as shown in the Example 23, provides the octane number RON=100.9 MON=93.8. The oxygen content of such gasoline is less than 3.0% wt.

TABLE 6

Properties of gasoline of Example 25.

| Property | Metod | Unit | Limit | Result for gasoline of Example 25 |
|---|---|---|---|---|
| Research octane number RON | EN ISO 5164 | | Min 95 | 100.9 |
| Motor octane number MON Distillation: | EN ISO 5163 | | Min 85 | 93.8 |
| Initial Boiling Point IBP | EN ISO 3405 | ° C. | Min 30 | 32.4 |
| % vol recovered at 70 C. | EN ISO 3405 | % vol | 10-50 | 25.4 |
| % vol recovered at 100 C. | EN ISO 3405 | % vol | 35-71 | 37.8 |
| % vol recovered at 150 C. | EN ISO 3405 | % vol | Min 60 | 83.3 |
| Final Boiling Point FBP | EN ISO 3405 | ° C. | Max 210 | 177.5 |
| Residue | EN ISO 3405 | % vol | Max 2.0 | 1.1 |
| Saturated vapour pressure | EN 13016 | kPa | Min 45 Max 100 | 59.0 |

TABLE 6-continued

Properties of gasoline of Example 25.

| Property | Metod | Unit | Limit | Result for gasoline of Example 25 |
|---|---|---|---|---|
| Density at 15° C. | EN ISO 3675 | kg/m$^3$ | 720-775 | 737.3 |
| Olefins | EN ISO 22854 | % vol | Max 18.0 | <0.1 |
| Benzene | EN ISO 22854 | % vol | Max 1.0 | <0.1 |
| Aromatic hydrocarbon | EN ISO 22854 | % vol | Max 35 | <0.5 |
| Oxygen | EN ISO 22854 | % mass | Max 3.7 | 2.99 |
| Copper strip corrosion | EN ISO 2160 | rating | class 1 | 1A |
| Sulphur | EN ISO 20846 | mg/kg | Max 10.0 | <0.1 |
| Gum, Existent Unwashed | EN ISO 6246 | mg/100 ml | Max 5 | 0.6 |
| Gum, Existent Solvent Washed | EN ISO 6246 | mg/100 ml | Max 5 | <0.5 |

Example 26. Obtaining Ethers from Tertiary $C_5$-$C_6$ Alcohols and Ethanol

A mixture of tertiary $C_5$-$C_8$ alcohols, obtained by telomerization, were sent to rectification for isolation of tertiary $C_5$-$C_6$ alcohols. The $C_5$-$C_6$ tertiary alcohols were then dehydrated to yield the corresponding $C_5$-$C_6$ olefins. The obtained $C_5$-$C_6$ olefins were cooled and supplied at a temperature of 50 to 100° C. and a pressure of 0.5-1.0 MPa into a continuous flow reactor, equipped with the ion-exchange resin in the form of a cation exchanger Amberlite 15, as catalyst. Along with $C_5$-$C_6$ olefins, ethyl alcohol was supplied to the reactor in a molar ratio $(C_5H_{10}+C_6H_{12})$: $C_2H_5OH=1:(1.0-1.1)$. The contact time of the $C_5$-$C_6$ olefin solution in ethyl alcohol with the ion-exchange resin in the form of a cation exchanger Amberlite 15, as catalyst is 30 to 60 minutes. The reaction mass obtained at the stage of etherification is sent to rectification for separation of the unreacted ethyl alcohol from tertamyl ethyl and terthexyl ethyl ethers. The rate of conversion of $C_5$-$C_6$ olefins into ethyl tertamyl and ethyl terthexyl ethers exceeds 99%. The unreacted in the etherification reaction ethyl alcohol is returned back to the process to the stage of mixing with $C_5$-$C_6$ olefins. Ethyl tertamyl and ethyl terthexyl ethers are used for producing gasoline with an octane number of at least 100.

Example 27. Obtaining Gasoline with Octane Number of at Least 100 and Oxygen Content of not more than 2.7% Mass To produce gasoline with an octane number of at least 100 and an oxygen content of not higher than 2.7% mass, it is necessary to use $C_3$-$C_{10}$ gasoline fraction of paraffins, obtained by the inventive technology, as well as tertamyl ethyl and terthexyl ethyl ethers, obtained as described in the previous Example. Furthermore, to produce gasoline with an octane number of at least 100 and an oxygen content of not more than 2.7 wt %, it is necessary to use $C_7$-$C_9$ aromatic compounds obtained by the inventive technology. The gasoline fraction of paraffins, containing $C_3$-$C_{10}$ hydrocarbons, is mixed with tertamyl ethyl and terthexyl ethyl ethers in any volume ratio, which does not violate limits on oxygen content in gasoline stipulated by the relevant standard EN228. Preferred volumetric concentrations for gasolines with an octane number of at least 100 are 15%-25% of tertamyl ethyl and terthexyl ethyl ethers in the final composition with $C_3$-$C_{10}$ paraffins and $C_7$-$C_9$ aromatics.

Table 7 shows main properties of gasoline with an octane number of at least 100 and an oxygen content of not more than 2.7% mass.

TABLE 7

Properties of gasoline of Example 27.

| Property | Method | Unit | Limit | Result for gasoline of Example 27 |
|---|---|---|---|---|
| Research octane number RON | EN ISO 5164 | | Min 95 | 100.1 |
| Motor octane number MON | EN ISO 5163 | | Min 85 | 93.6 |
| Distillation: | | | | |
| Initial Boiling Point IBP | EN ISO 3405 | ° C. | Min 30 | 36.4 |
| % vol recovered at 70 C. | EN ISO 3405 | % vol | 10-50 | 17.9 |
| % vol recovered at 100 C. | EN ISO 3405 | % vol | 35-71 | 42.7 |
| % vol recovered at 150 C. | EN ISO 3405 | % vol | Min 60 | 84.1 |
| Final Boiling Point FBP | EN ISO 3405 | ° C. | Max 210 | 178.4 |
| Residue | EN ISO 3405 | % vol | Max 2.0 | 1.2 |
| Saturated vapour pressure | EN 13016 | kPa | 45-100 | 58.0 |
| Density at 15° C. | EN ISO 3675 | kg/m$^3$ | 720-775 | 757.6 |
| Olefins | EN ISO 22854 | % vol | Max 18.0 | <0.1 |
| Benzene | EN ISO 22854 | % vol | Max 1.0 | <0.1 |
| Aromatic hydrocarbon | EN ISO 22854 | % vol | Max 35 | 7.5 |
| Oxygen | EN ISO 22854 | % mass | Max 2.7 | 2.65 |
| Copper strip corrosion | EN ISO 2160 | rating | class 1 | 1A |
| Sulphur | EN ISO 20846 | mg/kg | | <0.1 |

TABLE 7-continued

| | | Properties of gasoline of Example 27. | | |
|---|---|---|---|---|
| Property | Method | Unit | Limit | Result for gasoline of Example 27 |
| Gum, Existent Unwashed | EN ISO 6246 | mg/100 ml | Max 5 | 0.6 |
| Gum, Existent Solvent Washed | EN ISO 6246 | mg/100 ml | Max 5 | <0.5 |

Example 28 Obtaining of Ethers from Tertiary $C_7$-$C_8$ Alcohols and N-Butyl Alcohols A mixture of tertiary $C_5$-$C_8$ alcohols, obtained by telomerization, was sent for rectification to isolate tertiary $C_7$-$C_8$ alcohols. The tertiary alcohols were then dehydrated to yield the corresponding $C_7$-$C_8$ olefins. The $C_7$-$C_8$ olefins thus obtained were cooled and supplied at a temperature of 50 to 100° C. and a pressure of 0.5-1.0 MPa into a continuous flow reactor, where the ion-exchange resin in the form of a cation exchanger Amberlite 15, as catalyst was loaded. Along with the $C_7$-$C_8$ olefins, n-butyl alcohol, obtained by the inventive technology, was supplied into the reactor in a molar ratio $(C_7H_{14}+C_8H_{16}):C_4H_9OH=1:(1.0-1.1)$. The contact time of the $C_7$-$C_8$ olefin solution in n-butyl alcohol with the ion-exchange resin in the form of a cation exchanger Amberlite 15, as catalyst, is 30 to 60 minutes. The reaction mass obtained in the etherification process was directed to rectification, where n-butyl alcohol was separated from tert-heptyl butyl and tert-octyl butyl ethers. The rate of $C_7$-$C_8$ olefin conversion into tert-heptyl butyl and tert-octyl butyl ethers exceeds 99%. The unreacted in the etherification reaction butyl alcohol, is separated by rectification in the rectification column and returned back to the process to the stage of mixing with $C_7$-$C_8$ olefins. Tert-heptyl butyl and tert-octyl butyl ethers are used to produce diesel, containing oxygenated hydrocarbons.

Example 29. Producing a Standard Diesel Fuel Containing Oxygenated Hydrocarbons To produce a standard diesel fuel comprising oxygen-containing hydrocarbons, it is necessary to use diesel fraction of $C_{19}$-$C_{24}$ paraffins, produced by the inventive technology. Furthermore, tert-heptyl butyl and tert-octyl butyl ethers shall be used as oxygen-containing hydrocarbons of this diesel fuel. The method for producing tert-heptyl butyl and tert-octyl butyl ethers is described in the previous example. The diesel fraction of paraffins, containing $C_{19}$-$C_{24}$ hydrocarbons, was mixed with tert-heptyl butyl and tert-octyl butyl ethers in any ratio that does not violate requirements of the relevant standards for diesel fuels. Preferred concentration for diesel fuels, produced by the inventive technology, is from 5% to 15% by volume of the total of tert-heptyl butyl and tert-octyl butyl ethers in the final mixture with $C_{19}$-$C_{24}$ paraffins. Table 8 shows main properties of the diesel fuel containing a mixture of tert-heptyl butyl and tert-octyl butyl ethers in the amount of 10% by vol. of the final mixture with $C_{19}$-$C_{24}$ paraffins.

TABLE 8

| | | Properties of diesel fuel of Example 29. | | |
|---|---|---|---|---|
| Property | Method | Unit | Limit | Result for diesel fuel of Example 29 |
| Cetane Number | EN ISO 4264 | | Min 51 | 54.6 |
| Cetane Index (Calculated) | ISO 6245 | | Min 46 | 61.7 |
| Density at 15° C. | ISO 12185 | kg/m$^3$ | 800-845 | 817.0 |
| Mono-Aromatics Content | SS-EN 12916 | % vol | Max 8.0 | 3.5 |
| Poly Aromatic Content | SS-EN 12916 | % vol | Max 8.0 | <0.01 |
| Fractional composition: | ISO 3405 | | | |
| recovered at 180° C., | ISO 3405 | % vol | Max 10 | <0.1 |
| recovered at 250° C., | ISO 3405 | % vol | Max 65 | 29.9 |
| recovered at 340° C., | ISO 3405 | % vol | Min 95 | >98 |
| 95% vol. recovered at a temperature | ISO 3405 | ° C. | Max 360 | 314.3 |
| Sulphur Content | ISO 20846 | mg/kg | Max 10 | <2 |
| Flash Point | EN ISO 2719 | ° C. | Min 55 | 88.5 |
| Ash Content | ISO 6245 | % mass | Max 0.01 | <0.001 |
| Water Content | EN ISO 12937 | % mass | Max 0.020 | 0.0102 |
| Particulate Matter | EN 12662 | mg/kg | Max 24 | 0.76 |
| Copper strip corrosion | ASTM D | rating | class 1 | 1A |
| Cold Filtration Plugging Point | EN 23015 | ° C. | Max minus 32 | minus 33 |
| Cloud Point | EN 116 | ° C. | Max minus 22 | minus 31 |
| Viscosity@ 40° C., | ISO 3104 | MM2/c | 1.500-4.000 | 2.852 |
| Oxidation Stability 20 h | ISO 12205 | g/m$^3$ | Max 25 | 18 |
| HERR Wear Scar (Lubricity) | ISO 12156 | μm | Max 460 | 396 |

53

Example 30. Producing Ethers from Tertiary $C_7$-$C_8$ Alcohols and 2-Ethyl Hexyl Alcohol A mixture of tertiary $C_5$-$C_8$ alcohols, obtained by telomerization, was sent to rectification to isolate the tertiary $C_7$-$C_8$ alcohols. The isolated alcohols were then dehydrated to obtain the corresponding $C_7$-$C_8$ olefins. The $C_7$-$C_8$ olefins obtained were cooled and supplied at a temperature of 50 to 100° C. and a pressure of 0.5 to 1.0 MPa to a continuous flow reactor, where the catalyst, which is an ion exchange resin, in this case the cation exchanger Amberlite 15, was loaded. Along with the $C_7$-$C_8$ olefins, 2-ethyl hexyl alcohol, obtained by the inventive technology, was supplied to the reactor in a molar ratio (C—$H_{14}$+$C_8H_{16}$):$C_8H_{17}$OH=1:(1.1-1.5). The contact time of the solution of $C_7$-$C_8$ olefins in 2-ethyl hexyl alcohol with the catalyst, which is an ion exchange resin, in this case the cation exchanger, is 45 to 60 minutes. The reaction mass obtained at the stage of etheri-

54 to produce said diesel fuel, it is necessary to use tert-heptyl butyl and tert-octyl butyl ethers, as well as tert-heptyl 2-ethyl hexyl and tert-octyl 2-ethyl hexyl ethers. Methods for producing said ethers are described in the Examples 28 and 30.

The paraffin fraction, containing $C_{19}$-$C_{24}$ hydrocarbons, was mixed with tert-heptyl butyl and tert-octyl butyl ethers, as well as tert-heptyl 2-ethyl hexyl and tert-octyl 2-ethyl hexyl ethers. The mixing was performed in a manner providing for compliance of the properties of the resulting hydrocarbon mixtures with the requirements of the current standards for diesel motor fuel. Preferred concentration for diesel fuels produced by the inventive technology and comprising said ethers is from 10% to 20% by volume of the total of all ethers in the final mixture with $C_{19}$-$C_{24}$ paraffins. Table 9 shows the main properties of diesel fuel, containing not less than 20% vol. of oxygen-containing hydrocarbons.

TABLE 9

| Properties of diesel fuel of Example 31 | | | | |
|---|---|---|---|---|
| Property | Method | Unit | Limit | Result for diesel fuel of Example 31 |
| Cetane Number | EN ISO 5165 | | Min 51 | 59.8 |
| Cetane Index (Calculated) | EN ISO 4264 | | Min 46 | 66.2 |
| Density at 15° C. | EN ISO 12185 | kg/m$^3$ | 820-845 | 820.8 |
| Mono-Aromatics Content | SS-EN 12916 | % vol | Max 8.0 | <0.1 |
| Carbon Residue Micro (10%) | ISO 10370 | % mass | Max 0.30 | <0.02 |
| Fractional composition: | EN ISO 3405 | | | |
| recovered at 250° C., | EN ISO 3405 | % vol | Max 65 | 33.3 |
| recovered at 350° C., | EN ISO 3405 | % vol | Min 85 | >98.5 |
| 95% vol. recovered at a temperature | EN ISO 3405 | ° C. | Max 360 | 314.8 |
| Sulphur Content | EN ISO 20846 | mg/kg | Max 10 | <2 |
| Flash Point | EN ISO 2719 | ° C. | Min 55 | 88.0 |
| Ash Content | EN ISO 6245 | % mass | Max 0.010 | <0.001 |
| Water Content | EN ISO 12937 | % mass | Max 0.020 | 11 |
| Particulate Matter | EN 12662 | mg/kg | Max 24 | 16 |
| Copper strip corrosion | EN ISO 2160 | rating | class 1 | 1A |
| Cold Filtration Plugging Point | EN 23015 | ° C. | Max minus 38 | minus 40 |
| Cloud Point | EN 116 | ° C. | Max minus 28 | minus 39 |
| Viscosity@ 40° C., | EN ISO 3104 | mm$^2$/c | 1.500-4.000 | 2.988 |
| Oxidation Stability 20 h | EN ISO 12205 | g/m$^3$ | Max 25 | 22 |
| HFRR Wear Scar (Lubricity) | ISO 12156 | μm | Max 460 | 419 | fication was directed to rectification, where 2-ethyl hexyl alcohol was separated from the obtained tert-heptyl 2-ethyl hexyl and tert-octyl 2-ethyl hexyl ethers. The rate of $C_7$-$C_8$ olefin conversion into tert-heptyl 2-ethyl hexyl and tert-octyl 2-ethyl hexyl ethers exceeds 90%. A mixture of 2-ethyl hexyl alcohol and unreacted $C_7$-$C_8$ olefins was isolated in the rectification column and returned back to the process to the etherification stage. Tert-heptyl 2-ethyl hexyl and tert-octyl 2-ethyl hexyl ethers are used to produce diesel fuel, comprising in the composition oxygen-containing hydrocarbons in an amount of not less than 20% vol.

Example 31. Producing Diesel Fuel, Comprising in the Composition Oxygen-Containing Hydrocarbons in the Amount of not Less than 20% Vol To produce diesel fuel comprising in the composition oxygen-containing hydrocarbons in the amount of not less than 20% vol., it is necessary to use the $C_{19}$-$C_{24}$ paraffin fraction obtained by the inventive technology. Furthermore,

Example 32. Obtaining a 100% Biological Kerosene from Ethanol, in Full Compliance of All Requirements of the Current Standard Jet A1

A mixture of tert-amyl, tert-hexyl, tert-heptyl and tert-octyl alcohols in a molar ratio of 1:1:1:1 is dehydrated in contact with the gamma $Al_2O_3$ catalyst at a temperature of 100 to 150° C. and a pressure of 1.0 to 2.0 MPa. The resulting mixture of olefins ($C_5H_{10}$+$C_6H_{12}$+$C_7H_{14}$+$C_8H_{16}$) is separated from water and supplied at a temperature of 100 to 150° C. and a pressure of 1.0 to 2.0 MPa to a continuous flow reactor, where the catalyst, which is an ion exchange resin, in this case the cation exchanger Amberlite 15, is loaded. Under these conditions, pentenes, hexenes, heptenes and octenes are oligomerized yielding $C_{10}$-$C_{24}$ olefins. The unreacted pentenes, hexenes, heptenes and octenes are distilled from the reaction mass obtained by oligomerization and returned back to the process. The reaction mass, free of the source pentenes, hexenes, heptenes and octenes, is directed for hydrogenation to a continuous flow reactor, where the catalyst consisting of the oxides NiO, CuO and $Cr_2O_3$ in a molar ratio of 1:1:1 is loaded. Along with the oligomerization products, hydrogen is supplied to the hydrogenation reactor at a temperature of 120 to 150° C. and a pressure of 4.0 to 5.0 MPa. In the course of hydrogenation, the unsaturated $C_{10}$-$C_{24}$ compounds obtained at the oligomerization stage are converted into $C_{10}$-$C_{24}$ paraffins. The pounds in such a way that the concentration of the aromatic hydrocarbons in the final composition of kerosene is in the range from 8% vol. to 25% vol. Table 10 shows the main properties of the 100% biological kerosene produced from ethanol, which is in full compliance with all requirements of the current standard Jet A1.

TABLE 10

| Properties of Jet of Example 32 | | | | |
|---|---|---|---|---|
| Property | Metod | Unit | Limit | Result for Jet of Example 32 |
| Acid Number | ASTM D 3242 | mg KOH/g | Max 0.015 | 0.007 |
| Density at 15° C. | ASTM D 4052 | kg/m³ | 775-840 | 789.5 |
| Mono-Aromatics Content | ASTM D 1319 | % volume | Min 8 Max 25 | 9.8 |
| Poly Aromatics Content | EN12916 | % W/W | | <0.1 |
| Olefines | ASTM D 1319 | % vol | | 1.8 |
| Distillation IBP | ASTM D 86 | ° C. | | 169.9 |
| Temperature @ 10% rec. | ASTM D 86 | ° C. | Max 205 | 183.1 |
| Temperature @ 20% rec. | ASTM D 86 | ° C. | | 187.2 |
| Temperature @ 50% rec. | ASTM D 86 | ° C. | | 201.4 |
| Temperature @ 90% rec. | ASTM D 86 | ° C. | | 223.0 |
| Distillation FBP | ASTM D 86 | ° C. | Max 300 | 235.3 |
| Residue | ASTM D 86 | % vol | Max 1.5 | 1.5 |
| Loss | ASTM D 86 | % vol | Max 1.5 | 0.2 |
| Sulphur Content | ASTM D 5453 | mg/kg | Max 0.3 | <0.1 |
| Flash Point Abel | ASTM D 56 | ° C. | Min 38 | 51.0 |
| Freezing Point | ASTM D 2386 | ° C. | Max minus 47 | <minus 85 |
| Gum, Existent | ASTM D 381 | mg/100 ml | Max 7 | <1 |
| Smoke Point | ASTM D 1322 | mm | Min 25 | 35 |
| Water Reaction | ASTM D 1094 | | | 1b |
| Water Separation Index (MSEP) | ASTM D 3948 | | Min 85 | 97 |
| Particulate Contaminant Lab. Test | ASTM D 5452 | mg/l | Max 10 | 0.36 |
| Copper strip corrosion | ASTM D 130 | 2 h/100° C. | class 1 | 1A |
| Color (Saybolt) | ASTM D 156 | | Min 25 | 30 |
| Conductivity (no antistatic agent) | ASTM D 2624 | pS/m | Max 600 | <1 |
| JFTOT 2.5 h 260° C. | ASTM D 3241 | mm Hg | Max 25 | <1 |
| JFTOT Rating | ASTM D 3241 | nm | Max 85 | 9 |
| JFTOT | ASTM D 3241 | ml | | 447 |
| JFTOT | ASTM D 3241 | ° C. | Min 325 | 325 |
| BOCLE | ASTM D 5001 | WSD mm | Max 0.85 | 0.69 |
| Specific Energy | ASTM D 3338 | MJ/kg | Min 42.8 | 43.75 |
| Viscosity@-20° C. | ASTM D 445 | mm²/s | Max 8.0 | 4.893 | reaction mass obtained at the stage of hydrogenation is directed to the rectification, where it is separated into kerosene and diesel fractions, free of aromatic compounds.

The unsaturated $C_2$-$C_5$ hydrocarbons obtained at the stage of dehydration of the corresponding $C_2$-$C_5$ alcohols are supplied to the aromatization reactor. Aromatization of the unsaturated hydrocarbons is carried out at a temperature of 350 to 450° C. and a pressure of 0.5 to 2.0 MPa in a continuous operation reactor in the presence of the inventive heterogeneous zeolite-containing catalyst, comprising at least 93% of ZSM-5 modified by 3.5 to 7.0% Zn. In the course of aromatization, the unsaturated $C_2$-$C_5$ hydrocarbons are converted into aromatic compounds $C_7$-$C_{12}$. The reaction mass obtained at the stage of aromatization is isolated from the gaseous products, which are a mixture of hydrogen and $C_1$-$C_4$ paraffins, and directed to rectification, where it is separated into two fractions:$C_7$-$C_8$ aromatic hydrocarbons and $C_9$-$C_{12}$ aromatic hydrocarbons. The $C_7$-$C_8$ aromatic hydrocarbons are used to produce gasoline, while the $C_9$-$C_{12}$ aromatic hydrocarbons are used to produce kerosene. The $C_{11}$-$C_{18}$ kerosene paraffins fraction isolated from $C_{10}$-$C_{24}$ paraffins is mixed with the aromatic com- Method 1: A method for producing from ethanol a motor fuel selected from gasoline, kerosene, and diesel may comprise the following interconnected steps:

step 1.1 converting a mixture of ethanol and water into:
isopropanol and $C_5$ alcohols;
acetaldehyde;
a mixture of $C_1$-$C_4$ paraffins and $C_2$-$C_4$ olefins;
a mixture of carbon dioxide and hydrogen;

step 1.2 converting the mixture of carbon dioxide and hydrogen, obtained in step 1.1, additional hydrogen, and a mixture of $C_1$-$C_4$ paraffins into synthesis gas;

step 1.3 converting ethanol, and $C_3$-$C_8$ alcohols, including $C_5$ alcohols obtained from step 1.1, into:$C_2$-$C_8$ olefins, including ethylene and propylene;

step 1.4 converting a mixture of unreacted ethanol from step 1.1, isopropanol obtained in step 1.1, ethylene obtained in step 1.3, using a telomerization reaction into secondary butanol and tertiary $C_5$-$C_8$ alcohols, the tertiary $C_8$ and $C_7$ alcohols being obtained from the isopropanol, and the tertiary $C_6$, and $C_8$ alcohols being obtained from the ethanol, wherein the resulting secondary butanol is directed to step 1.3;

step 1.5 converting the $C_5$-$C_8$ tertiary alcohols, obtained in step 1.4, by dehydration into $C_5$-$C_8$ olefins;

step 1.6 converting a first portion of the $C_5$-$C_8$ olefins, obtained in step 1.5, by oligomerization into $C_{10}$-$C_{24}$ olefins;

step 1.7 converting the $C_{10}$-$C_{24}$ olefins, obtained in step 1.6, by hydrogenation using hydrogen obtained from step 1.1, into $C_{10}$-$C_{24}$ paraffins;

step 1.8 converting the synthesis gas, obtained in step 1.2, ethylene obtained in step 1.3, propylene obtained in step 1.3, and the acetaldehyde, obtained in step 1.1, by hydroformylation and aldol condensation into a mixture of $C_3$-$C_4$ aldehydes and $C_5$-$C_8$ aldols, said mixture of $C_3$-$C_4$ aldehydes and $C_5$-$C_5$ aldols is thereafter hydrogenated to obtain $C_3$-$C_8$ alcohols, which alcohols are directed to step 1.3 to obtain $C_3$-$C_8$ olefins, wherein the acetaldehyde produces $C_8$ alcohol, the ethylene from step 1.3 produces $C_3$ and $C_6$ alcohols, and the propylene from step 1.3 produces $C_4$ and $C_8$ alcohols; and wherein the ethylene and the propylene from step 1.3 produce $C_7$ alcohol;

step 1.9 converting the $C_2$-$C_8$ olefins from step 1.3, by oligomerization into $C_6$-$C_{24}$ olefins;

step 1.10 converting the $C_6$-$C_{24}$ olefins, obtained in step 1.9, and hydrogen, by hydrogenation into $C_6$-$C_{24}$ paraffins;

step 1.11 converting unreacted $C_2$-$C_5$ olefins from step 1.9, and the mixture of $C_2$-$C_4$ olefins and $C_1$-$C_4$ paraffins, obtained in step 1.1, by aromatization into $C_7$-$C_{12}$ aromatic hydrocarbons, hydrogen, and a mixture of $C_1$-$C_4$ paraffins, wherein a first portion of the hydrogen produced is directed to step 1.10, and the remaining second portion of the hydrogen produced and the $C_1$-$C_4$ paraffins mixture are directed to step 1.2;

step 1.12 converting the remaining second portion of the mixture of $C_5$-$C_8$ olefins, obtained in step 1.5, and a portion of $C_2$-$C_8$ alcohols from step 1.3, into $C_7$-$C_{16}$ ethers; and step 1.13 converting the $C_{10}$-$C_{24}$ paraffins, obtained in step 1.7, and the $C_6$-$C_{24}$ paraffins, obtained in step 1.10, into $C_6$-$C_{10}$ gasoline, $C_{11}$-$C_{18}$ kerosene, and $C_{19}$-$C_{24}$ diesel fractions of a motor fuel; converting the $C_7$-$C_{12}$ aromatic hydrocarbons, obtained in step 1.11, into $C_7$-$C_8$ gasoline and $C_9$-$C_{12}$ kerosene fractions of a motor fuel; and converting the $C_7$-$C_{16}$ ethers, obtained in step 1.12, into $C_7$-$C_{10}$ gasoline and $C_{11}$-$C_{16}$ diesel fractions of a motor fuel, and also mixing selected fractions thereof, into a motor fuel selected from gasoline, kerosene, and diesel.

Method 2. The method for producing motor fuel from ethanol in accordance with the Method 1, wherein, in step 1.1, a mixture of ethanol and water having a water content within 25%-35% of the total volume of the mixture, is contacted, at a pressure of 0.5-1.5 MPa and a temperature of 500-515° C., with a heterogeneous catalyst consisting of the following metal oxides: ZnO 60-63% mass, $CeO_2$ 1-6% mass, MgO 12-18% mass; and $Al_2O_3$ 13-23% mass, with the proportions calculated in terms of metal oxide, wherein the mixture of ethanol and water is supplied to the catalyst at a space velocity of 0.5-0.9 $h^{-1}$ thereby producing acetone; the resulting acetone is isolated from the reaction mixture and hydrogenated at a temperature of 100-150° C. and a pressure of 0.5-0.9 MPa in the presence of a catalyst consisting of CuO and $Cr_2O_3$ in a molar ratio of 1:1, by hydrogen obtained from the mixture of ethanol and water, thereby resulting in the isopropanol.

Method 3. The method for producing motor fuel from ethanol in accordance with Method 2, wherein, in step 1.4, the isopropanol reacts in the presence of ditertamyl peroxide at a pressure of P=1.0-5.0 MPa and a temperature of 100-130° C. with the ethylene and is thereby converted into the tertiary $C_5$ and $C_7$ alcohols.

Method 4. The method for producing motor fuel from ethanol in accordance with Method 2, wherein, in step 1.4, the unreacted ethanol from step 1.1 reacts in the presence of di-tert-butyl peroxide or di-tert-amyl peroxide under a pressure of P=1.0-5.0 MPa and at a temperature of 100-130° C. with the ethylene to obtain sec-butanol, which is then reacted with ethylene and is converted into the tertiary $C_6$ and $C_8$ alcohols.

Method 5. The method for producing motor fuel from ethanol in accordance with Method 1, wherein, in step 1.8, the ethylene or propylene is converted in the hydroformylation in the presence of a water-soluble Rh catalyst, with a concentration of metal in relation to the aqueous phase of from 30 ppm to 50 ppm, at a temperature of 70-90° C. and a pressure of P=1.0-5.0 MPa into propanal or n-butanal and isobutanal, thereafter a mixture of propanal, n-butanal, and acetaldehyde, obtained in step 1.1, is converted by cross-aldol condensation in the presence of a heterogeneous catalyst containing at least 93% of ZSM-5 zeolite modified by 3.5-7.0% Zn, or a granular catalyst containing at least 95% of ZSM-5 zeolite modified by 3.5-5.0% Zn and 0.1-1.5% Ce into a mixture of $C_3$-$C_4$ aldehydes and $C_5$-$C_8$ aldols, thereafter the mixture of $C_3$-$C_4$ aldehydes and $C_5$-$C_8$ aldols is hydrogenated in the presence of heterogeneous catalyst consisting of NiO, CuO, and $Cr_2O_3$ in a molar ratio of 1:1:1, at a temperature of 150-200° C. and a pressure of P=4.5-5.0 MPa, to obtain the mixture of $C_3$-$C_8$ alcohols.

Method 6. The method for producing motor fuel from ethanol in accordance with Method 5, wherein Triphenylphosphine-sulfonic acid sodium salts, namely: from Triphenylphosphine-3-sulfonic acid sodium salt to Triphenylphosphine-3,3',3"-trisulfonic acid trisodium salt in a weight ratio (10-30): 1 to metal Rh are used as a ligand in the step 1.8 in the hydroformylation of the ethylene or propylene for obtaining the water-soluble catalyst.

Method 7. The method for producing motor fuel from ethanol in accordance with Method 6, wherein, in order to increase the reaction rate and the yield of isobutanal in step 1.8, the hydroformylation of propylene by synthesis gas is carried out in the presence of a water-soluble Rh catalyst prepared in accordance with claim 6; $C_2$-$C_3$ alcohols are added to said catalyst in a volume ratio $H_2O$:$(C_2$-$C_3)$=(0.95-0.65):(0.05-0.35), while the ratio of butanal and isobutanal obtained in the reaction medium is in the range (n-$C_4H_8O$):(iso-$C_4H_8O$)=(2-3): 1.

Method 8. The method for producing motor fuel from ethanol in accordance with Method 1, wherein, in step 1.8, the ethylene or propylene is converted in the hydroformylation reaction in the presence of a water-soluble Co catalyst, with a concentration of Co metal in relation to the aqueous phase of from 0.1% to 1.0%, at a temperature of 120-140° C. and a pressure of P=2.0-5.0 MPa, into propanal, 2-methylpentenal and 2-methylpentanal or into n-butanal, 2-ethylhexenal, 2-ethylhexanal and isobutanal, and thereafter the mixture of $C_3$-$C_4$ aldehydes and $C_6$-$C_8$ aldols are in the presence of a heterogeneous catalyst consisting of NiO, CuO and $Cr_2O_3$ in a molar ratio of 1:1:1, at a temperature of 150-200° C. and a pressure of P=4.5-5.0 MPa hydrogenated to obtain the mixture of $C_3$-$C_8$ alcohols.

Method 9. The method for producing motor fuel from ethanol in accordance with Method 8, wherein, in step 1.8, Triphenylphosphine-sulfonic acid sodium salts, namely: from Triphenylphosphine-3-sulfonic acid sodium salt to Triphenylphosphine-3,3',3"-trisulfonic acid trisodium salt are used as a ligand in a weight ratio (1-30): 1 to metal Co in the hydroformylation of ethylene or propylene for obtaining the water-soluble Co catalyst.

Method 10. The method for producing motor fuel from ethanol in accordance with Method 9, wherein, in order to increase the reaction rate and the yield of isobutanal in step 1.8, in the hydroformylation of propylene $C_2$-$C_3$ alcohols are added to the catalyst in a volume ratio $H_2O$:($C_2$-$C_3$)=(0.95-0.5):(0.05-0.5), wherein the ratio of butanal and isobutanal obtained in the reaction medium is in the range of (n-$C_4H_8O$):(iso-$C_4H_8O$)=(2-3): 1.

Method 11. The method for producing motor fuel from ethanol in accordance with Method 1, wherein, in step 1.9, the $C_2$-$C_8$ olefins are oligomerized in the presence of a heterogeneous catalyst containing at least 93% of ZSM-5 zeolite modified by 3.5-7.0% Zn, or a heterogeneous catalyst containing at least 95% of ZSM-5 zeolite modified by 3.5-5.0% Ce at a temperature of 250-350° C. and a pressure of P=4.5-5.0 MPa to obtain the $C_6$-$C_{24}$ olefins, wherein unreacted $C_2$-$C_5$ olefins are separated by rectification from the $C_6$-$C_{24}$ olefins and directed to step 1.11; wherein, in step 1.10, hydrogenation of $C_6$-$C_{24}$ olefins is carried out in the presence of a heterogeneous catalyst consisting of NiO, CuO and $Cr_2O_3$ in a molar ratio of 1:1:1, at a temperature of 150-200° C. and a pressure of P=4.5-5.0 MPa to obtain the $C_6$-$C_{24}$ paraffins; and wherein, in step 1.13, the $C_6$-$C_{24}$ paraffins are rectified to isolate the $C_6$-$C_{10}$ paraffin gasoline fraction, the $C_{11}$-$C_{18}$ paraffin kerosene fraction, and the $C_{19}$-$C_{24}$ paraffin diesel fraction of a motor fuel.

Method 12. The method for producing motor fuel from ethanol in accordance with Method 11, wherein, in step 1.11, the unreacted $C_2$-$C_5$ olefins are aromatized together in a mixture with $C_2$-$C_4$ olefins and $C_1$-$C_4$ paraffins, in the presence of a heterogeneous catalyst containing at least 93% of ZSM-5 zeolite modified by 3.5-7.0% Zn at a temperature of 350-450° C. and a pressure of P=0.5-2.0 MPa to yield the aromatic $C_7$-$C_{12}$ compounds, and, wherein, in step 1.13, the aromatic $C_7$-$C_{12}$ compounds are rectified to isolate the $C_7$-$C_8$ aromatic compound gasoline fraction, and the $C_9$-$C_{12}$ aromatic compound kerosene fraction of a motor fuel.

Method 13. The method for producing motor fuel from ethanol in accordance with Method 1, wherein, in step 1.6, the $C_5$-$C_8$ olefins are oligomerized using an ion-exchange resin in the form of a cation exchanger, preferably Amberlite 15, as a catalyst, at a temperature of 70-120° C. and a pressure P=1.0-2.0 MPa, and, wherein, in step 1.7, the $C_{10}$-$C_{24}$ olefins are hydrogenated in the presence of a heterogeneous catalyst consisting of NiO, CuO and $Cr_2O_3$ in a molar ratio of 1:1:1 at a temperature of 150-200° C. and pressure P=4.5-5.0 MPa to obtain the mixture of $C_{10}$-$C_{24}$ paraffins, and, wherein, in step 1.13, the $C_{10}$-$C_{24}$ paraffins are rectified to isolate the $C_{11}$-$C_{18}$ paraffin kerosene fraction, and the $C_{19}$-$C_{24}$ paraffin diesel fraction of a motor fuel, wherein remaining $C_{10}$ paraffins are mixed with the $C_6$-$C_{10}$ paraffin gasoline fraction of a motor fuel, obtained in step 1.13 by rectification of the $C_6$-$C_{24}$ paraffins.

Method 14. The method for producing motor fuel from ethanol in accordance with Method 13, wherein, in step 1.12, the etherification is carried out on a mixture of the $C_5$-$C_8$ olefins and the $C_2$-$C_8$ alcohol using as a catalyst an ion exchange resin in the form of a cation exchanger, preferably Amberlite 15, at a temperature of 70-120° C. and pressure P=1.5-2.0 MPa, to yield the $C_7$-$C_{16}$ ethers, and, wherein, in step 1.13, the $C_7$-$C_{16}$ ethers obtained, are rectified to isolate a $C_7$-$C_9$ ether fraction for producing gasoline, and a $C_{10}$-$C_{16}$ ether fraction for producing diesel.

Method 15. The method for producing motor fuel from ethanol in accordance with Method 1, wherein, in step 1.13, in order to obtain kerosene fully complying with the requirements of the current Jet A-1 standard, $C_{11}$-$C_{18}$ paraffins are isolated from the $C_6$-$C_{24}$ paraffins mixture obtained from step 1.10, $C_{11}$-$C_{18}$ paraffins are isolated from the mixture of $C_{10}$-$C_{24}$ paraffins obtained in step 1.7, and aromatic $C_9$-$C_{12}$ hydrocarbons, are isolated from the $C_7$-$C_{12}$ aromatic hydrocarbons mixture obtained in the step 1.11, and the isolated $C_{11}$-$C_{18}$ paraffins and aromatic $C_9$-$C_{12}$ hydrocarbons are mixed so that the concentration of aromatic $C_9$-$C_{12}$ hydrocarbons is in the range of 8-25% vol, and so that the resulting kerosene will contain at least 100 different hydrocarbons, and preferably 150 different hydrocarbons, have a Smoke Point of minimum 30 mm, and a Freezing Point of maximum minus 80° C.

What is claimed is:

1. A method for making a motor fuel, comprising:
   (a) converting a mixture comprising one or more $C_2$-$C_4$ alkenes, synthesis gas, and acetaldehyde to a mixture comprising $C_3$-$C_4$ aldehydes and $C_5$-$C_8$ aldols;
   (b) hydrogenating the mixture comprising $C_3$-$C_4$ aldehydes and $C_5$-$C_8$ aldols to obtain a mixture comprising $C_3$-$C_8$ alcohols;
   (c) converting the $C_3$-$C_8$ alcohols into $C_6$-$C_{24}$ paraffins; and
   (d) isolating a fraction of the $C_6$-$C_{24}$ paraffins.

2. The method of claim 1, further comprising:
   using the isolated fraction to formulate the motor fuel.

3. The method of claim 1, wherein step (b) is conducted in the presence of heterogeneous catalyst comprising NiO, CuO, and $Cr_2O_3$ in a molar ratio of 1:1:1, at a temperature of 150 to 200° C. and a pressure of 4.5 to 5.0 MPa.

4. The method of claim 1, wherein step (a) employs a heterogeneous catalyst.

5. The method of claim 1, wherein step (a) employs a water-soluble Rh catalyst.

6. The method of claim 5, wherein the rhodium catalyst comprises a ligand comprised of a triphenylphosphine-sulfonic acid sodium salt.

7. The method of claim 1, wherein step (a) employs a water-soluble Co catalyst.

8. The method of claim 7, wherein the water-soluble Co catalyst comprises a ligand comprised of a triphenylphosphine-sulfonic acid sodium salt.

9. The method of claim 1, wherein step (a) comprises a hydroformylation reaction and then an aldol condensation reaction.

10. The method of claim 9, wherein the hydroformylation reaction is conducted in the presence of a water-soluble Rh catalyst, with a concentration of metal in relation to the aqueous phase of from 30 ppm to 50 ppm, at a temperature of 70 to 90° C. and a pressure of 1.0 to 5.0 MPa.

11. The method of claim 9, wherein the hydroformylation reaction is conducted in the presence of a water-soluble Co catalyst, with a concentration of Co metal in relation to the aqueous phase of from 0.1% to 1.0%, at a temperature of 120 to 140° C. and a pressure of 2.0 to 5.0 MPa.

12. The method of claim 9, wherein the hydroformylation reaction comprises adding $C_2$-$C_3$ alcohols to the catalyst.

13. The method of claim 9, wherein the aldol condensation reaction is conducted in the presence of a heterogeneous catalyst containing at least 93% of ZSM-5 zeolite modified by 3.5 to 7.0% Zn, or a granular catalyst containing at least 95% of ZSM-5 zeolite modified by 3.5 to 5.0% Zn and 0.1 to 1.5% Ce.

14. The method of claim 1, wherein step (c) comprises a dehydration reaction, an oligomerization reaction and then a hydrogenation reaction.

15. The method of claim 14, wherein the hydrogenation reaction of step (c) is conducted in the presence of a granular catalyst comprising the oxides NiO, CuO and $Cr_2O_3$ in a molar ratio of 1:1:1.

16. The method of claim 14, wherein the oligomerization reaction is conducted in the presence of a heterogeneous catalyst containing at least 93% ZSM-5 modified by 3.5 to 7.0% Zn, or in the presence of a heterogeneous catalyst containing at least 95% ZSM-5 modified by 3.5 to 5.0% Zn and 0.1 to 1.5% Ce, at a temperature of 250 to 350° C. and a pressure of 2.0 to 5.0 MPa.

17. The method of claim 16, wherein the $C_6$-$C_{24}$ paraffins are mainly branched hydrocarbons.

18. The method of claim 17, wherein the $C_6$-$C_{24}$ paraffins have a linear molecule content of not higher than 5% and are substantially free of aromatic and cyclic compounds.

19. A method for making alcohols, comprising:

hydroformylating synthesis gas and a mixture comprising $C_2$-$C_3$ alkenes to form a mixture comprising one or more $C_3$-$C_4$ aldehydes;

adding acetaldehyde and aldol condensing the acetaldehyde and the mixture comprising $C_3$-$C_4$ aldehydes to form a mixture comprising $C_3$-$C_4$ aldehydes and $C_5$-$C_8$ aldols; and hydrogenating the mixture comprising $C_3$-$C_4$ aldehydes and $C_5$-$C_8$ aldols to form a mixture comprising $C_3$-$C_8$ alcohols.

20. The method of claim 19, wherein the mixture comprising $C_3$-$C_8$ alcohols is primarily branched alcohols.

* * * * *